US006673317B2

(12) United States Patent
Hashimoto et al.

(10) Patent No.: US 6,673,317 B2
(45) Date of Patent: Jan. 6, 2004

(54) AUTOMATIC TESTING APPARATUS

(75) Inventors: Kiyoji Hashimoto, Okayama (JP); Masanori Matsumoto, Ibara (JP); Masaru Fujimoto, Ibara (JP); Mamoru Shiratori, Tokyo (JP); Masato Ichikawa, Tokyo (JP)

(73) Assignees: Kasen Nozzle Mfg. Co., Ltd., Osaka (JP); Kasen Engineering Corp., Osaka (JP); Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/202,806

(22) PCT Filed: Jun. 27, 1997

(86) PCT No.: PCT/JP97/02236
§ 371 (c)(1), (2), (4) Date: Dec. 22, 1998

(87) PCT Pub. No.: WO98/00520
PCT Pub. Date: Jan. 8, 1998

(65) Prior Publication Data
US 2001/0053335 A1 Dec. 20, 2001

(30) Foreign Application Priority Data

Jun. 28, 1996 (JP) .............................. 8-188661
Jun. 28, 1996 (JP) .............................. 8-188880

(51) Int. Cl.⁷ .............................. G01N 35/00

(52) U.S. Cl. .............. 422/65; 422/63; 422/67; 422/100; 422/101; 422/102; 422/104; 436/43; 436/47; 436/49; 436/54; 436/174; 436/180

(58) Field of Search ............... 422/63, 65, 67, 422/100, 102, 101, 104; 436/43, 47, 49, 54, 174, 180; 73/864.23, 864.24, 864.25

(56) References Cited

U.S. PATENT DOCUMENTS 4,713,974 A * 12/1987 Stone ..................... 73/864.23
4,835,707 A * 5/1989 Amano et al. ............. 364/497
4,877,964 A * 10/1989 Tanaka et al. ......... 250/455.11

(List continued on next page.)

FOREIGN PATENT DOCUMENTS

| JP | 63230077 | 9/1988 | ............ C12M/1/34 |
| JP | 4506750 | 11/1992 | ............ C12M/1/34 |
| JP | 6160377 | 6/1994 | .......... G01N/33/18 |
| JP | 08228759 | 9/1996 | ............ C12M/1/34 |
| WO | 9315407 | 5/1993 | |
| WO | WO-9747974 A2 * | 12/1997 | |

OTHER PUBLICATIONS

Valcarcel, M. et al.,"Automatic Methods of Analysis", Techniques and Instrumentation in Analytical Chemistry, Elsevier, vol. 9. pp. 250–272.*

Primary Examiner—Jill Warden
Assistant Examiner—Kathryn Bex
(74) Attorney, Agent, or Firm—Ladas & Parry

(57) ABSTRACT

In order to provide an automatic testing apparatus with improved reliability of test results, capable of conducting automatically such operations as sterile testing, microorganism limit testing, insoluble particulate measurement testing, divided portion testing for chemical analysis and chemical reaction testing, etc., and capable of accommodating changes in the specimen or the test container with each sample as well as changes in operating procedures with each sample so as to eliminate the possibility of human error and prevent contamination of the operating environment by human hands, the automatic testing apparatus of the present invention prepares a sample by mounting a set of various pieces of equipment including the specimen or test containers required to be changed with every sample atop a same work base and providing that work base as a unit to within the operating range of a robot, with the robot then handling the various pieces of equipment atop the work base to prepare the sample.

2 Claims, 59 Drawing Sheets

OTHER PUBLICATIONS

| | | | | | |
|---|---|---|---|---|---|
| 4,928,539 A | * | 5/1990 | Champseix et al. | ...... | 73/864.24 |
| 4,951,513 A | * | 8/1990 | Koike | ...................... | 73/864.25 |
| 5,305,650 A | * | 4/1994 | Koike et al. | ............. | 73/864.21 |
| 5,395,198 A | * | 3/1995 | Duffy et al. | ................. | 118/500 |
| 5,422,075 A | * | 6/1995 | Saito et al. | ............. | 250/361 C |
| 5,431,201 A | * | 7/1995 | Torchia et al. | ................. | 141/98 |
| 5,464,580 A | * | 11/1995 | Popescu et al. | ................. | 422/1 |
| 5,472,669 A | * | 12/1995 | Miki et al. | ..................... | 422/63 |
| 5,580,524 A | * | 12/1996 | Forrest et al. | ................. | 422/63 |
| 5,928,952 A | * | 7/1999 | Hutchins et al. | .............. | 436/50 |

* cited by examiner

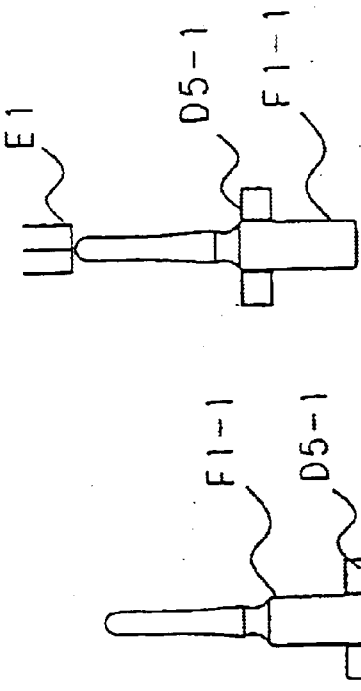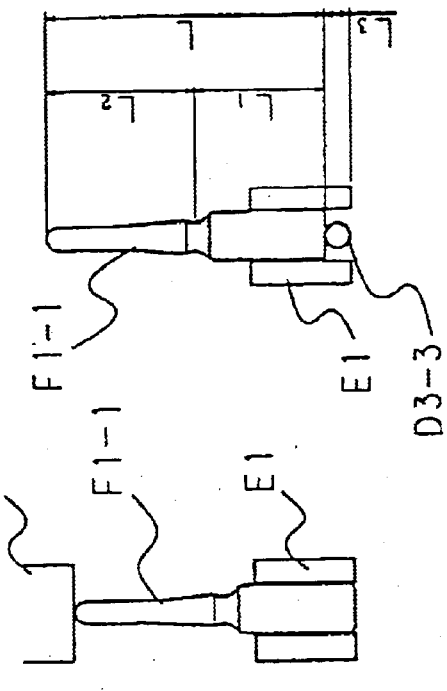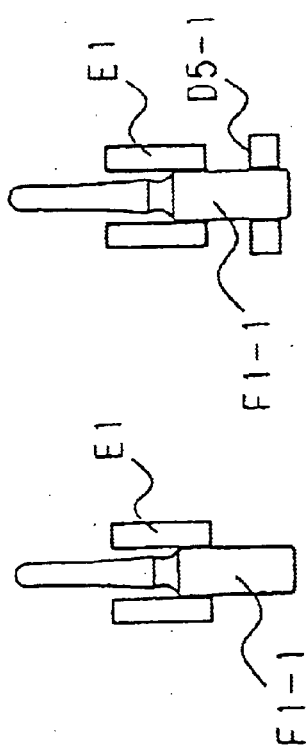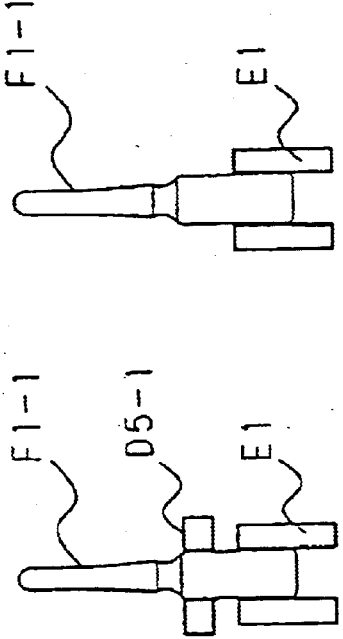

AUTOMATIC TESTING APPARATUS

FIELD OF THE INVENTION

An operation of making a culture medium from a specimen in order to determine the presence or absence of bacteria or fungi in a specimen comprising a vial filled with powder or fluid by using a membrane filter is known.

The present invention concerns a sterile test apparatus for testing this vial, and more particularly an apparatus that makes maximum use of the benefits of an operating apparatus for sterile testing.

However, the present invention is not limited to a sterile test apparatus; with a partial alteration and/or addition, it can also be similarly used as an automatic testing apparatus for all microorganism testing as well as an automatic testing apparatus for insoluble particulate testing done under the same conditions and performing the same operations as those for sterile testing.

Therefore, the present invention concerns an automatic testing apparatus that can be utilized for all the above-mentioned tests.

The following explanation uses an example of the present invention utilized as an automatic sterile testing apparatus.

BACKGROUND OF THE INVENTION

Conventionally, the making of a sample in order to determine the presence or absence of germs by using a membrane filter method, as for example shown in the drawings (FIG. 1) describing the conventional art in Laid-Open Patent Application No. 63-230077, has involved a vacuum suction filtration method employing syringes, flasks, funnels and the like, and has been performed entirely as a manual operation.

However, this vacuum suction filtration method presupposes operation by human hands inside a clean room, and it is difficult to completely prevent contamination of the clean room by technicians. That is, with the vacuum suction filtration method there is a possibility of obtaining false positive readings because of the possibility that ambient air gets drawn into the specimen, thus calling into question the accuracy of the test.

In order to solve this problem a sterile test unit employing a pressurized filtration method consisting of a suction needle and two culture tubes to each of which is connected two tubes has been developed, greatly reducing the introduction of germs from the operating environment into the specimen during testing.

However, even with use of this sterile test unit it is difficult to prevent contamination of the environment by people when carrying out a series of manual operations inside the clean room and the introduction of germs cannot be completely eliminated. In addition, existing problems of procedural mistakes during operation, poor test efficiency and high cost remain unaddressed.

As a means of resolving these problems the vial automatic sterile test unit of Laid-Open Patent Application 63-230077 previously mentioned has been developed. However, said apparatus, too, has the following problems and is not the fundamental problem resolution sought for sterile testing operations.

1) When the necessary equipment is added to said apparatus (in the preparatory stage), humans must enter the clean room in order to work. The interior of the clean room is contaminated when humans enter the clean room, sterile testing is done in a contaminated environment and the possibility of false positives remains a concern.

2) When a plurality of samples of different funnels are positioned at said apparatus, the structure of the apparatus is such that the injection needle used to inject the solutions does not change even though the sample changes, so there is a chance that the samples may be contaminated beginning with the second sample.

3) The specimen transport tray must be replaced every time there is a change in either the shape of the specimen container, the volume of the specimen per single sample, the shape of containers other than those of the specimen, the volume or the testing order, making for extraordinarily frequent and complex operation and an extraordinarily large number of trays, necessitating storage space for the trays and creating a large additional burden of keeping track of the trays as well.

4) The stock device for all the container cases is a surface-arrangement type and moreover a stock device is needed for both before and after testing, so the larger the number of samples per device the greater the area required by the device, which means that the number of samples that can be processed per set inside an existing clean room cannot be large.

5) The order of operation is fixed and each and every one of these processes must be started simultaneously, so the interval required by the process that takes the longest is the required interval, making the entire time required for the test very lengthy.

6) The order of operation is fixed, so when the same operation is repeated additional devices for such operation must be added to the apparatus, increasing the area required and adding to the cost.

7) The unit only uses vials, and cannot be adapted either to other types of specimen containers (such as ampules, transfusion solution bags, eyedroppers, etc.) or to other purposes (such as the direct method of making samples for sterile testing), making it necessary consider other types of equipment adapted to each type of container or vial.

SUMMARY OF THE INVENTION

It is the general object of the present invention to provide an improved and useful automatic testing apparatus that solves problems like those mentioned above.

A more specific object of the present invention is to provide an automatic testing apparatus that performs automatically, without any human intervention whatsoever, even when there are changes in the operations required for the test depending on the shape and size of the specimen to be tested, the method of testing or the order of operations, and which reduces the frequency and complexity of operations and performs mistake-free operation with a high degree of accuracy.

The object of the present invention is achieved by an automatic testing apparatus comprising a work base mounting the test specimen as well as equipment required for the testing of the specimen; a robot device for moving according to a previously determined procedure said test specimen and equipment mounted on said work base set at a predetermined testing position for performing predetermined tests on a test specimen mounted on the work base; and a work base providing mechanism for providing the work base to the testing position, such that the specimen to be tested can be changed on a work base-unit basis.

According to the above-mentioned automatic testing apparatus, by simply setting the test specimen as well as the equipment required for the test specimen on the work base, the test specimen and equipment mounted on said work base are moved by the robot device according to a predetermined order and the required tests executed. As a result, by pre-programming the robot device to perform test procedures on an individual work-base basis for each test specimen, a variety of tests are performed automatically without human intervention, thus reducing the frequency and complexity of operations and making it possible to perform mistake-free operations of high reliability.

In addition, another object of the present invention is to provide an automatic testing apparatus that is capable of performing automatically the many above-mentioned operations with respect to specimens without fear of contamination by germs from human hands even without the use of a clean room, that is more simplified in structure and from which highly accurate test results can be expected.

The object of the present invention is achieved by an automatic testing apparatus having a sealed first partition chamber enclosing a range of handling operation of a robot device, said first partition chamber comprising a sealable port portion for work base entry and exit, a filter unit positioned on a top portion of said first partition chamber, and exhaust ports positioned on the bottom portion and side surface portions, and structured so as to permit the operation of said robot device inside said first partition chamber comprising a clean booth function.

According to an automatic testing apparatus of this type, the testing of a test specimen on the work base can be carried out automatically by the robot device without fear of contamination by germs from human hands even without the use of a clean room, the automatic testing apparatus itself being one that is more simplified in structure and from which highly accurate test results can be expected.

In addition, the present invention provides on a front step of the first partition chamber a work base stock device so that work bases can be continuously supplied to the first partition chamber that demarcates the range of operation of the robot device, with the work base providing mechanism structured so as to be able to provide from said stock device each work base to said test position inside said partition chamber.

Moreover, the present invention provides on every above-mentioned automatic testing apparatus a sealed second partition chamber enclosing said stock device so that germs can be prevented from entering during the process of providing the test specimen to the robot device, with said second partition chamber comprising a sealable port portion for work base entry and exit and exhaust ports positioned on the bottom portion and side surface portions, so as to permit operation of said stock device inside said second partition chamber comprising a clean booth function.

The present invention can be structured so that the work bases can returnably move between the first partition chamber and the second partition chamber, so that the exchange of work bases is simple.

In addition, the present invention can be made to be equipped with a disinfecting means for spray-misting a disinfectant fluid into at least one of the first partition chamber and second partition chamber, so that the adhesion of germs to the test specimen may be even further prevented.

It is preferable that this disinfectant fluid be strong-acid ionized water.

Similarly, the present invention can be equipped with a UV lamp emitting germ-killing rays and an ozone-generating lamp inside the first partition chamber, so that the adhesion of germs to the test specimen may be even further prevented.

BRIEF DESCRIPTION OF THE DRAWINGS

Other objects, features and advantages of the present invention will become apparent from the following detailed description when read in conjunction with the accompanying drawings.

FIG. 23A shows a condition of a specimen container F1-1 retrieved by the robot hand E1.

FIG. 23B shows a condition of a specimen container held by a container grasping position changing device hand D5-1 of a container grasping position changing device D5.

FIG. 23C shows a condition of a specimen container held by a container grasping position changing device hand D5-1.

FIG. 23D shows the robot hand E1 closed, the tip portion of the specimen container F1-1 pushed so as to make it easy to grasp the lower portion of the specimen container F1-1 with the robot hand.

FIG. 23E shows a condition of the lower portion of the specimen container F1-1 grasped by the robot hand E1.

FIG. 23F shows the container grasping position changing device hand D5-1 in a released condition.

FIG. 23G shows an action of firmly readjusting the grip on the entire specimen container F1-1.

FIG. 23H shows a condition in which the bottom of the specimen container F1-1 is lifted slightly by the holding position setting bar D3-3 in order to set the position at which to notch the ampule with the rotating blade so as to eliminate any effect from a poorly dimensioned neck portion L2.

CONFIGURATIONS FOR IMPLEMENTING THE INVENTION

A description will now be given of the preferred embodiments of the present invention with reference to the drawings.

Figure 1:
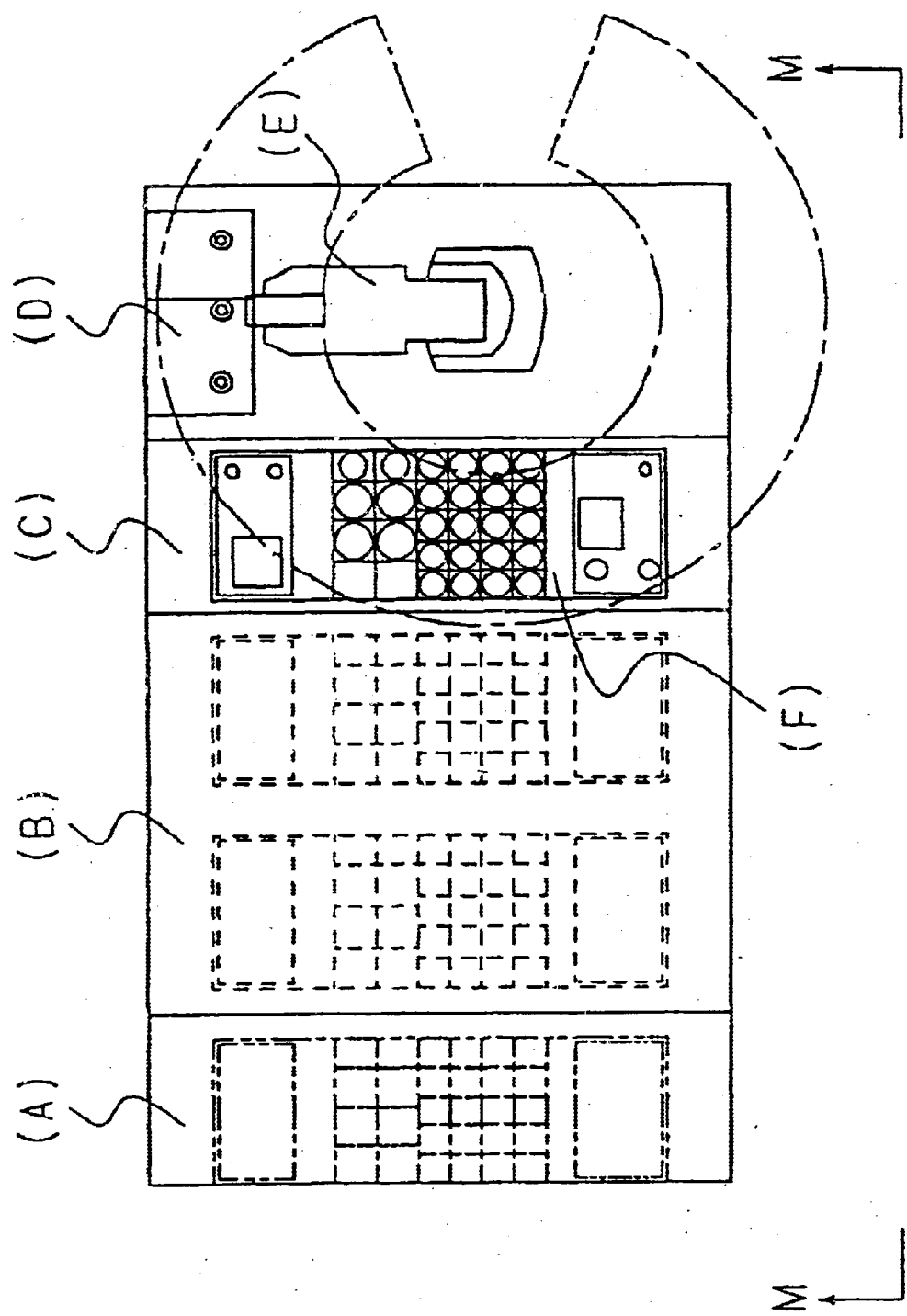
FIG. 1 is a plan view of the entire automatic sterile testing apparatus according to a first embodiment of the present invention.
Figure 2:
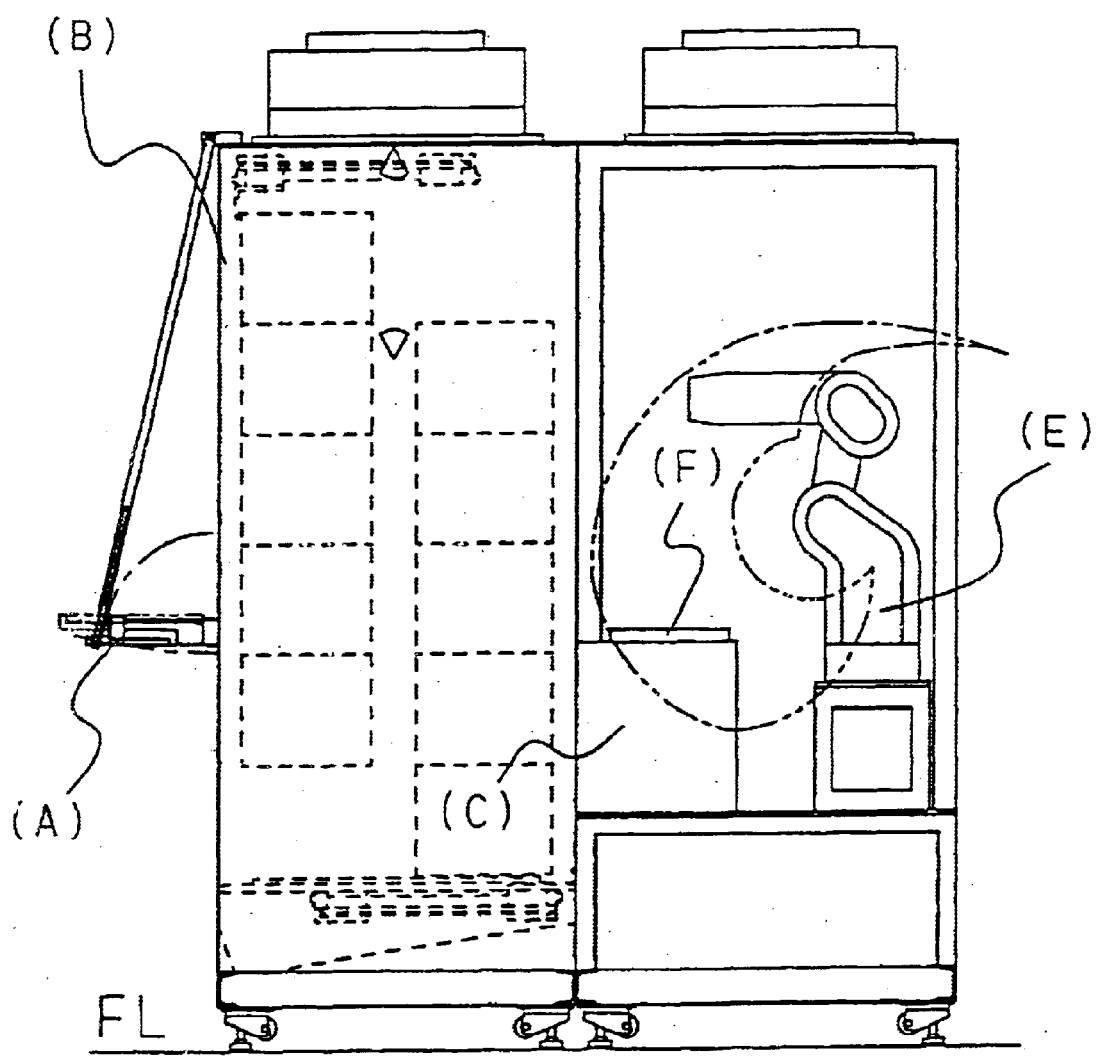
FIG. 2 is a view along the arrows M—M shown in FIG. 1.

As shown in FIG. 1 (plan view of the entire apparatus) and FIG. 2 (view along arrows M—M of FIG. 1), the automatic sterile testing apparatus according to a first embodiment of the present invention comprises a detachably attached work table (A), a work stocker (B), a work manipulation table (C), an auxiliary work manipulation table (D), a work manipulation robot (E) and a work base (F).

Figure 3:
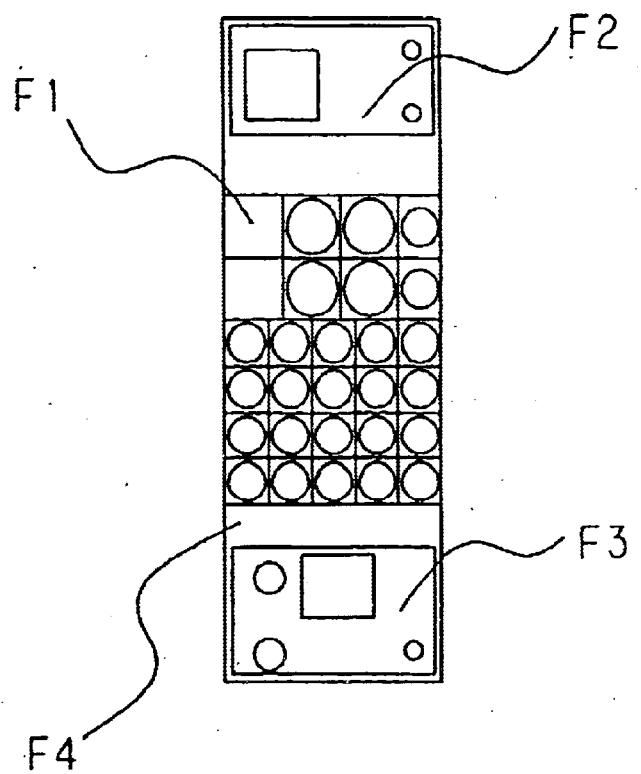
FIG. 3 shows the construction of the work bases used in the apparatus shown in FIG. 1.

As shown in FIG. 3 (work base construction diagram), the work base (F) comprises equipment required for operation as well as equipment required to be changed with each sample, in other words a container case F1; a pump unit F2 for injecting solutions mounting a tube unit for injecting solutions; a pump unit F3 for injecting a variety of solutions mounting a sterile test unit in order to inject a variety of solutions; and a work palette F4 mounted on this equipment.

The container case F1 can be detached from the work palette F4, while the solution injection pump unit F2 and the pump unit F3 for injecting a variety of solutions are attached to the work palette.

Figure 4:
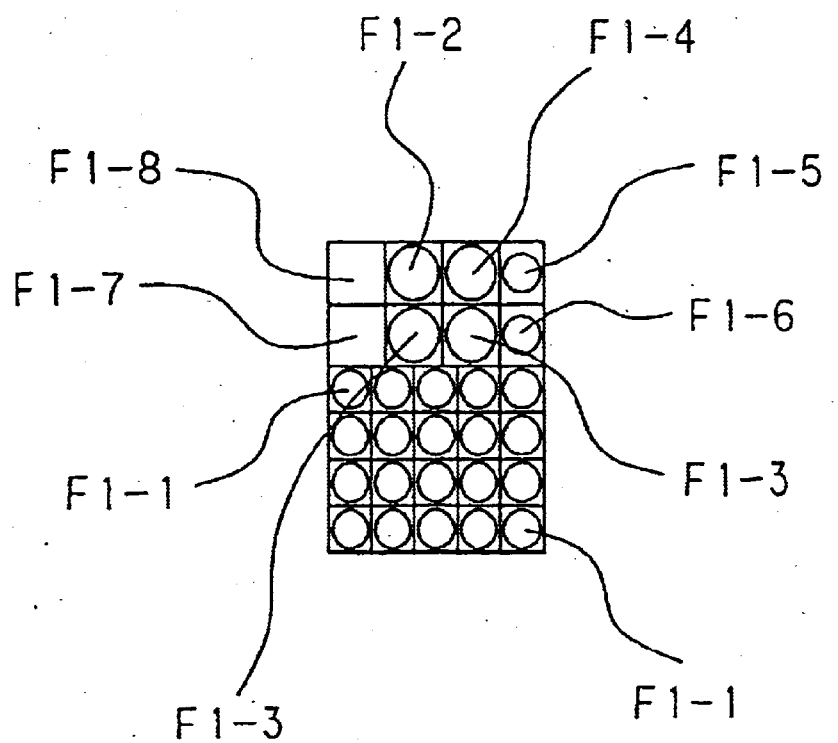
FIG. 4 shows an arrangement of various types of containers on a work palette mounted on the work base shown in FIG. 3.

In the present embodiment, as shown in FIG. 4 (diagram showing an arrangement of various types of containers on a work palette mounted on the work base) the container case F1 is for example provided with specimen containers F1-1 in the form of vials, with 20 specimens per sample (20 containers); one preparatory rinsing fluid container F1-2; two rinsing fluid containers F1-3; one solution container F1-4; one culture medium A container F1-5; and one culture medium B container F1-6, together with one cap container F1-7 and one empty space F1-8.

Figure 5:
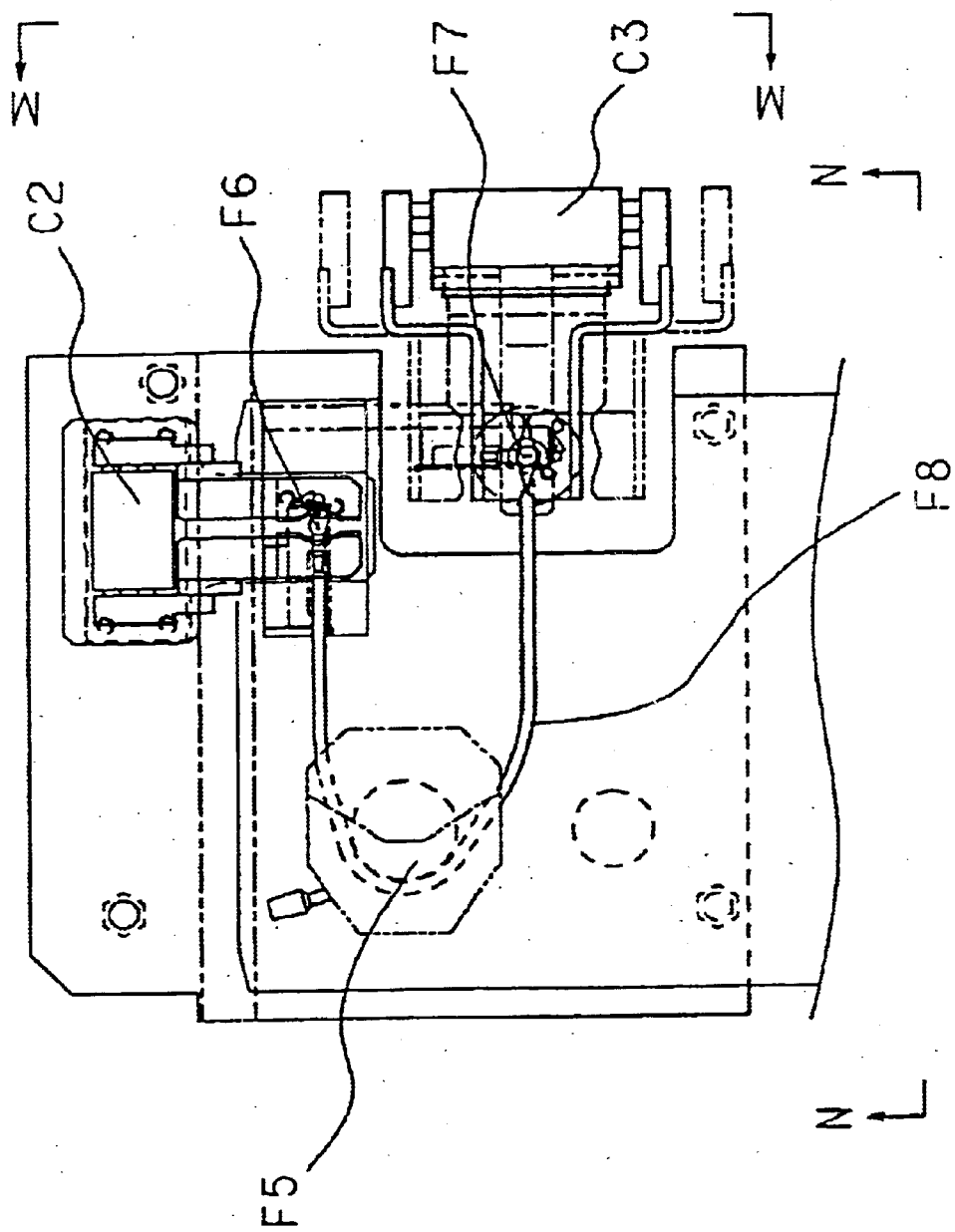
FIG. 5 shows a plan view of a solution injection pump unit used in the apparatus shown in FIG. 1.

As shown in FIG. 5 (plan view of a solution injection pump unit), the solution injection pump unit F2 comprises a solution transfer pump F5, a solution suction needle stand F6 and a solution injection needle stand F7, with a solution injection tube unit F8 set on said solution injection pump unit F2.

Figure 6:
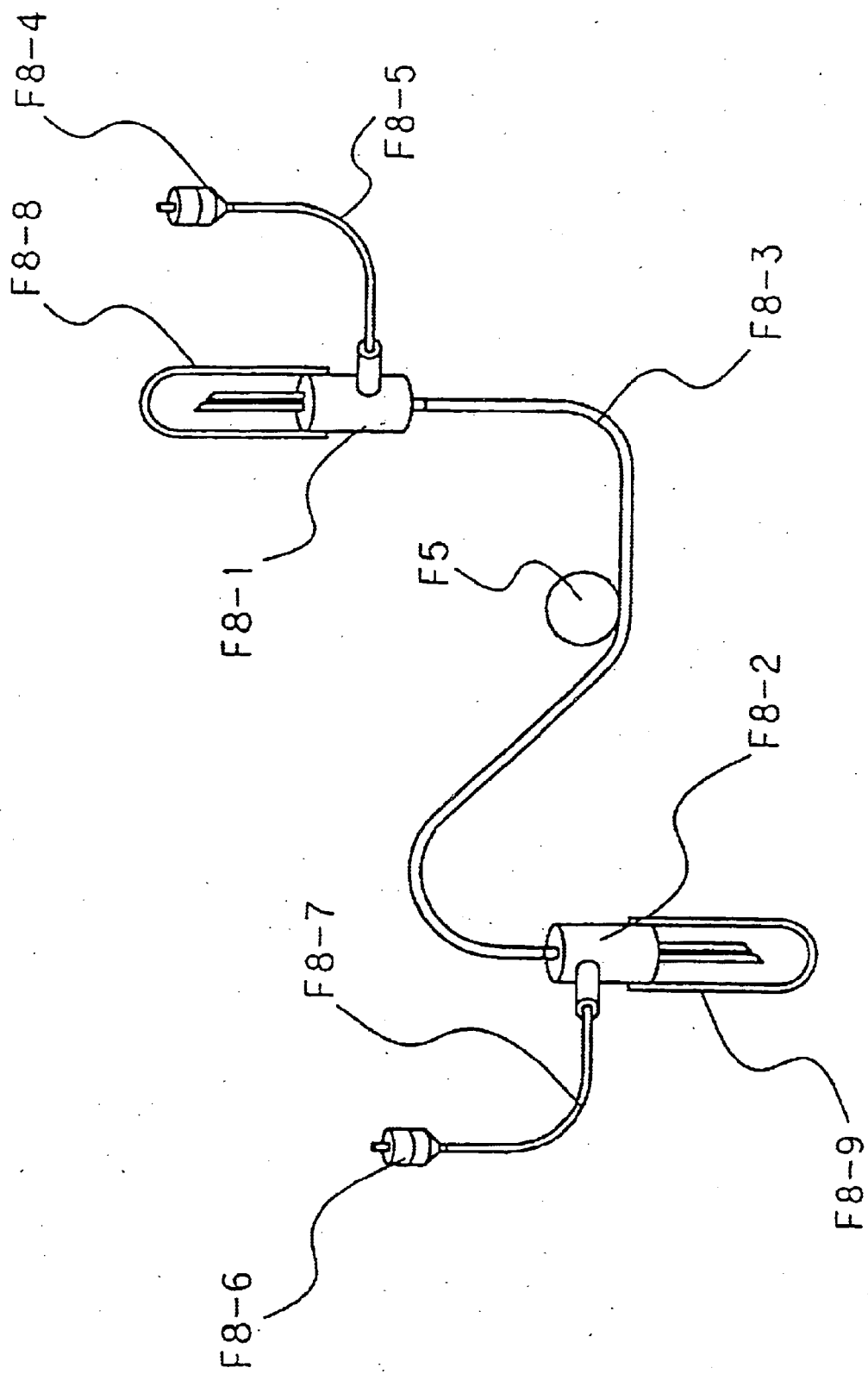
FIG. 6 shows the construction of a solution injection tube unit.

As shown in FIG. 6 (construction of a solution injection tube unit), the solution injection tube unit F8 comprises a solution suction needle F8-1, a solution injection needle F8-2 and a connecting tube F8-3. A first filter F8-4 is connected to said solution suction needle F8-1 via a tube F8-5, while a second filter F8-6 is connected to said solution injection needle F8-2 via a tube F8-7. A first cap F8-8 covers said solution suction needle F8-1 while a second cap F8-9 covers solution injection needle F8-2.

Figure 7:
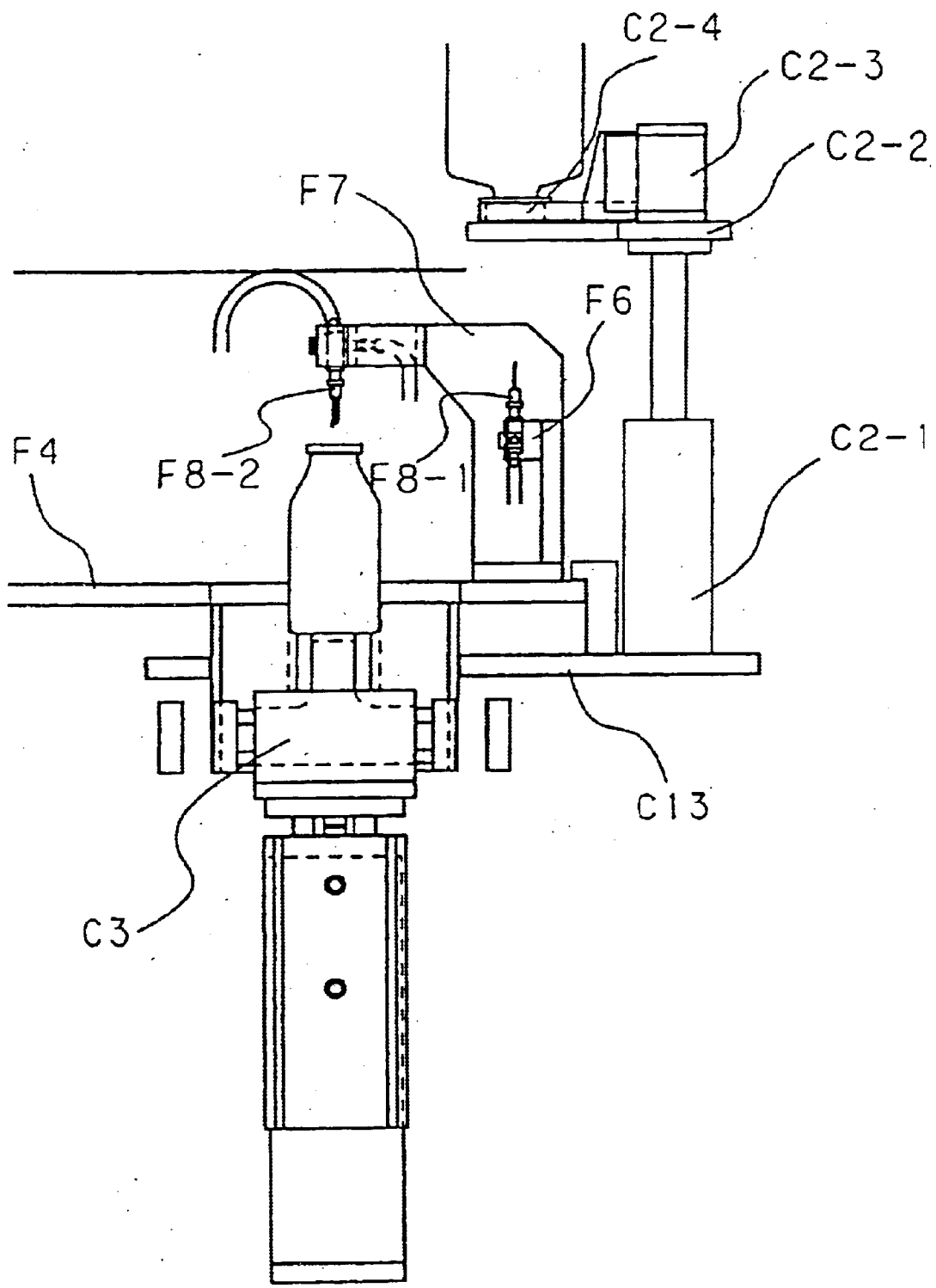
FIG. 7 is a view along the arrows M—M shown in FIG. 5.

As shown in FIG. 5 and FIG. 7 (view along arrows M—M of FIG. 5), the solution suction needle F8-1 of this solution injection tube unit F8 is attached to the solution suction needle stand F6, the solution injection needle F8-2 is attached to the solution injection needle stand F7 and the connecting tube F8-3 is attached to the solution transport pump F5, respectively.

Figure 8:
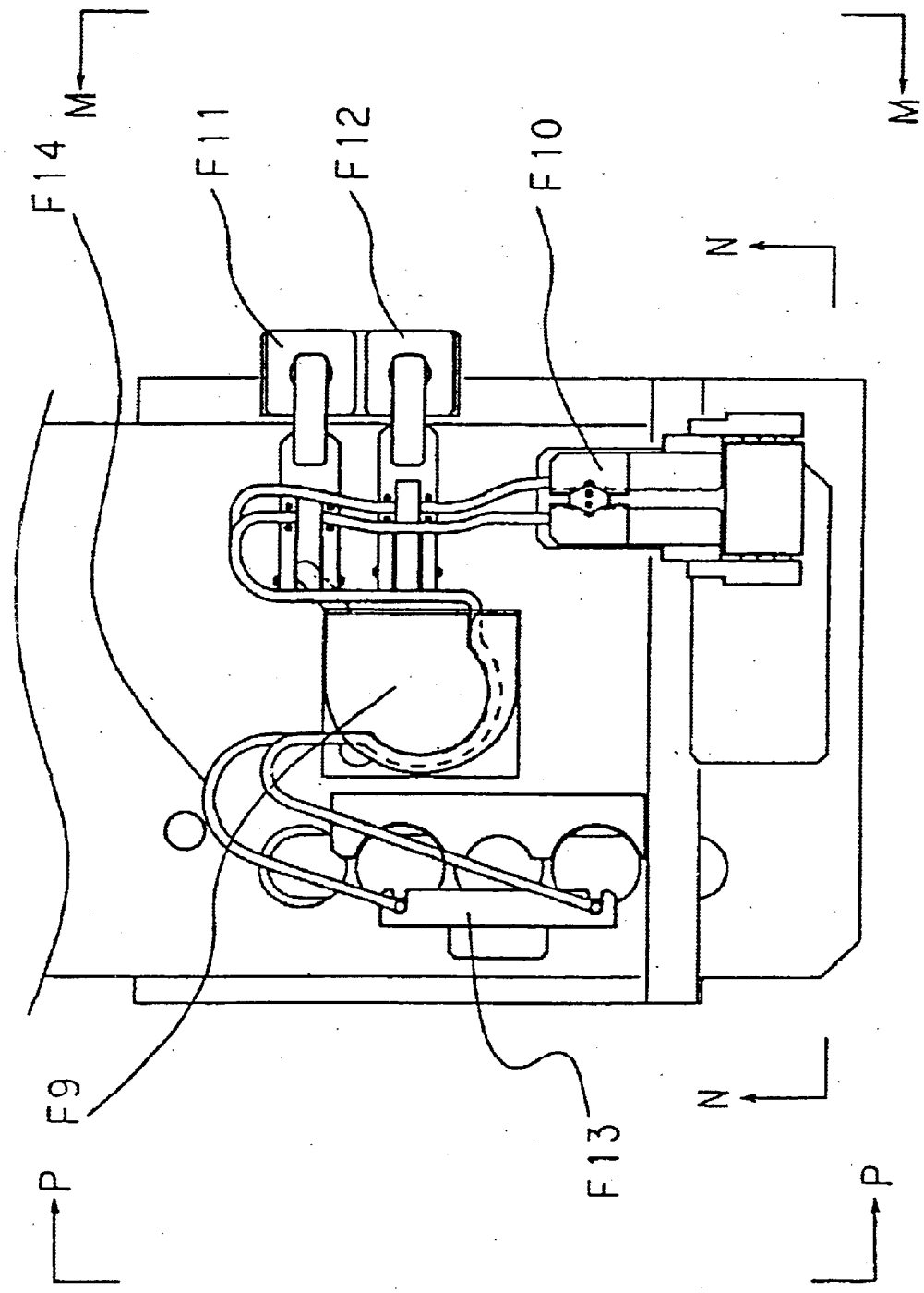
FIG. 8 shows a plan view of a pump unit for injecting a variety of solutions.

As shown in FIG. 8 (plan view of a pump unit for injecting a variety of solutions), the pump unit F3 for injecting a variety of solutions comprises a various-solution transfer pump F9, a solution suction needle stand F10, a first pinch valve F11, a second pinch valve F12 and a culture tube stand F13. A sterile test unit 14 is attached to said pump unit F3 for injecting a variety of solutions.

Figure 9:
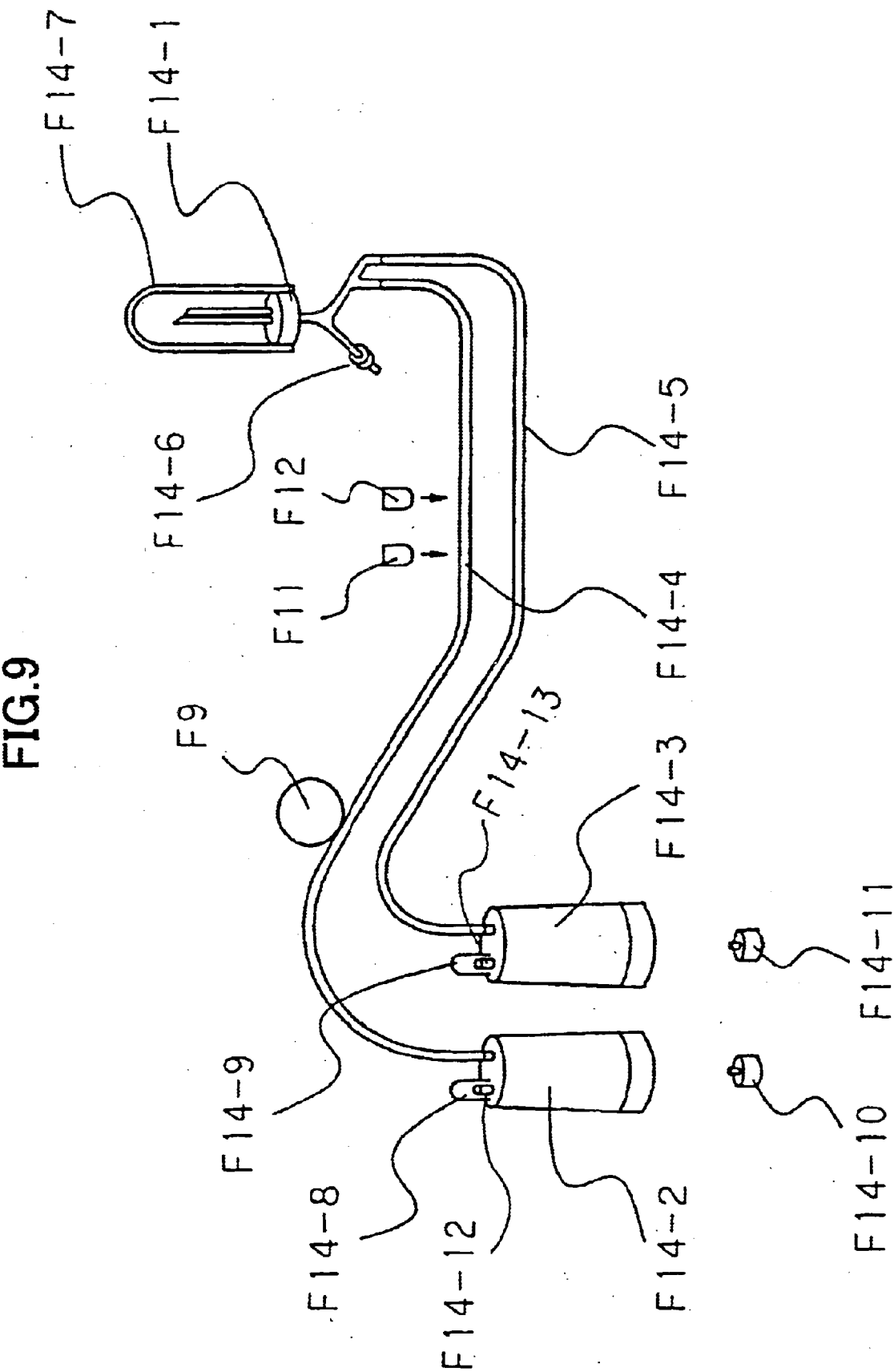
FIG. 9 shows the construction of a sterile test unit.

As shown in FIG. 9 (construction of sterile test unit), said sterile test unit F14 comprises a solution suction needle F14-1, a first culture tube F14-2, a second culture tube F14-3, a first connecting tube F14-4 and a second connecting tube F14-5. To the solution suction needle F14-1 is attached a solution suction needle cap F14-7 and a filter F14-6. A first upper cap F14-8 and a second upper cap F14-9 cover a first upper exhaust port F14-12 and a second upper exhaust port F14-13 of the first culture tube F14-2 and the second culture tube F14-3, respectively, while a first bottom cap F14-10 and a second bottom cap F14-11, respectively, are installed on the lower exhaust ports of the culture tubes.

Figure 10:
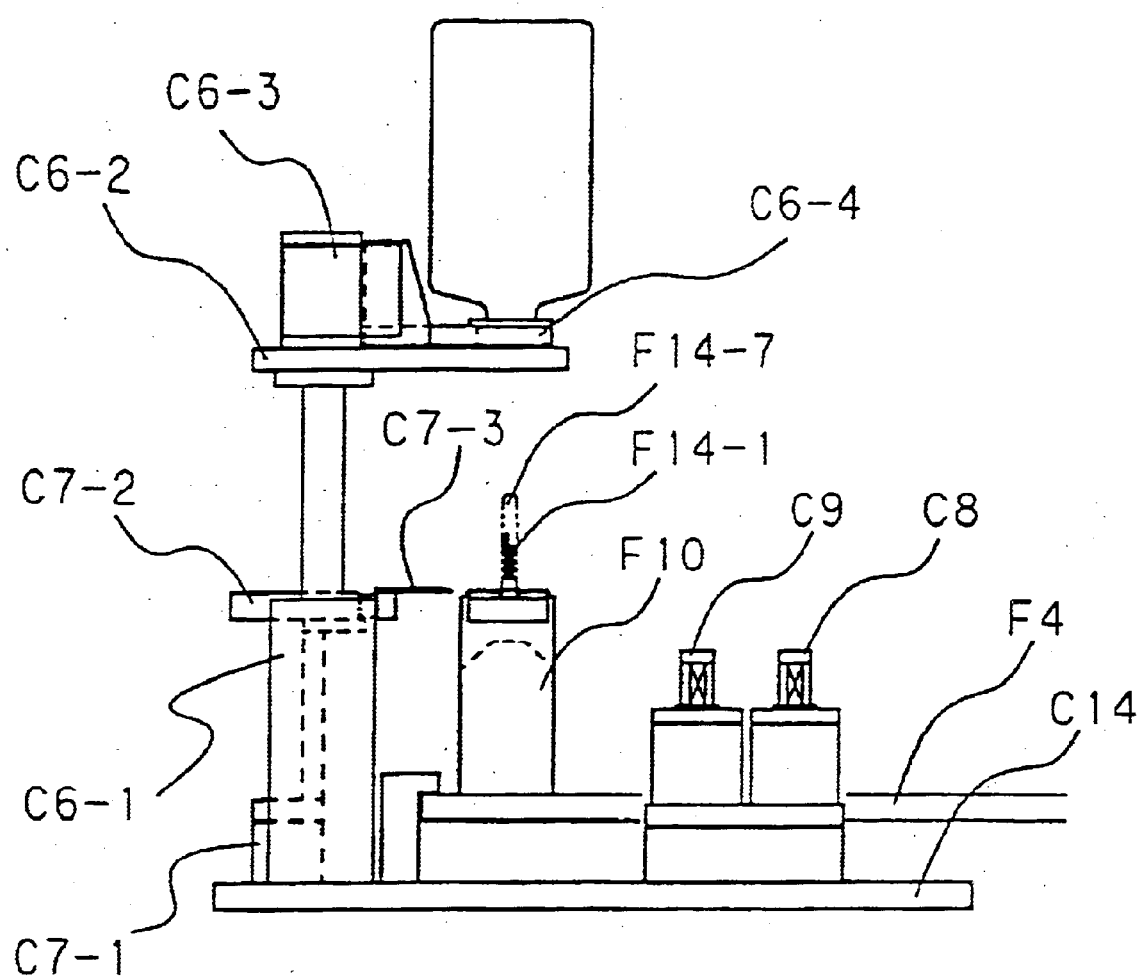
FIG. 10 is a view along arrows M—M shown in FIG. 8.

As shown in FIG. 8 and FIG. 10 (view along arrows M—M shown in FIG. 8), in said sterile test unit F14 the solution suction needle F14-1 is mounted on the solution suction needle stand F10, with the first and second connecting tubes F14-4 and F14-5, respectively, connected to the various-solution transfer pump F9. In between the solution suction needle stand F10 and the various-solution transfer pump F9, the first connecting tube F14-4 is connected to the first pinch valve F11 and the second connecting tube F14-5 is connected to the second pinch valve F12. The first culture tube F14-2 and the second culture tube F14-3 are mounted on the culture tube stand F13.

It has been previously mentioned that the container case F1 is detachably connected to the work palette F4, while the solution injection pump unit F2 and the pump unit F3 for injecting a variety of solutions are fixed to the work palette F4. However, the attachment to and detachment from this solution injection pump unit F2 of the solution injection tube unit F8, as well as the attachment to and detachment from the pump unit F3 for injecting a variety of solutions of the sterile test unit F14, are carried out manually.

Figure 12:
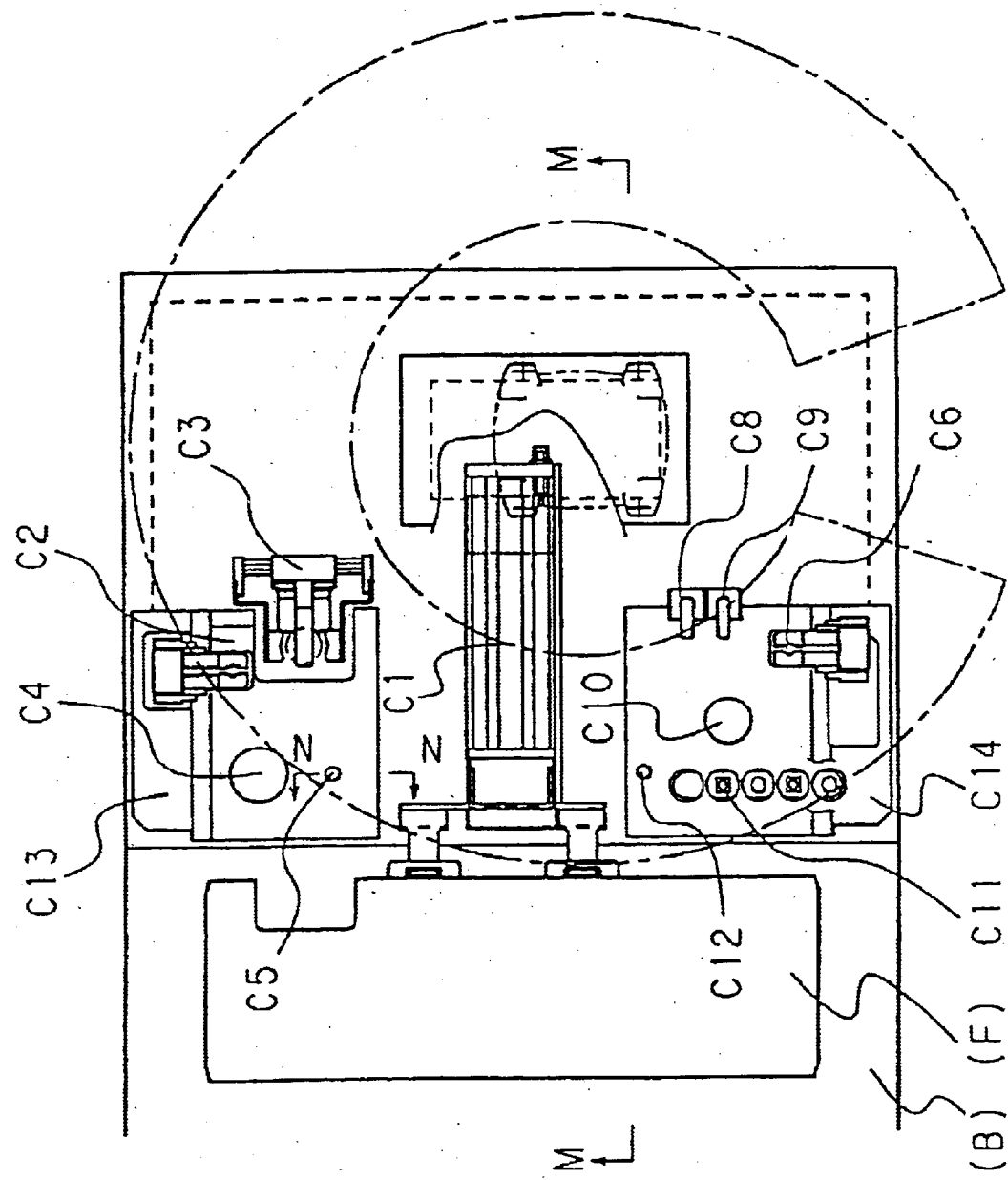
FIG. 12 shows a plan view of a work manipulation table.

As shown in FIG. 12 (plan view of a work manipulation table), the work manipulation table the work manipulation table (C) comprises a work base retrieval and storage device C1 for retrieving the work base (F) from the work stocker (B) and advancing it to a predetermined position of said work manipulation table (C) as well as removing it from the predetermined position of said work manipulation table and storing it in the work (stocker) (B); a table C13 for manipulating the solution to be placed on said work base (F); a table C14 for manipulating a variety of solutions to be placed on said work base F; a first work base position determining device C5 for fixing said work base (F) to said solution manipulation table C13; a second work base position determining device C12 for fixing said work base (F) to said table C14 for manipulating a variety of solutions to be placed on said work base (F); a device C2 for grasping and raising or lowering the solution container, such device being provided on an upper portion of a fixed position of the solution suction needle stand F6; a device C3 for grasping and raising or lowering a specimen container, such device being provided on a lower portion of a fixed position of the solution injection needle stand F7; a solution transport pump rotating device C4 provided on a lower portion of a fixed position of the solution transport pump F5; a device C6 for grasping and raising or lowering a variety of solution containers, such device being provided on a lower portion of a fixed position of the various-solution suction needle stand F10; a device C7 (shown in FIG. 10) for aiding in removing the caps from the various-solution suction needle; a first device C8 for opening and closing a pinch valve, such device being provided on an upper portion of a fixed position of a first pinch valve F11; a second device C9 for opening and closing a pinch valve, such device being provided on an upper portion of a fixed position of a second pinch valve F12; a various-solution transport pump rotating device C10, such device being provided on a lower portion of a fixed position of the various-solution transport pump F5; and a device C11 for attaching and detaching caps on the bottoms of culture tubes, for attaching and detaching a first bottom cap F14-10 and a second bottom cap F14-11 to and from a first culture tube F14-2 and a second culture tube F14-3.

Figure 13:
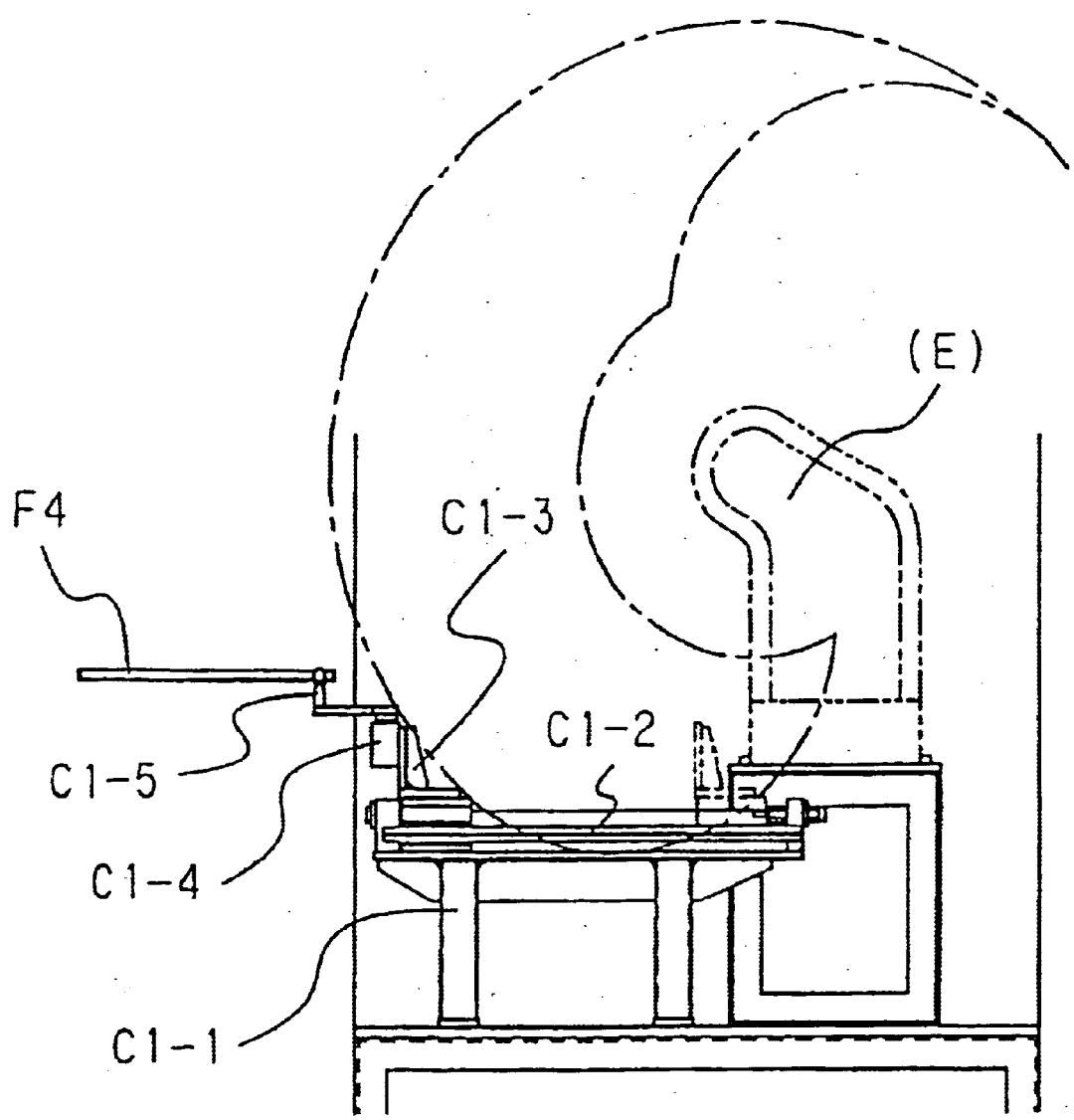
FIG. 13 is a view along the arrows M—M shown in FIG. 12.

As shown in FIG. 13 (view along the arrows M—M shown in FIG. 12), the work base retrieval and storage device C1 comprises a stand C1-1; a horizontally movable cylinder C1-2; a supporting frame C1-3; a cylinder C1-4 for raising and lowering; and a pin C1-5. With the ascent of said cylinder C1-4 for raising and lowering, said pin C1-5 can be lowered into a gap in a handle of the work palette F4, the work base (F) can be removed from the work stocker (B) and brought to the work manipulation table (C) and then removed from the work manipulation table (C) and stored in the work stocker (B).

As shown in FIG. 7 (view along the arrows M—M shown in FIG. 5), the device C2 for grasping and raising or lowering the solution container comprises a vertical-use cylinder C2-1 for raising and lowering provided on the table C13 for manipulating the solution to be placed on the work base; a solution container support tray C2-2; a horizontally movable cylinder C2-3; and a grasping hook C2-4. When a solution container F1-4 is brought to the device C2 for grasping and raising or lowering the solution container by the work manipulation robot (E), the grasping hook C2-4 is closed by the operation of the horizontally movable cylinder C2-3, the cap portion of the solution container F1-4 is grasped, the vertical-use cylinder C2-1 descends and the solution suction needle F8-1 attached to the solution suction needle stand F6 is inserted in the cap.

Figure 14:
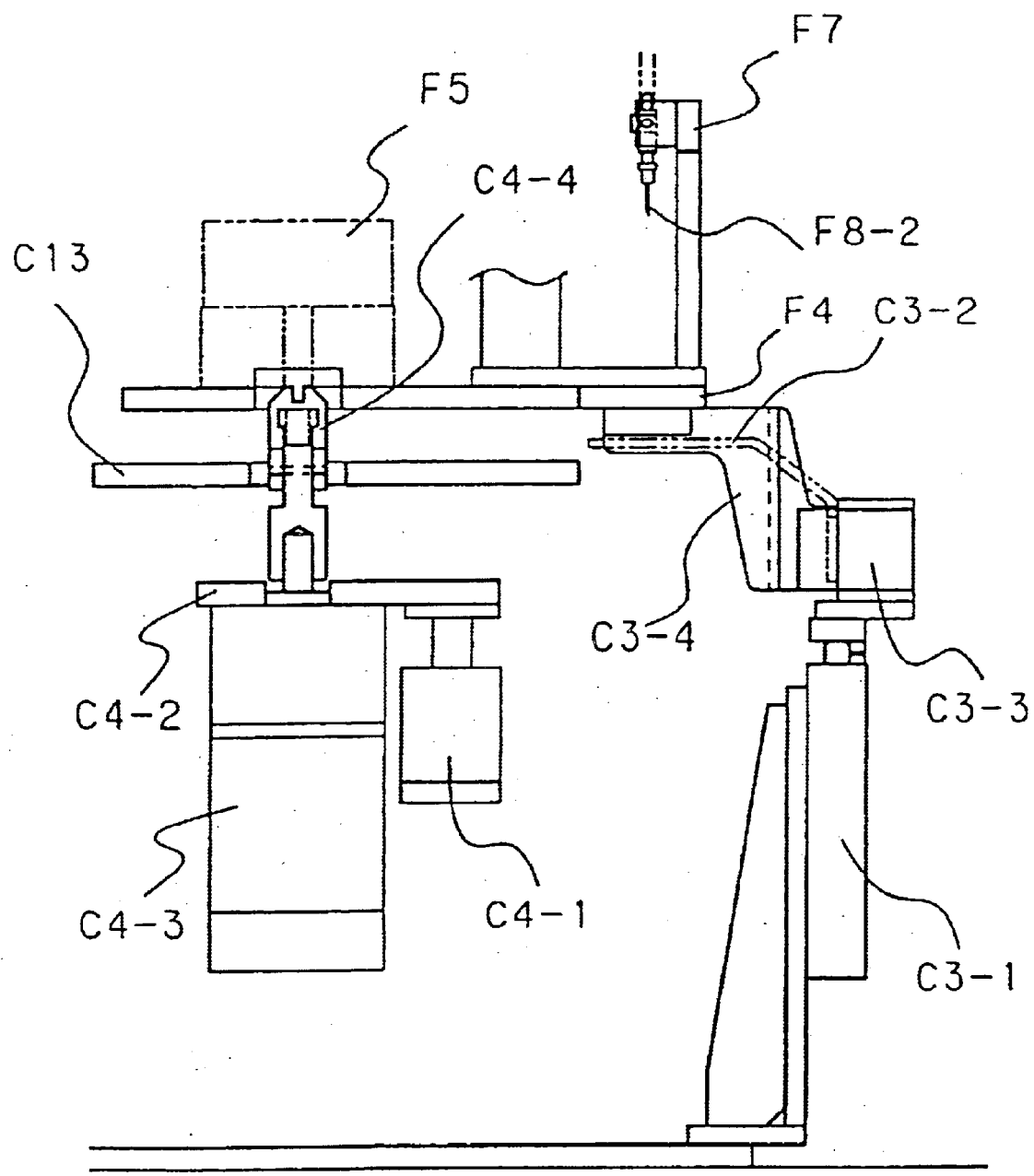
FIG. 14 is a view along the arrows N—N shown in FIG. 5.

As shown in FIG. 14 (view along the arrows N—N shown in FIG. 5), the device C3 for grasping and raising a specimen container is provided on the table C13 for manipulating the solution to be placed on the work base and comprises a vertical-use cylinder C3-1 for raising and lowering; a specimen container support base C3-2; a horizontally movable cylinder C3-3 and a grasping hook C3-4. When a specimen container F1-4 is brought to the device C3 for grasping and raising the specimen container by the work manipulation robot (E), the grasping hook C3-4 is closed by the operation of the horizontally movable cylinder C3-3, the body of the specimen container F1-1 is grasped, the vertical-use cylinder C3-1 ascends and the solution injection needle F8-2 attached to the solution injection needle stand F7 is inserted in the cap of the specimen container F1-1.

As shown in FIG. 14, the solution transport pump rotating device C4 comprises a vertical-use cylinder C4-1 provided on the table C13 for manipulating the solution to be placed on the work base; a rotating device support base C4-2; a rotating device C4-3; and a coupling C4-4. The ascent of the vertical cylinder C4-1 brings the coupling C4-4 into contact with the rotating axis of the solution transport pump F5, thus causing the solution transport pump F5 to rotate.

Figure 15:
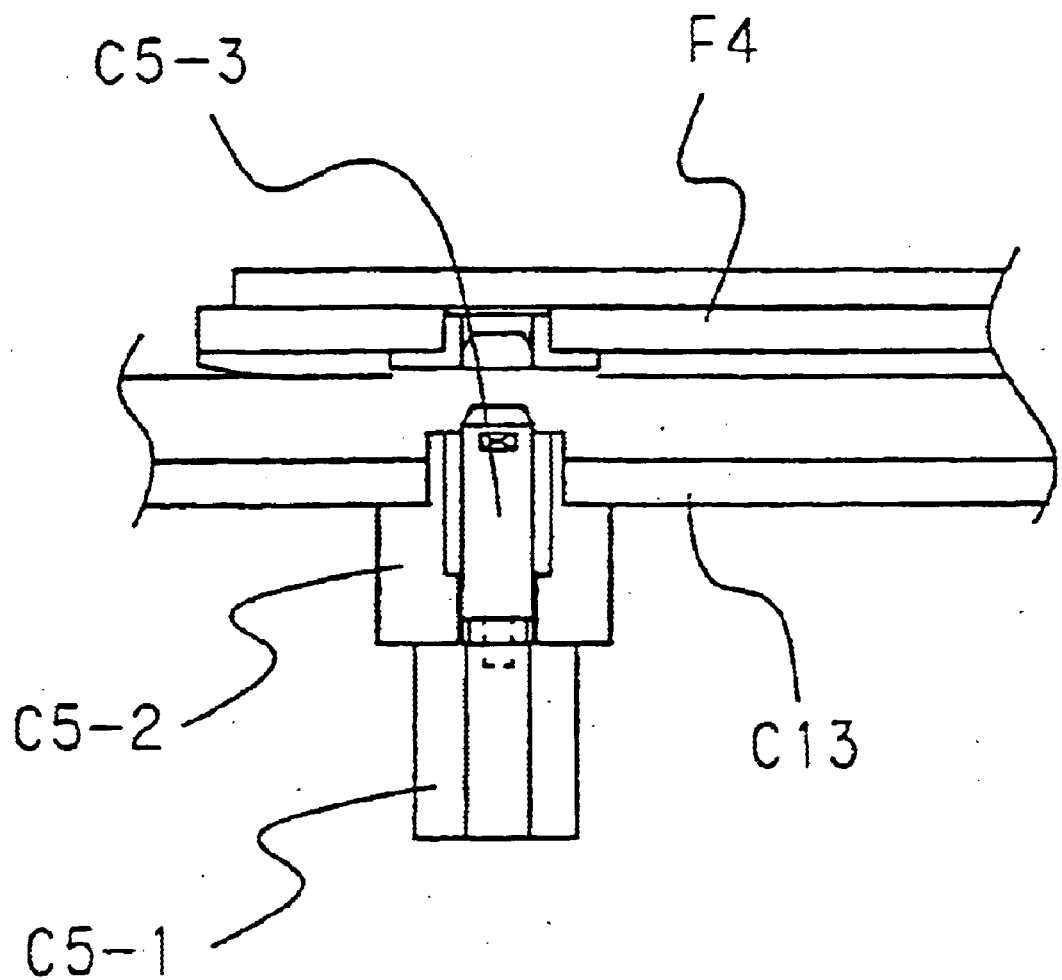
FIG. 15 is a cross-sectional view along the line N—N.

As shown in FIG. 15 (cross-sectional view along the line N—N of FIG. 12), the first work base position determining device C5 comprises a vertical-use cylinder C4-1 provided on the table C13 for manipulating the solution to be placed on the work base; a cylinder base C5-2; and a work base insertion pin C5-3. The ascent of the vertical cylinder C5-1 inserts the work base insertion pin C5-3 into a hole previously provided on the work palette and activates the work base position determining device at the same time as it activates a second work base position determining device C12 (to be described later) to determine and fix the position of the work base.

As shown in FIG. 10 (view along arrows M—M shown in FIG. 8), a device C6 for grasping and raising or lowering a variety of solution containers comprises a vertical cylinder C6-1 provided on the table C14 for manipulating a variety of solutions to be placed on the work base; a container support tray C6-2; a horizontally movable cylinder C6-3; and a grasping hook C6-4. When a variety of solution containers is brought to said device C6 for grasping and raising or lowering a variety of solution containers by the work manipulation robot (E), the grasping hook C6-4 is closed by the operation of the horizontally movable cylinder C6-3, the cap portion of said variety of solution containers is grasped, the vertical cylinder C2-1 descends and the solution suction needle F14-1 attached to the solution injection needle stand F10 is inserted in the cap of the solution container.

As shown in FIG. 10, the device C7 for aiding in removing the cap from the various-solution suction needle comprises a support C7-1 provided on the table C14 for manipulating a variety of solutions to be placed on the work base; a horizontally movable cylinder C7-2; and a hook C7-3 attached to a robot edge. This device is intended to make it easier to remove the suction needle cap when using the work manipulation robot (E), by loosening the suction needle cap 14-7 covering the solution suction needle F14-1 attached to the solution suction needle stand F10 prior to beginning operation. Said device C7 for aiding in removing the cap from the various-solution suction needle is not needed if the removal of said suction needle cap F14-7 can be done easily.

Figure 11:
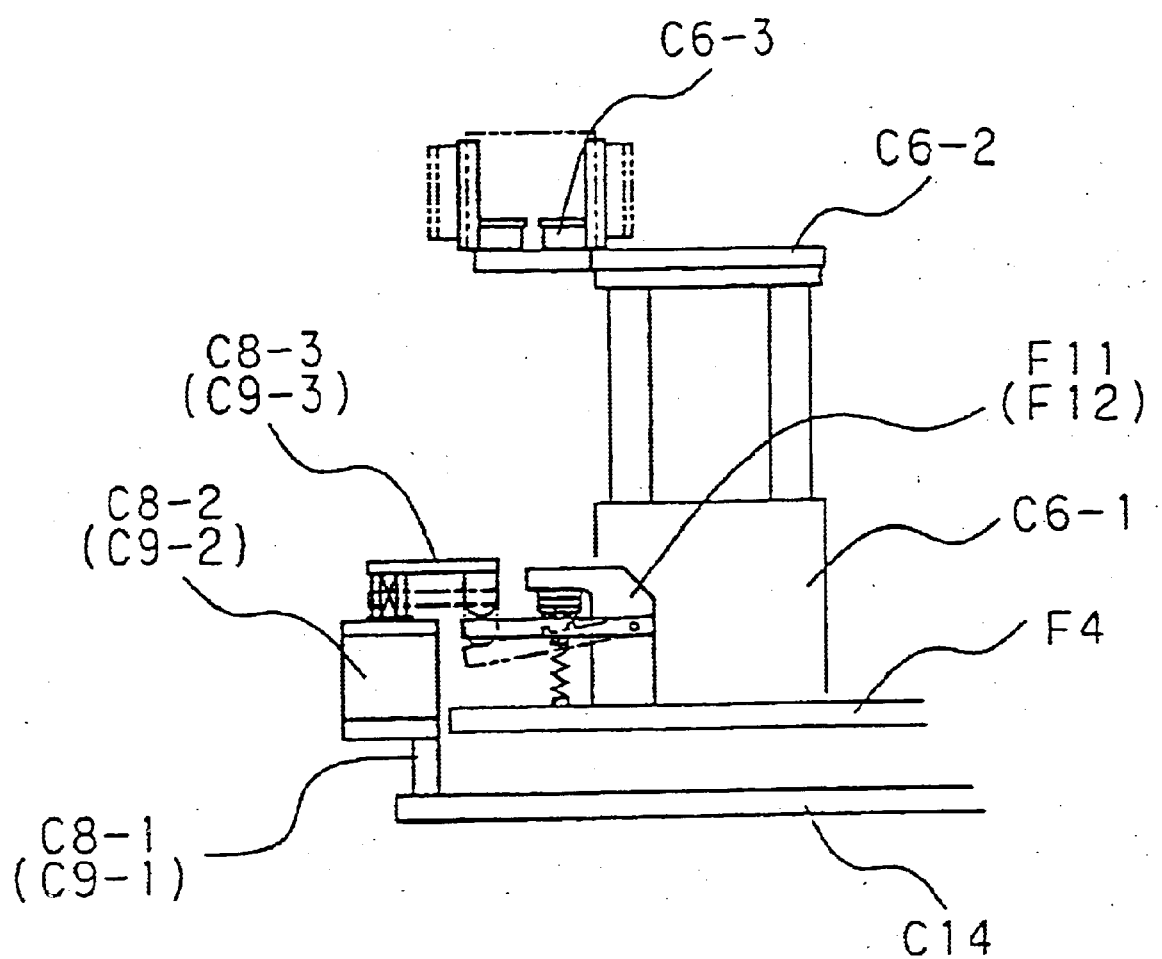
FIG. 11 shows a side view of a pinch valve.

As shown in FIG. 10 and FIG. 11, the first pinch valve operating device C8 comprises a support C8-1 provided on the table C14 for manipulating a variety of solutions to be placed on the work base; a vertical-use cylinder C8-2; and a valve push rod C8-3, with the ascent and descent of said valve push rod C8-3 opening and closing the first pinch valve F11.

As shown in FIG. 10 and FIG. 11, the second pinch valve operating device C9 comprises a support C9-1 provided on the table C14 for manipulating a variety of solutions to be placed on the work base; a vertical cylinder C9-2; and a valve push rod C9-3, with the ascent and descent of said valve push rod C8-3 opening and closing the second pinch valve F11.

Figure 16:
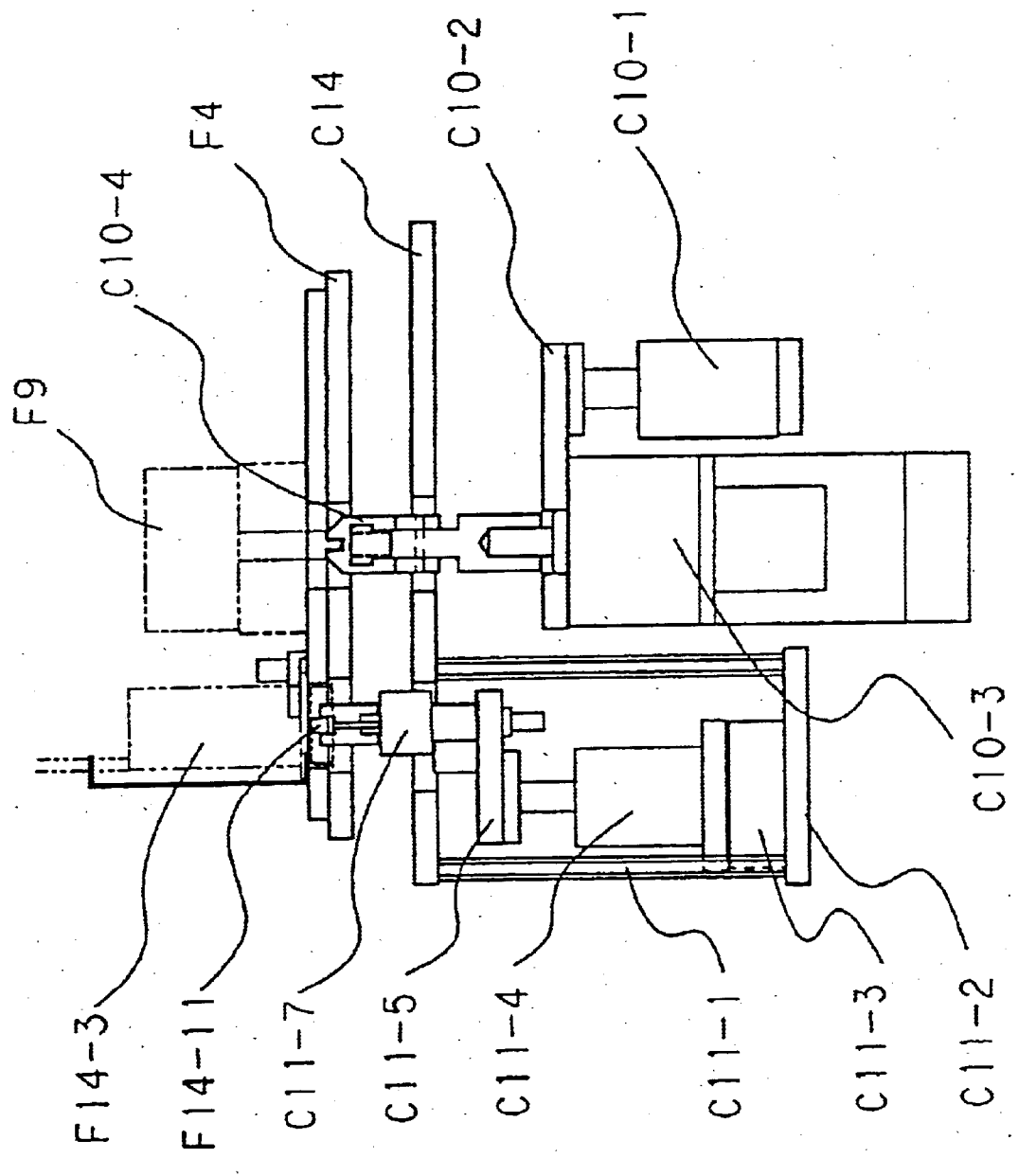
FIG. 16 is a view along the arrows N—N shown in FIG. 8.

As shown in FIG. 16 (view along the arrows N—N shown in FIG. 8), a various-solution transport pump rotating device C10 comprises a vertical cylinder C10-1 provided on the table C14 for manipulating a variety of solutions to be placed on the work base; a rotating device support base C10-2; a rotating device C10-3; and a coupling C10-4. The ascent of the vertical cylinder C10-1 brings the coupling C10-4 into contact with the rotating axis of the various-solution transport pump F9, thus causing the various-solution transport pump F9 to rotate.

Figure 17:
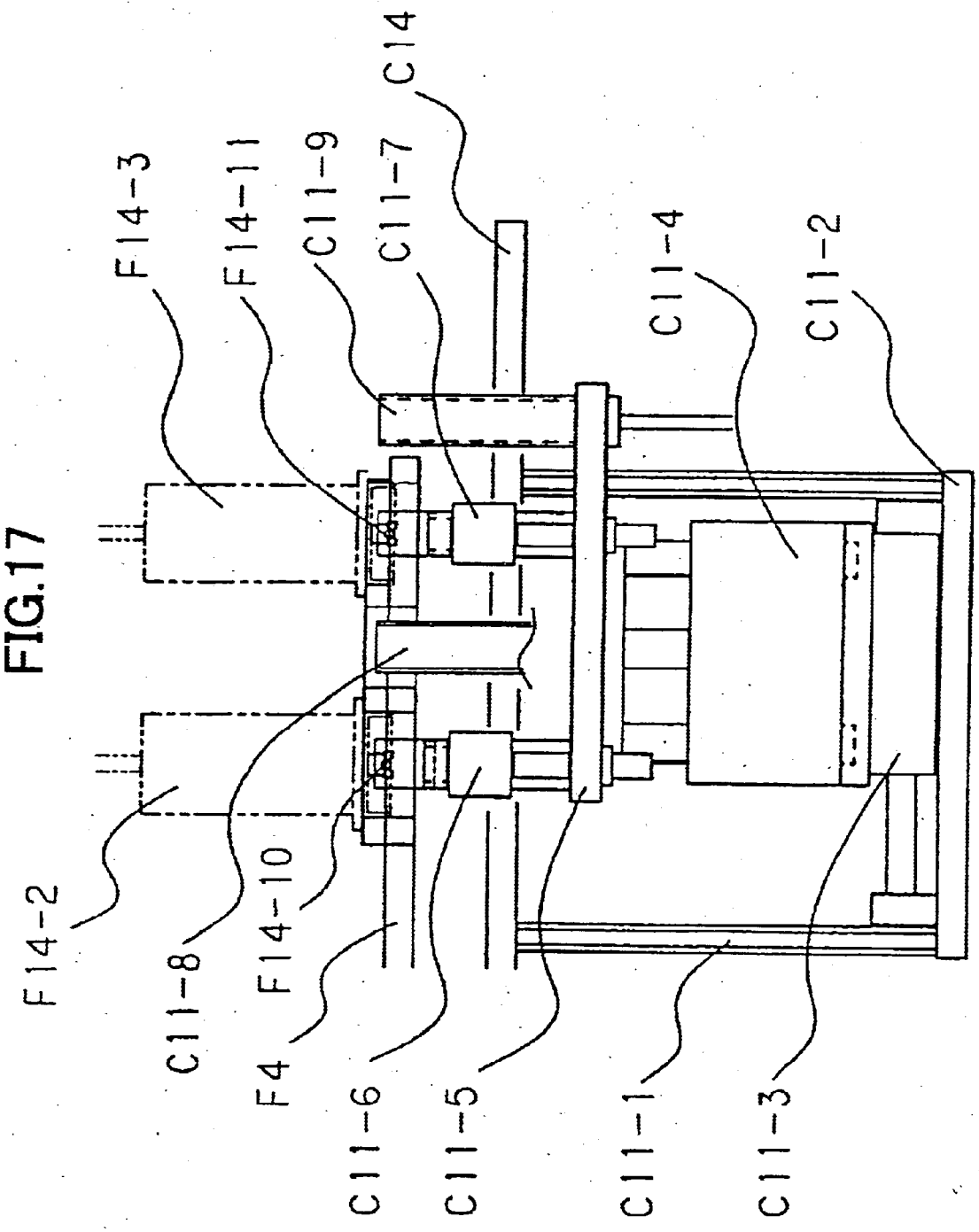
FIG. 17 is a view along the arrows P—P shown in FIG. 8.

As shown in FIG. 16 and FIG. 17 (view along the arrows P—P shown in FIG. 8), a device C11 for attaching and detaching caps to and from the bottoms of culture tubes comprises a support C11-1 provided on the table C14 for manipulating a variety of solutions to be placed on the work base; a horizontally movable cylinder base C11-2; a horizontally movable cylinder C11-3; a vertical cylinder C11-4; a base C11-5 for a device for attaching and detaching caps; a first device C11-6 for attaching and detaching a cap from the bottom of a culture tube; a second device C11-7 for attaching and detaching a cap from the bottom of a culture tube; a first drainage tube C11-8 and a second drainage tube C11-9. By operating said horizontally movable cylinder C11-3, said vertical cylinder C11-4 and said first and second devices C11-6 and C11-7 for attaching and detaching a cap to and from the bottom of a culture tube, the first bottom cap F14-10 of a first culture tube F14-2 and the second bottom cap F14-11 of a second culture tube F14-3 can be detached and stored or attached. Said first and second drainage tubes C11-8 and C11-9 come below a discharge port of said first culture tube F14-2 and a discharge port of said second culture tube F14-3 to catch the drainage when said first and second bottom caps F14-10 and F14-11 are detached and stored.

As shown in FIG. 12, the second work base position determining device C12 is of the same specifications as the first work base position determining device C5 and is mounted on the table C14 for manipulating a variety of solutions to be placed on the work base; it is operated at the same time as said first work base position determining device C5 and fixes the determined position of the work base F.

As shown in FIG. 1, an auxiliary work manipulation table (D) is provided at a position separate from that of the work manipulation table (C) within the range of possible operation of the work manipulation robot (E). Said auxiliary work manipulation table (D) is provided with equipment which can be used in common on all flasks, and it is also equipped with a temporary container placement area.

The equipment which can be used in common on all flasks and the temporary container placement area comprises common equipment and temporary placement areas required for handling the specimen to be tested, such as a solution promotion vibrating device D1; a container exchanging device D2; an ampule opening device D3; a temporary placement area for preparatory rinsing fluid containers D4; a container grasping position changing device D5; a temporary placement area for a solution suction needle cap D6; a first temporary placement area for a culture tube upper portion cap D7; a second temporary placement area for a culture tube upper portion cap D8; a temporary placement area for an auxiliary ampule injection container upper portion cap D9; a container shape confirmation sensor D10; and a temporary placement area for a solution container D11.

The solution promotion vibrating device D1 (not shown in the diagram) is a device for promoting dissolution after a powder specimen has been injected into a solution, and comprises a vibrating device main unit and an air cylinder-powered chuck attached to an upper portion of said vibrating main unit.

Figure 18:
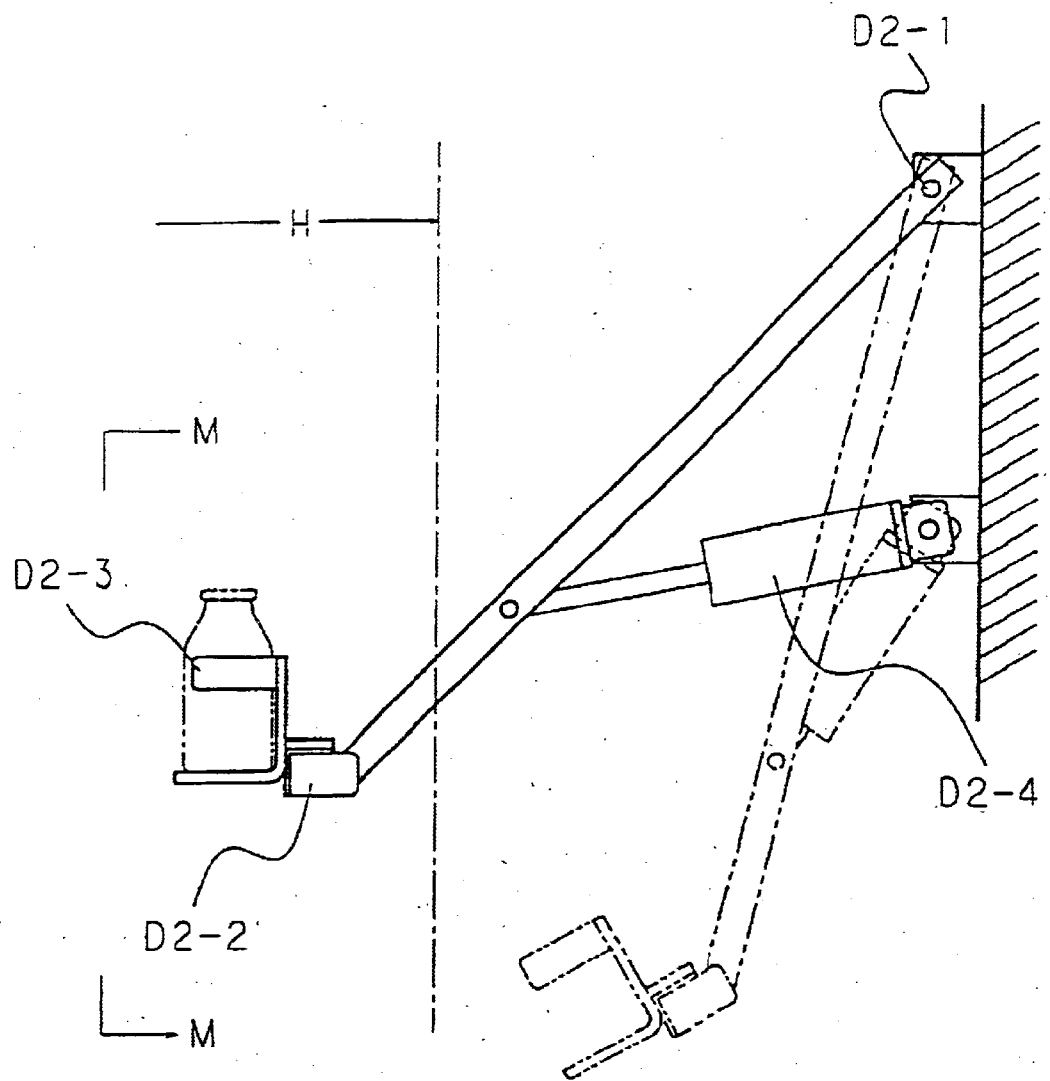
FIG. 18 shows a plan view of a container switching device.
Figure 19:
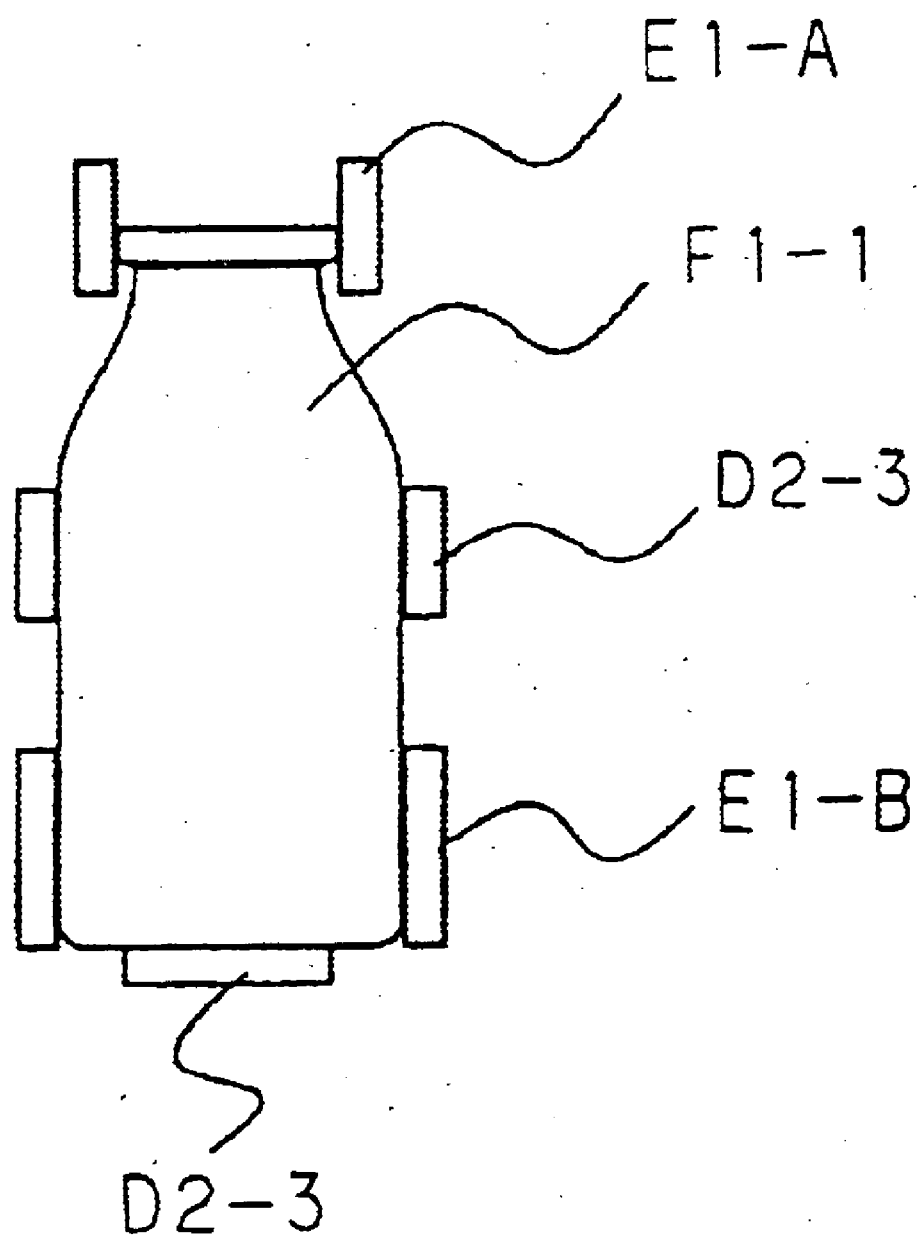
FIG. 19 is a view along the arrows M—M shown in FIG. 18.

As shown in the drawing, the container exchanging device D2 is provided on a wall surface of the robot chamber and comprises a container support axis D2-1 for a fulcrum; a swing arm D2-2; a container receiver D2-3 attached to the end of the swing arm; and a cylinder D2-4 used to retract said container receiver. As shown in FIG. 19, this device is used when changing the hold on a container from an upper portion of the container to a lower portion, or from a lower portion to an upper portion. When placed within the normal range of operation H of the robot this device would interfere with the other operations of the robot, so the retraction cylinder D2-4 is operated to store the device outside the operating range of the robot H in a position indicated by the dotted-dash lines in FIG. 18. The container receiver D2-3 is set within the operating range H of the robot as necessary.

Figure 20:
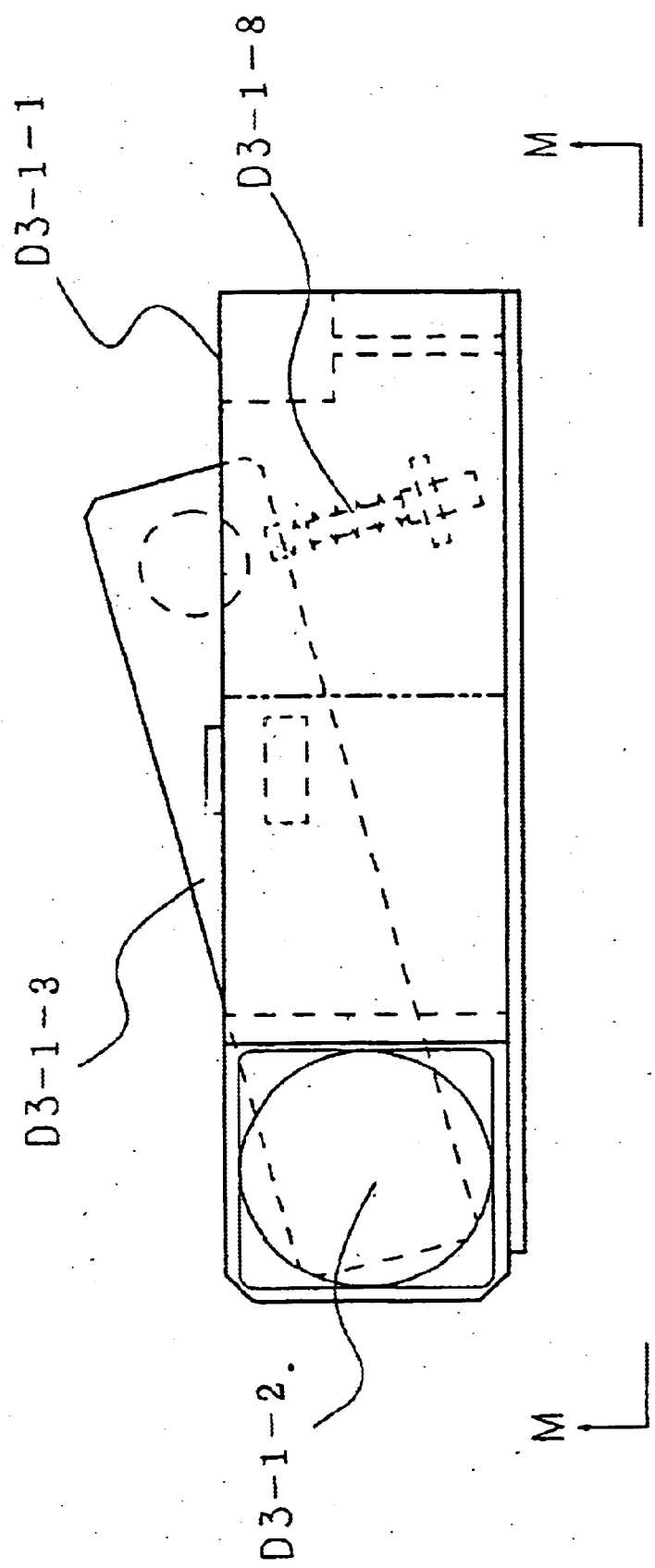
FIG. 20 shows a plan view of a device for opening ampules.
Figure 21:
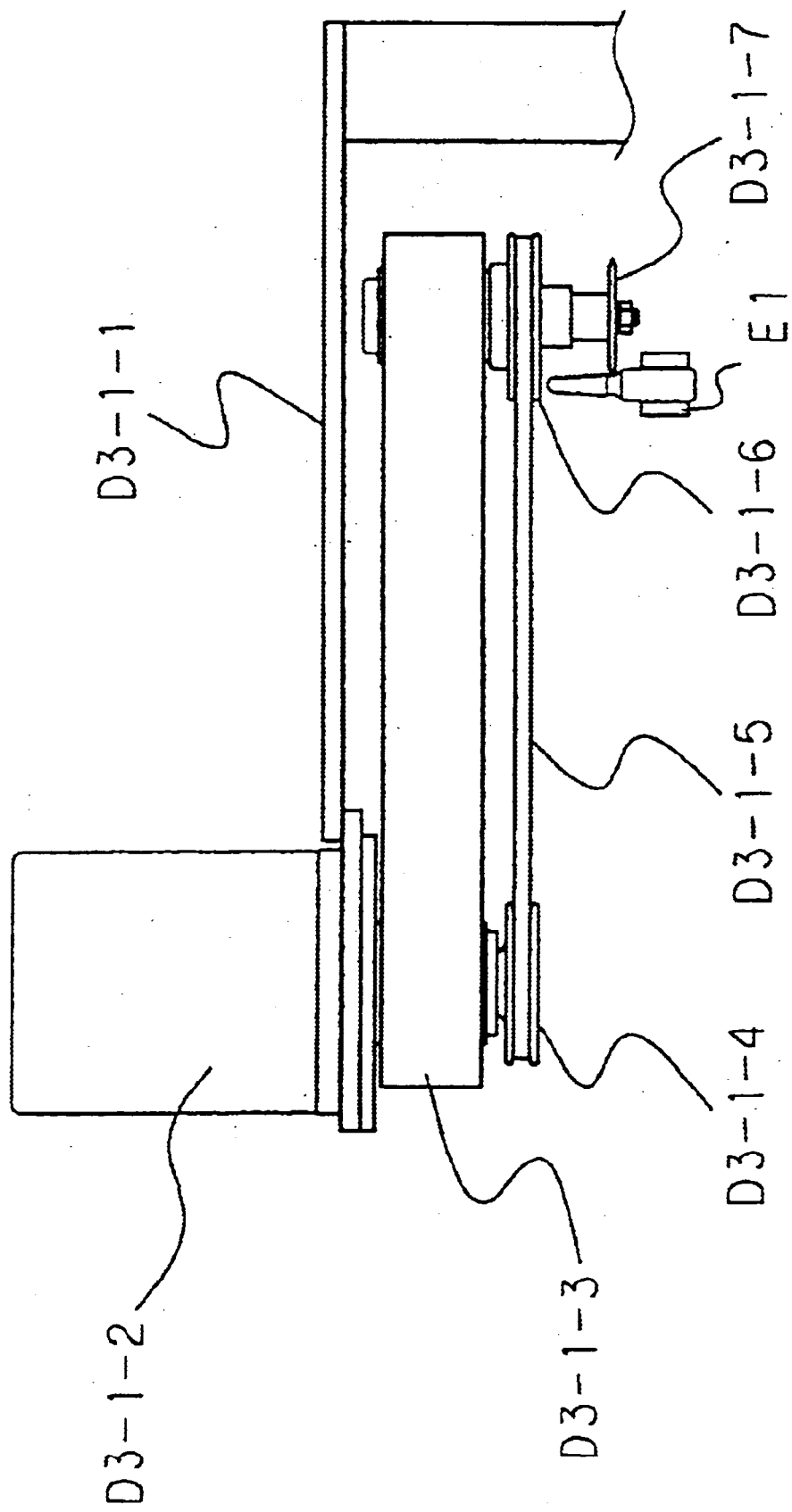
FIG. 21 is a view along the arrows M—M shown in FIG. 20.
Figure 22:
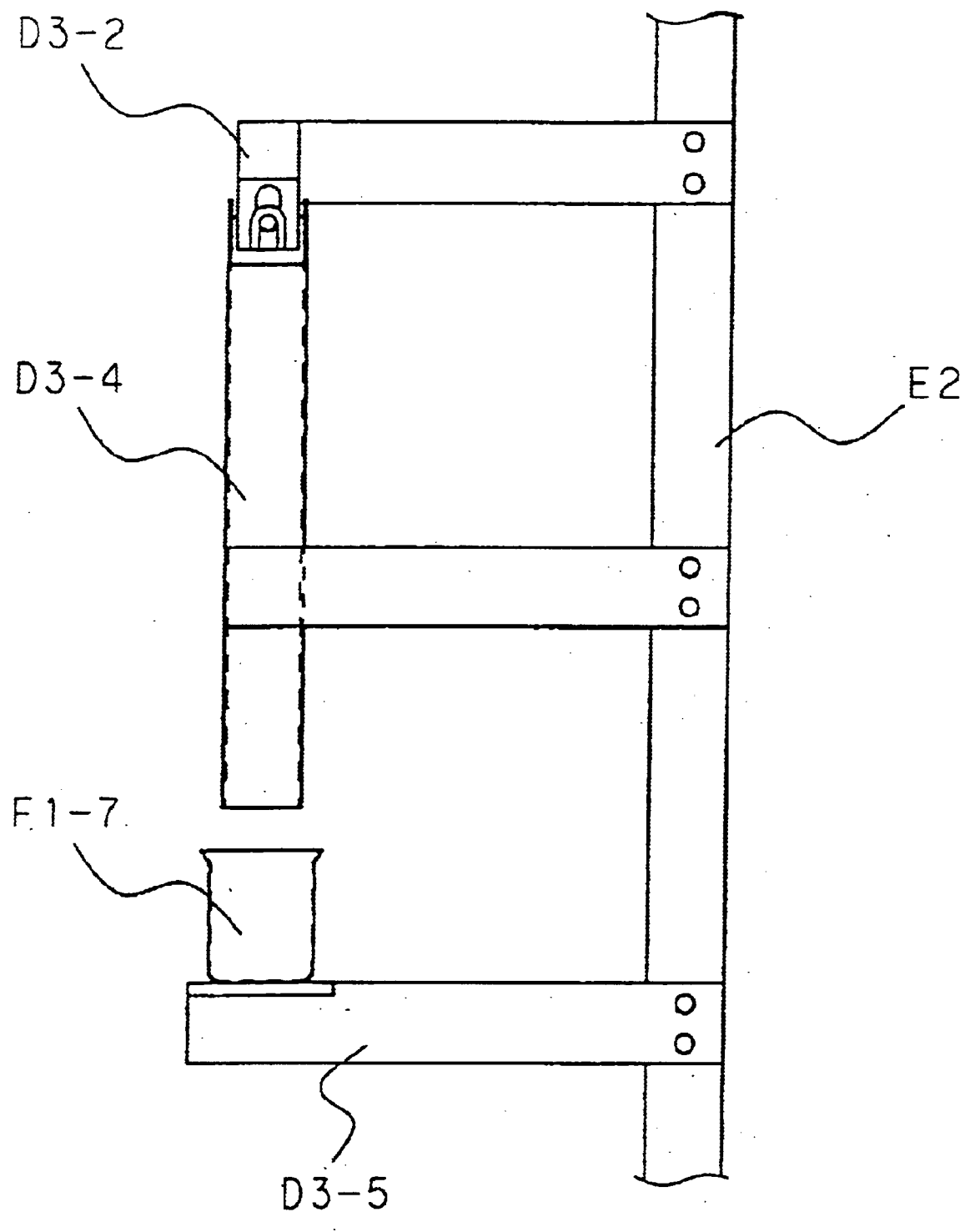
FIG. 22 is a front view of a device for collecting the broken-off neck portions of ampules.

As shown in FIG. 20 and FIG. 21, the ampule opening device D3 comprises a device for positioning the ampule so that it may be broken off at the neck, with such device itself comprising a frame D3-1-1, a motor for rotating a rotary blade D3-1-2, a revolving arm D3-1-3, a first pulley D3-1-4, a belt D3-1-5, a second pulley D3-1-6, a rotary blade D3-1-7 and a spring D3-1; an auxiliary jig D3-2 having a U-shaped groove for breaking the neck of the ampule as shown in FIG. 22; a holding position setting bar D3-3 shown in FIG. 23(H); a chute D3-4 for guiding the broken-off necks of the ampules to a collection box; and a tray for supporting a box for collecting the broken-off necks of the ampules. The work manipulation robot (E) is used to set the collection box F1-7 retrieved from the container case F1 on the collection box tray D3-5, the broken-off necks of the ampules are collected in the collection box F1-7 via the guide chute D3-4 and the box is returned to and stored in the container case F1 so as to collect waste generated in preparation of the sample with the sample itself.

As shown in FIG. 23, when the specimen container F1-1 is itself an ampule the robot hand E1 is used to exchange the ampule and change the relative position at which the ampule is grasped, after which the ampule is brought into contact with the rotary blade and notched as shown in FIG. 21, the tip portion of the ampule is inserted in the U-shaped groove of the auxiliary jig D3-2, the neck portion is twisted by the robot hand E1 and the top of the ampule is broken off at the neck.

The temporary placement area for preparatory rinsing fluid containers D4 (not shown in the diagram) is a station for the temporary placement of preparatory rinsing fluid containers when these are used in common with a plurality of samples. This device is not needed when preparatory rinsing fluid is not used in common for a plurality of samples.

The container grasping position changing device D5 (not shown in the diagram) is used as a temporary placement station when changing the position at which a variety of containers is held from the top portion of the container to either the middle body portion or the bottom portion, or from the body portion to either the top portion or the bottom portion, or from the bottom portion to either the middle body portion or the top portion, and is intended for use with comparatively small containers.

The temporary placement area for a various-solution suction needle cap D6 (not shown in the diagram) is a station for the temporary placement of the various-solution suction needle cap F14-7 from the time the cap is removed prior to operation to the time the cap is replaced after operation.

The first temporary placement area for a culture tube upper portion cap D7 (not shown in the diagram) and a second temporary placement area for a culture tube upper portion cap D7 (not shown in the diagram) are stations for the temporary placement of caps for sterile test unit upper portion exhaust ports.

The temporary placement area for the auxiliary ampule injection container upper portion cap D9 is a station for the temporary placement of the upper cap F15-3 of the auxiliary ampule injection container F15 (shown in FIG. 25) used when pressure-filtering the solution contained in the ampule container and transporting it to the sterile test unit, from the time the cap is removed prior to operation to the time the cap is replaced after operation. The upper cap F15-3 can also be put into the collection box F1-7 without being returned to its original position. The auxiliary ampule injection container upper portion cap D9 is not needed in the event that the upper cap F15-3 is put into the collection box.

Figure 24:
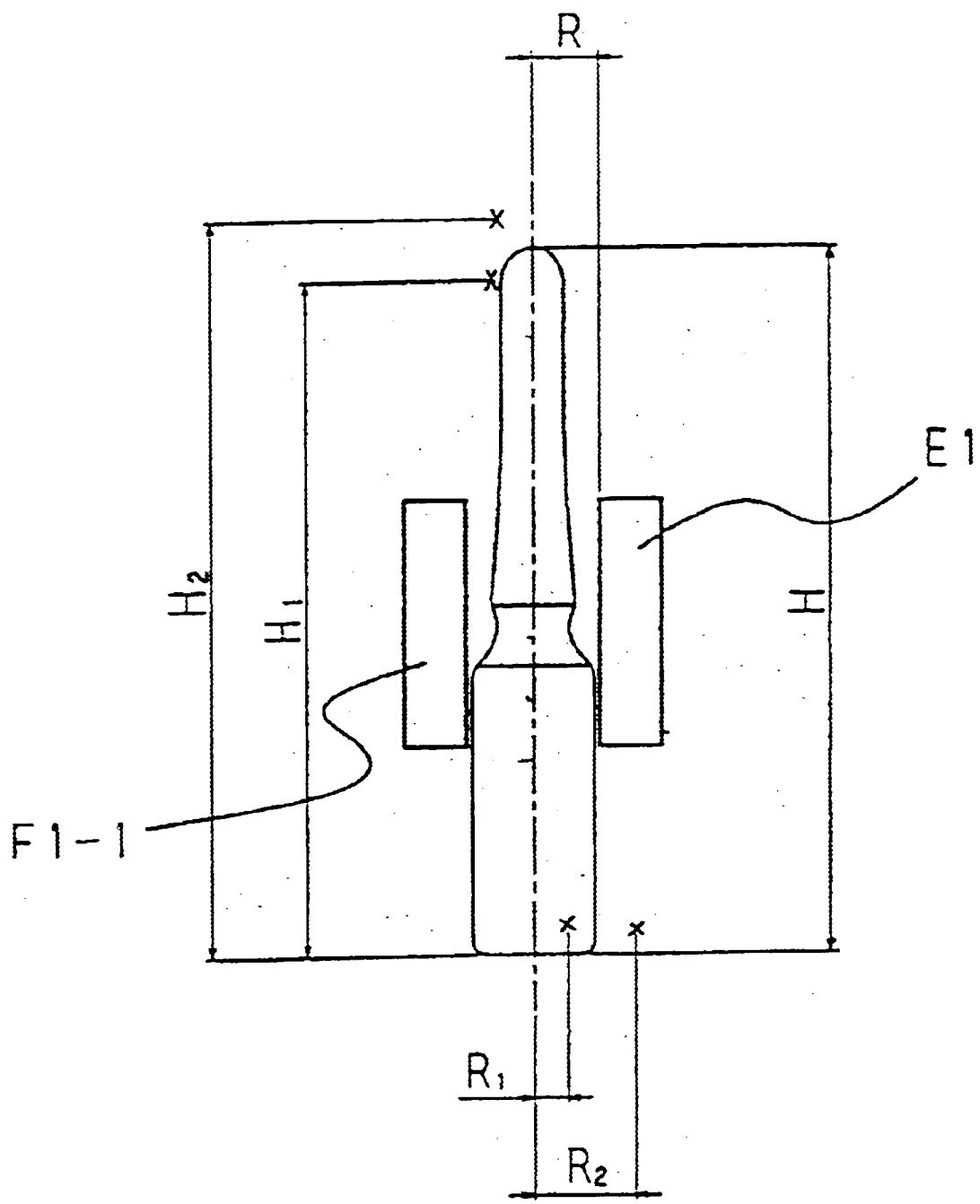
FIG. 24 is a diagram for explaining a method for ascertaining the shape of a container.

The container shape confirmation sensor D10 (not shown in the diagram) is a sensor for confirming at two points—the width and the length—that the container shape held by the work manipulation robot E is or is not of a predetermined shape; the sensor does so by bringing the container to a previously determined overhead position. As shown in FIG. 24, the sensor is programmed to include a margin of error with respect to a specimen container F1-1 of dimensions R and H as shown in FIG. 24 of R1, R2 and H1, H2; it confirms the shape of the container by sensing the presence of a container at R1 and H1 and the absence of a container at R2 and H2.

The temporary placement area for a solution container D11 (not shown in the diagram) is a station for the temporary placement of the container when the same solution container F1-4 is used for a plurality of samples. It is not needed when the same container is not used for a plurality of samples.

As shown in FIG. 1, the work manipulation table D can also be divided into several tables so long as they are within the operating range of the robot; the table need not be at one place only.

The foregoing explanation of the construction of the apparatus of the present invention assumed that the specimens to be tested were chiefly powder- or fluid-filled vials. However, as explained previously, the present invention can be adapted for use with ampules or even transfusion solution bags which are of indeterminate shape, a point which will now be explained.

Where the specimen container F1-1 is a fluid ampule, and where the neck portion of said specimen container F1-1 is broken off and the solution suction needle F14-1 of the sterile test unit F14 is inserted directly into the open neck of the container and the specimen sucked up, the following measures are required:

(1) The solution suction needle F14-1 is arranged so that it can be set above the work base facing downward.

(2) A device for grasping and raising and lowering an ampule similar to the device C3 for grasping and raising or lowering a specimen container must be added to the lower portion of the solution suction needle F14-1.

(3) The length of the solution suction needle F14-1 must be matched to the size of the deepest specimen container F14-1.

However, even with the application of these modifications there is still a choice to be made between two types of sterile test units F14 when setting the solution suction needle F14-1 to the work base, the solution suction needle stand F10 becomes even more complicated, a very long solution suction needle F14-1 would have to be used depending on the size of the container and the solution suction needle F14-1 of a chosen length would then become unusable if the containers came to be even larger. There is thus a problem with respect to the operability, the cost of equipment, the reliability of the equipment (i.e., the accuracy of extractions with a long needle) and its flexibility with respect to the stability of supply of said equipment and any specification changes thereto (such as changes in the sizes of specimen containers).

Figure 25:
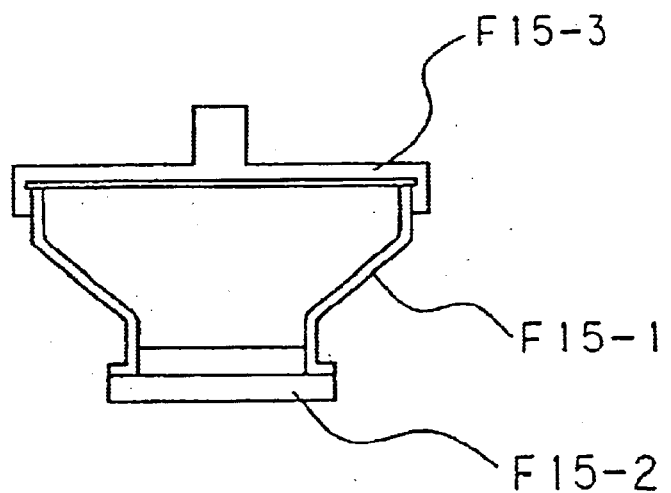
FIG. 25 shows the construction of an auxiliary ampule injection container.

In place of the above-mentioned measures the present invention uses the auxiliary ampule injection container F15 shown in FIG. 25 to resolve the foregoing problems. That is, said auxiliary ampule injection container F15, which as shown in said FIG. 25 comprises an auxiliary ampule injection container main body F15-1; an auxiliary ampule injection container lower portion cap F15-2 (a cap of approximately the same specifications as the vial container) attached to the lower portion of said auxiliary ampule injection container main body F15-1 for inserting said solution suction needle F14-1; and the upper cap F15-3 covering the upper portion to keep the machinery secret. By pouring all the ampule solvent into said auxiliary ampule injection container F15 the specimen can be handled in the same way that a fluid-filled vial is handled.

Figure 26:
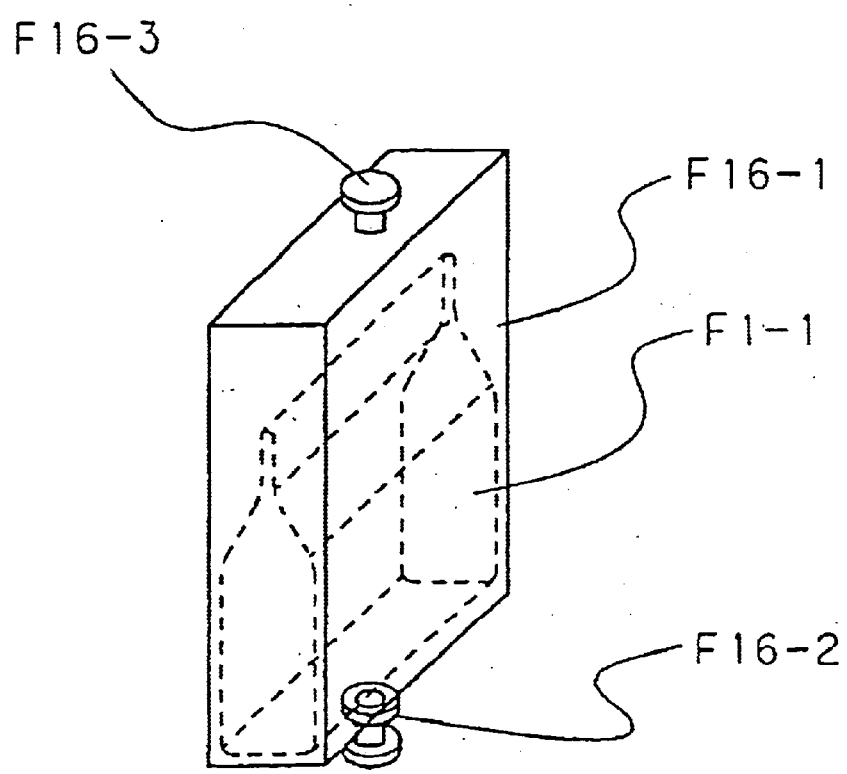
FIG. 26 shows the construction of a transfusion solution bag fixing container.

In addition, where the specimen container F1-1 is a container of indeterminate shape and a large suction hole as shown in FIG. 26 a fixed container for indeterminate-shape containers F16 is available, into which said specimen container F1-1 is placed in its entirety. This fixed container for indeterminate-shape containers F16 comprises a fixed container main body F16-1 for indeterminate-shape containers; a fixed container cap fixing portion F16-2 for indeterminate-shape containers; and a fixed container robot hand suspension portion F16-3 for indeterminate-shape containers.

That is, the specimen container F1-1 is placed inside this fixed container for indeterminate-shape containers F16 and this fixed container is then loaded into the container case F-1, to enable the sample to be handled in the same way that a fluid-filled vile is handled.

A specimen container F1-1 that is itself of indeterminate shape like a plastic bag does not permit the solution injection tube unit F-8 shown in FIG. 6 for taking in outside air during suction to perform its function.

Figure 27:
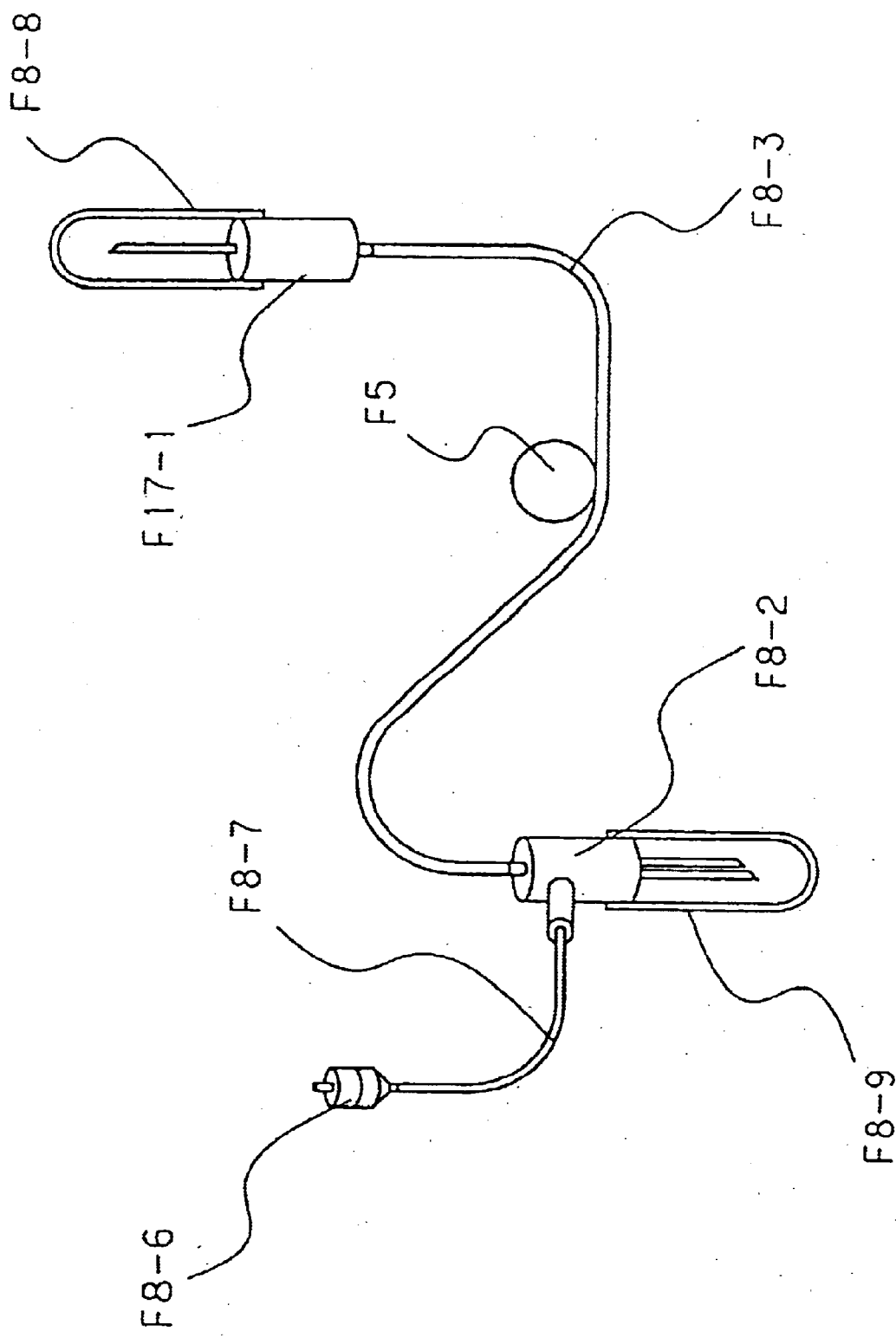
FIG. 27 shows the construction of a tube unit for injecting containers of indeterminate shape.

As shown in FIG. 27, the present invention provides an indeterminate-shaped container injection tube unit F17 that has the same specifications as the solution injection tube unit F8 except that it has a single indeterminate-shaped container suction needle F1 with no filter attached on the suction side. That is, said indeterminate-shaped container injection tube unit F17 is already installed on the solution injection pump unit F2, said indeterminate-shaped container fixed container F16, which has a built-in specimen container F1-1 in place of the solution container F1-4, is installed on the device C2 for grasping and raising or lowering the solution container, empty vial containers are positioned in the device C3 for grasping and raising or lowering a specimen container, the same operations as those performed with a solution injection are carried out and, after the solution in said specimen container F1-1 is all poured into said vial container, said container is positioned at the device C6 for grasping and raising or lowering a variety of solution containers and is ready for manipulation.

In the aforementioned manner the apparatus of the present invention can be adapted not only to use with vials but also with containers of various shapes and sizes, such as ampules, transfusion solution bags and eye-dropper bottles.

Figure 28:
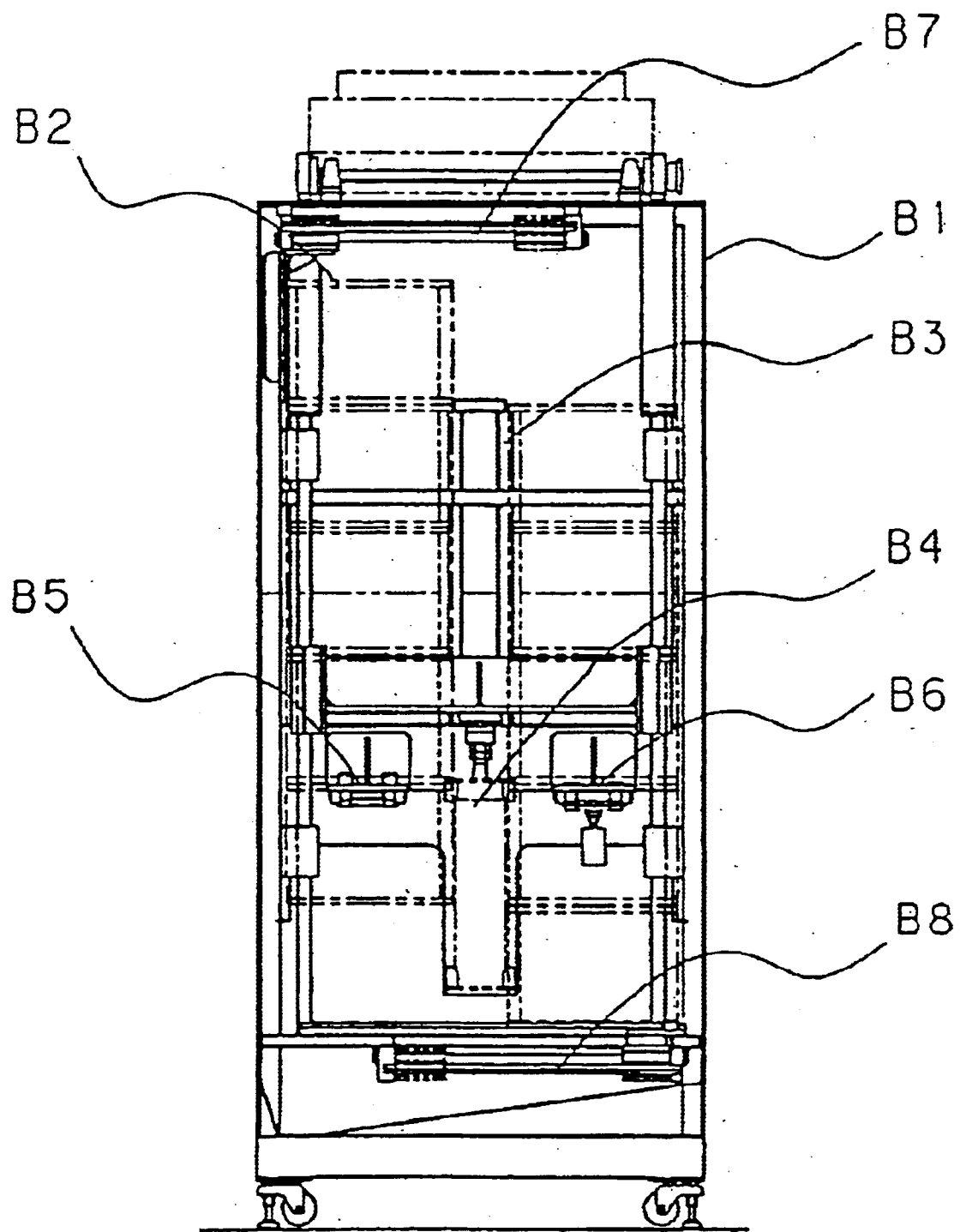
FIG. 28 shows a front view of a work stocker.

As shown in FIG. 28 (front view of a work stocker), the work stocker (B) comprises a main framework B1; a circulating frame B2 for storing and circulating the work bases F (in this diagram 10 trays) inside said work stocker (B); a circulating frame guide B3 so that the trays do not stray from the route when circulated; a device B4 for raising and lowering the circulating frame B2 together with the work bases F stored therein; an ascending portion circulating frame support device B5 for continuously supporting the circulating frame B2 on the ascending side; a descending portion circulating frame support device B6 for supporting the circulating frame B2 that is second from the bottom of the circulating frame B2 on the descending side when said device B4 for raising and lowering the circulating frame B2 descends; a device B7 for moving to the side an upper portion circulating frame, for laterally moving the circulating frame B2 that is on the highest step on the ascending side to the highest step on the descending side; and a device B8 for moving to the side a lower portion circulating frame, for laterally moving the circulating frame B2 that is on the lowest step on the descending side to the lowest step on the ascending side. Each and every one of these devices is operated so as to permit the circulating frame B2 to circulate.

Figure 29:
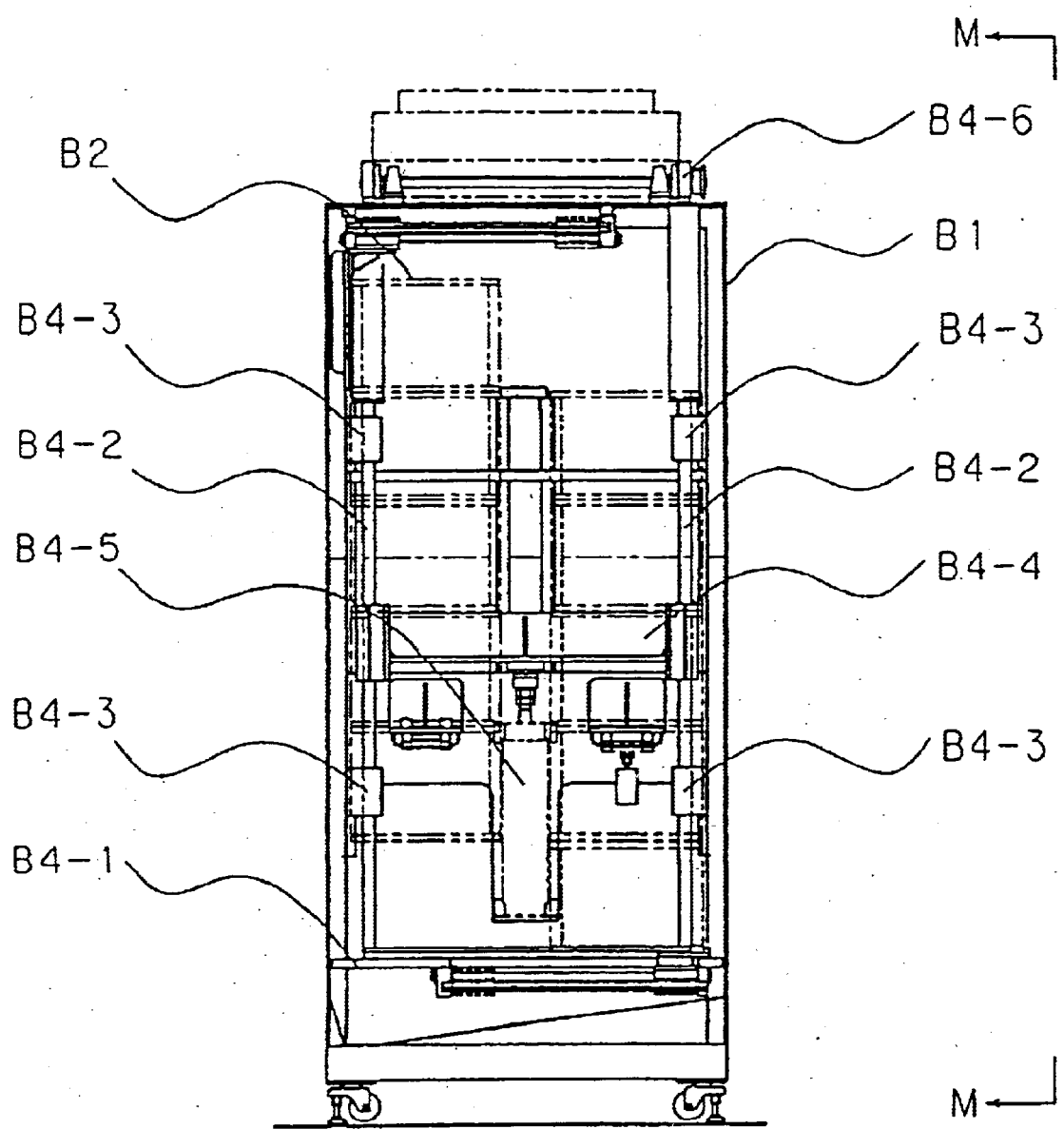
FIG. 29 shows a front view of a device for raising and lowering the circulating frame.
Figure 30:
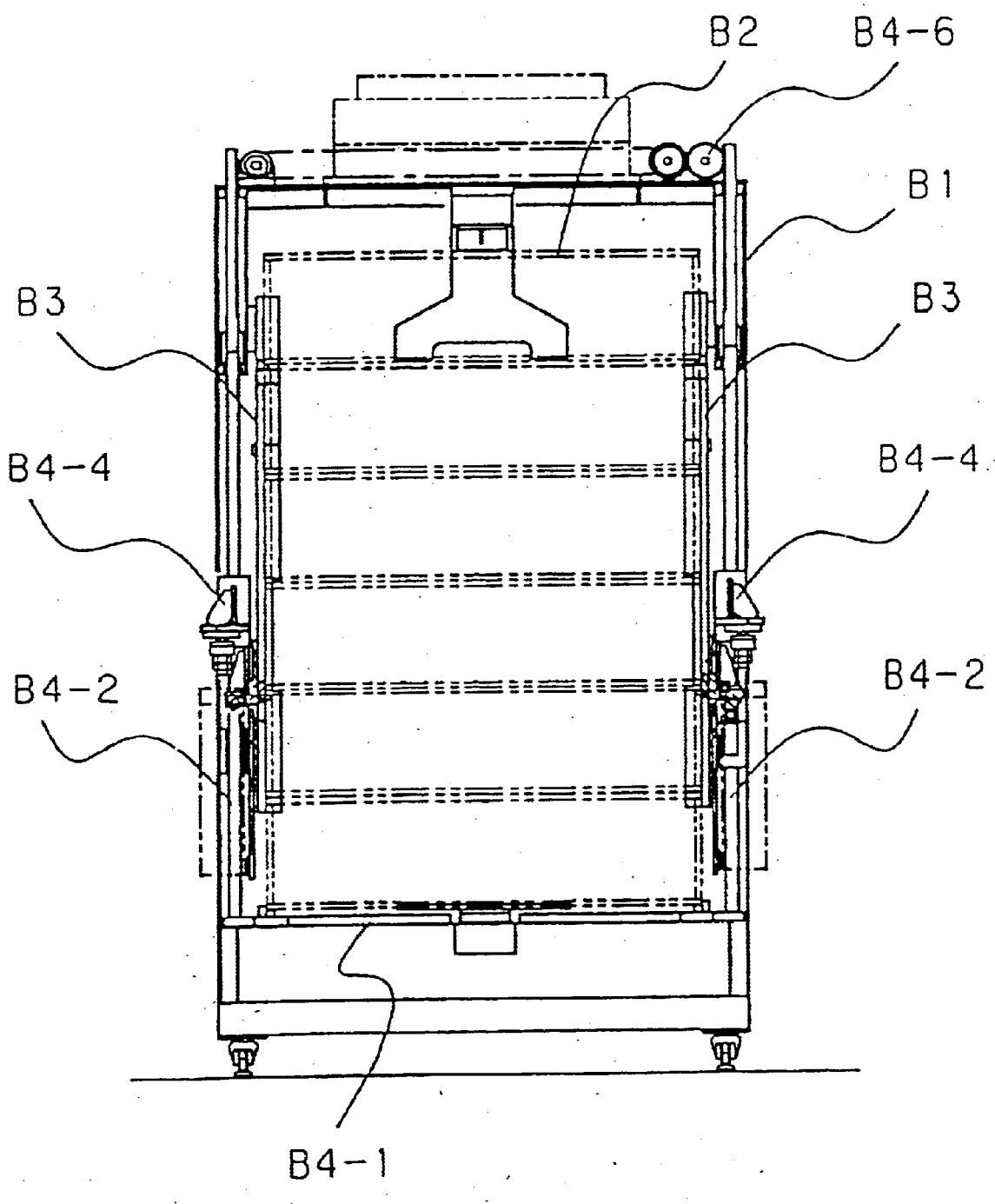
FIG. 30 is a view along the arrows M—M shown in FIG. 29.

As shown in FIG. 29 (front view of a device B4 for raising and lowering a circulating frame) and FIG. 30 (view along the arrows M—M shown in FIG. 29), the device B4 for raising and lowering the circulating frame comprises a base B4-1 for the raising and lowering device; a vertical axle B4-2; a vertical axle bearing B4-3; a vertical arm B4-4; a vertical cylinder B4-5; and a device B4-6 for synchronizing the ascent and descent of the four vertical axles so that they all operate together at the same time. The base B4-1 for the raising and lowering device ascends and descends by operation of the vertical cylinder B4-5.

Figure 31:
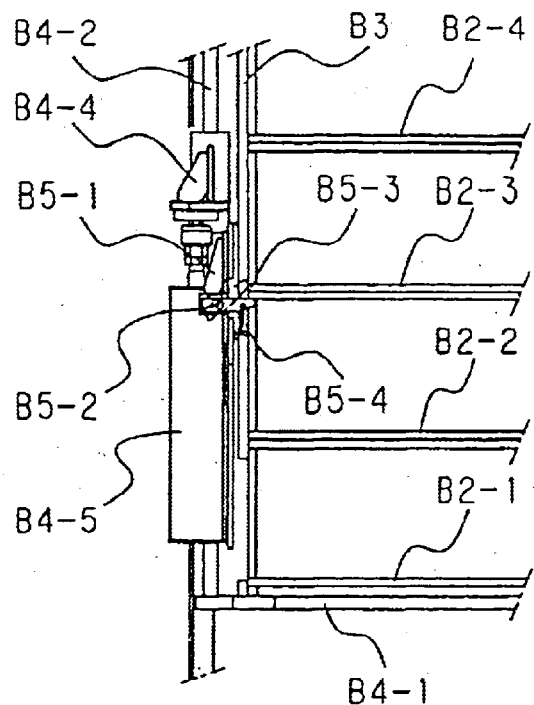
FIG. 31 shows a front view of an ascending portion circulating frame support.

As shown in FIG. 31 (front view of an ascending portion circulating frame support), an ascending portion circulating frame support device B5 comprises an ascending portion circulating frame support device mounting base B5-1; a rotating axle B5-2; a hook B5-3; and a spring B5-4. When the base B4-1 for the raising and lowering device ascends the circulating frame B2-2 is pushed upward by the lower-step circulating frame B2-1, the hook B5-3 automatically releases and a supporting portion of the lower-step circulating frame B2-1 passes the hook B5-3, at which point the hook B5-3 is returned to its original position by the spring B5-4 so that the circulating frame B2-1 is supported by the hook B5-1 even when the base B4-1 for the raising and lowering device descends and the position once occupied by the circulating frame B2-2 is refilled by circulating frame B2-1.

Figure 32:
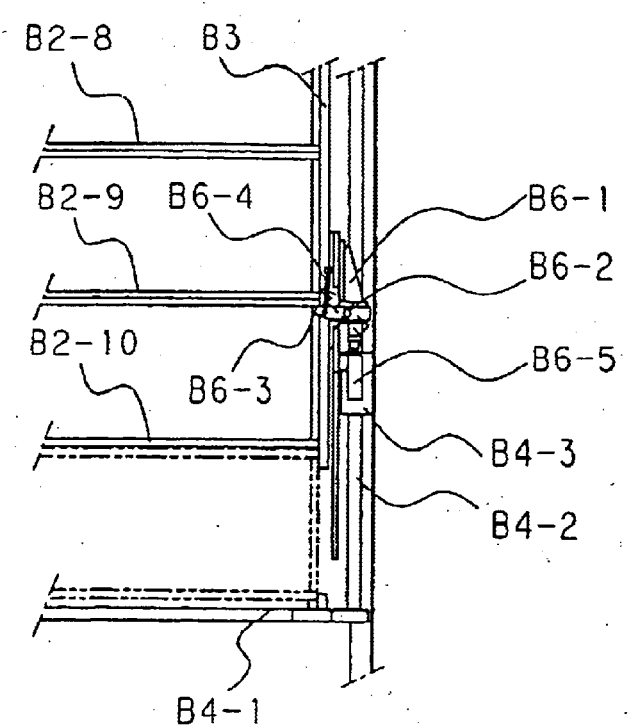
FIG. 32 shows a front view of a descending portion circulating frame support device.

As shown in FIG. 32 (front view of a descending portion circulating frame support device), a descending portion circulating frame support device B6 comprises a descending portion circulating frame support device mounting base B6-1; a rotating axle B6-2; a hook B6-3; a spring B6-4; and a hook release cylinder B6-5. When the base B4-1 for the raising and lowering device ascends a circulating frame B2-10 is lifted upward the hook release cylinder B6-5 is engaged and the hook B6-3 is released from its supporting position. The base B4-1 for the raising and lowering device begins to descend and the supporting portion of the circulating frame B2-10 and a needle on a lower side of a circulating frame B2-9 on an upper step of the circulating frame B2-10 pass the hook portion B6-3, at which time the hook release cylinder B6-5 is engaged and the hook B6-3 supports the circulating frame B2-9, the circulating frame B2-10 is let go and the base B4-1 for the raising and lowering device descends.

Figure 33:
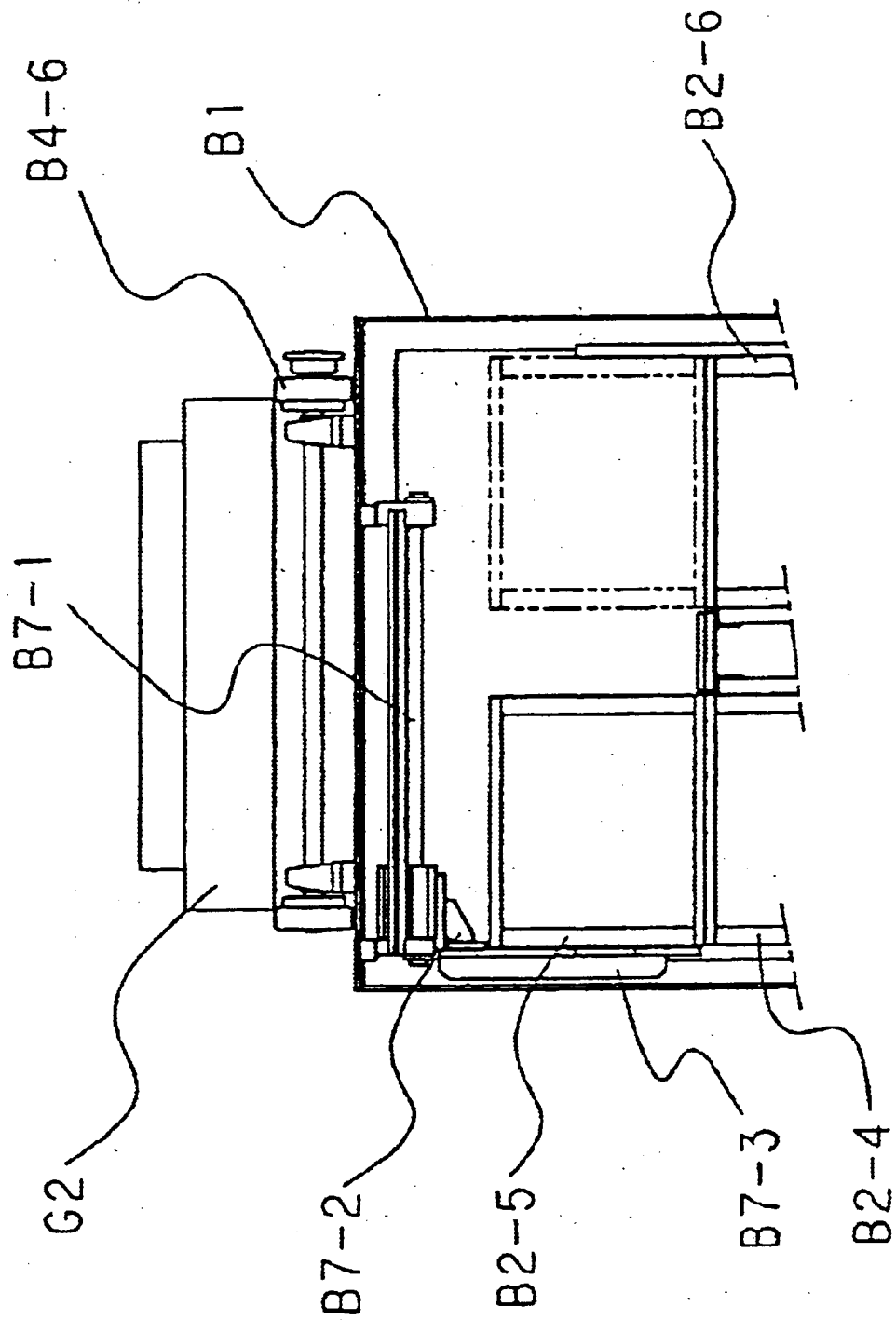
FIG. 33 shows a side view of a device for laterally moving an upper portion circulating frame.

As shown in FIG. 33 (side view of a device for laterally moving an upper portion circulating frame), a device B7 for laterally moving an upper portion circulating frame comprises a cylinder B7-1 for laterally moving an upper portion circulating frame mounted inside a chamber on an upper portion of the main frame unit B1; a push-plate support B7-2; and a push-plate B7-3. By engaging the cylinder B7-1 for laterally moving an upper portion circulating frame the circulating frame B5-2 on the uppermost step of the ascending line (the uppermost step on the left in the diagram) is moved to the uppermost step on the descending line (the uppermost step on the right in the diagram).

Figure 34:
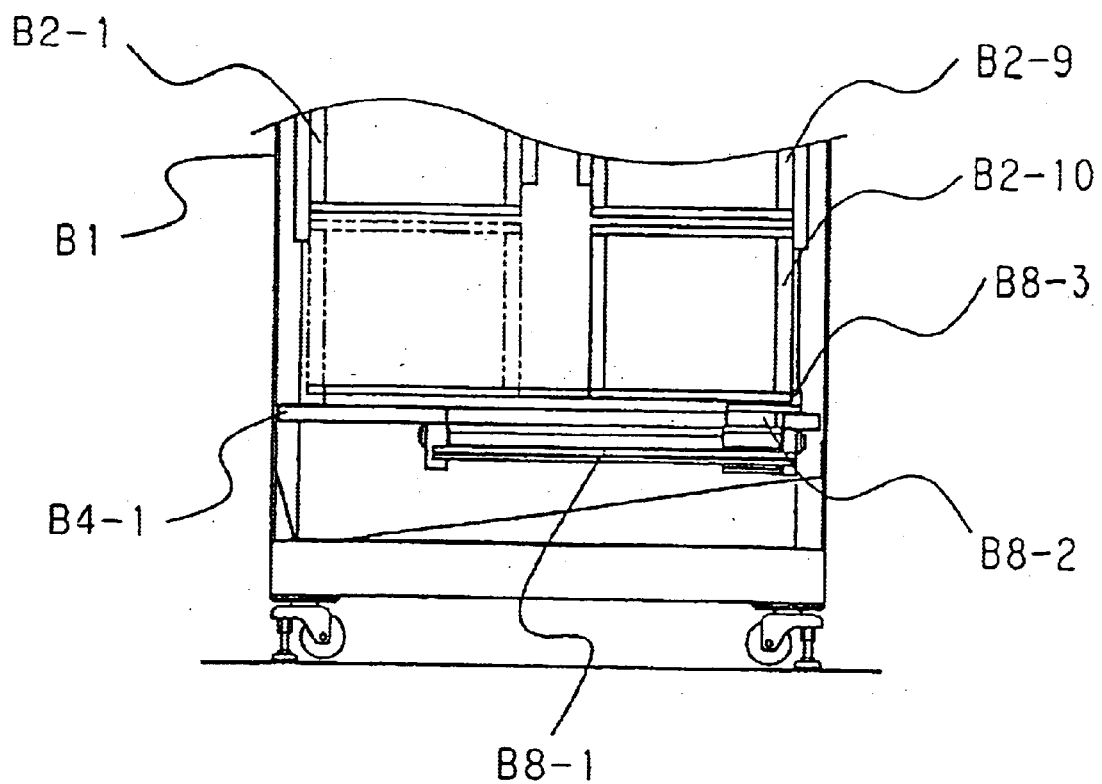
FIG. 34 shows a side view of a device for moving laterally a lower portion circulating frame.

As shown in FIG. 34 (a side view of a device for moving laterally a lower portion circulating frame), a device B8 for moving laterally a lower portion circulating frame comprises a cylinder B8-1 for laterally moving a lower portion circulating frame mounted on the base B4-1 for the raising and lowering device; a push-plate support B8-2; and a push-plate B8-3. By engaging the cylinder B8-1 for laterally moving a lower portion circulating frame the circulating frame B2-10 on the lowermost step of the descending line (the lowermost step on the right in the diagram) is moved to the uppermost step on the descending line (the lowermost step on the left in the diagram). In the diagram the cylinder B8-1 for laterally moving a lower portion circulating frame is shown mounted on the base B4-1 for the raising and lowering device, but said cylinder B8-1 for laterally moving a lower portion circulating frame can also be mounted on the main frame unit B1.

Figure 55:
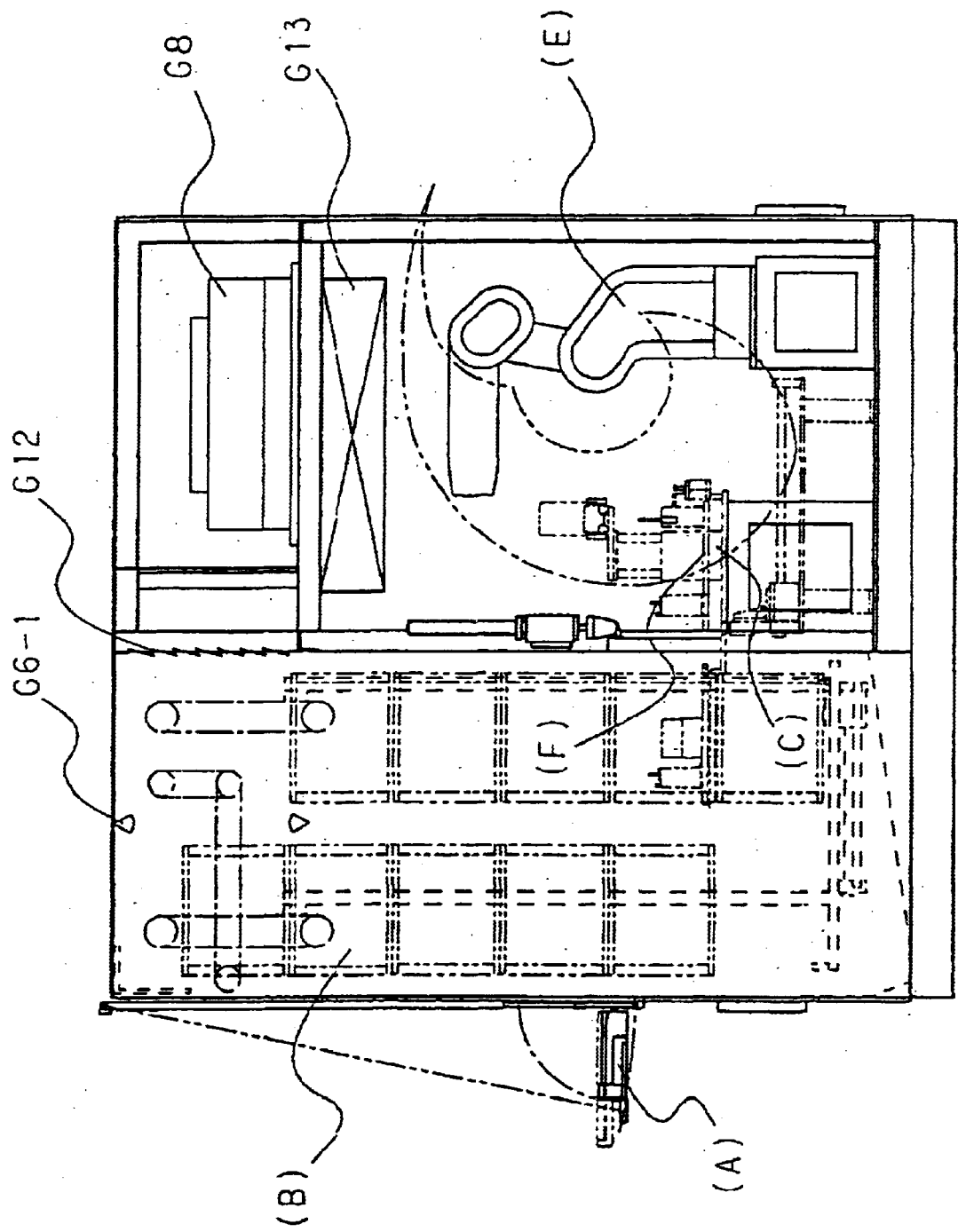
FIG. 55 shows a side view of the automatic sterile testing apparatus according to a second embodiment of the present invention.

The operation of the work stocker B has to this point been described on the assumption that ascent and descent is accomplished using cylinders. However, as shown in FIG. 55 chains and elevators can also be used.

Figure 35:
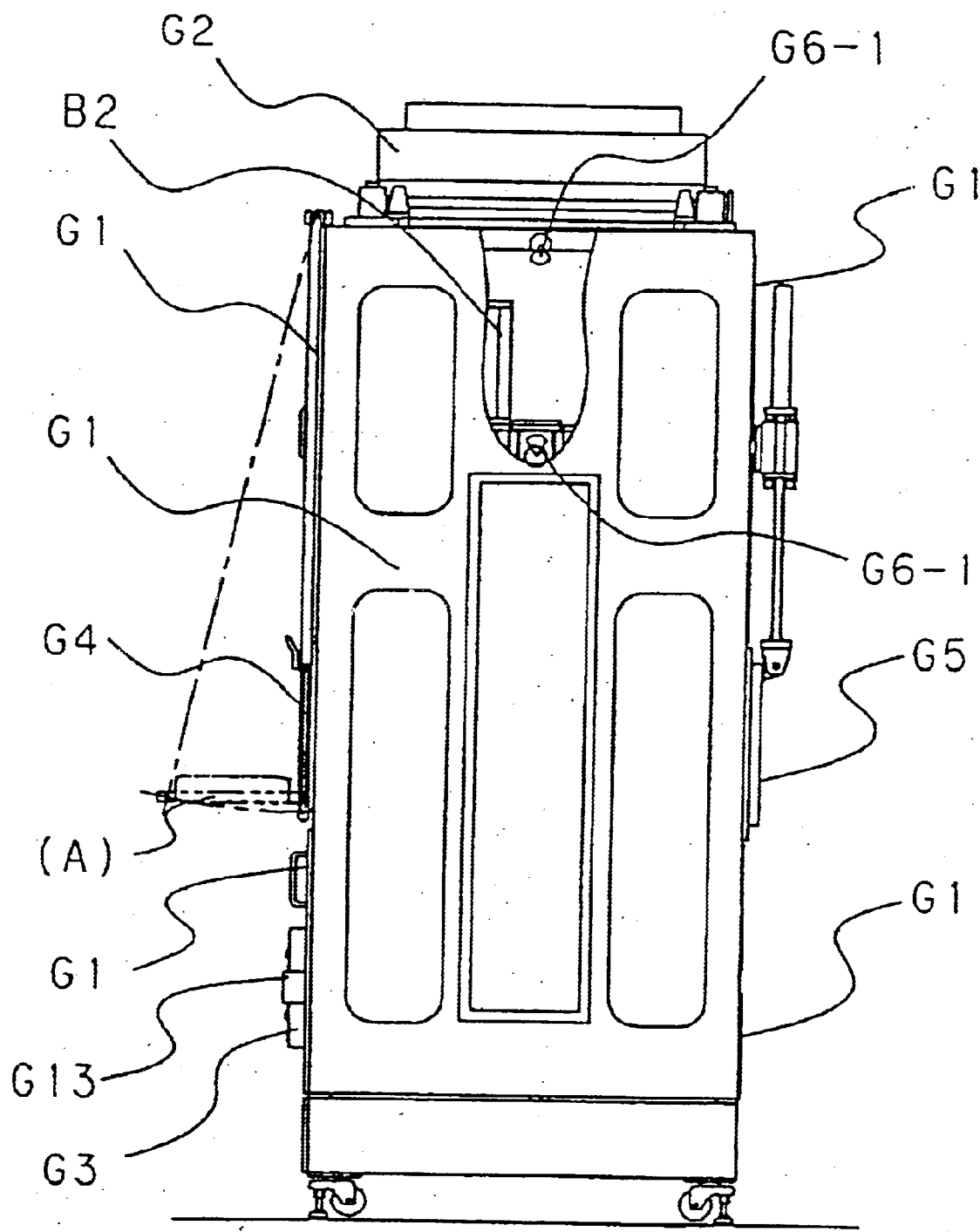
FIG. 35 shows a front view of a stocker chamber.

As shown in FIG. 35 (front view of a stocker chamber) the work stocker B is entirely covered by a first covering G1 and sealed (hereinafter referred to as stocker chamber (S)). The work stocker (B) has a clean booth function in that a first filter unit G2 is mounted on an upper portion, an exhaust port G3 is provided on a lower portion side surface, a door G4 is provided on a side having a detachably attached work table (A) in order to permit a work table F to be inserted and retrieved, and an automatic door G5 is provided on a side having the work manipulation table (C).

A first spray nozzle G6-1 is provided on the interior of the stocker chamber (S) so that the interior of the stocker chamber S, including the work base F, can be sterilized.

Figure 36:
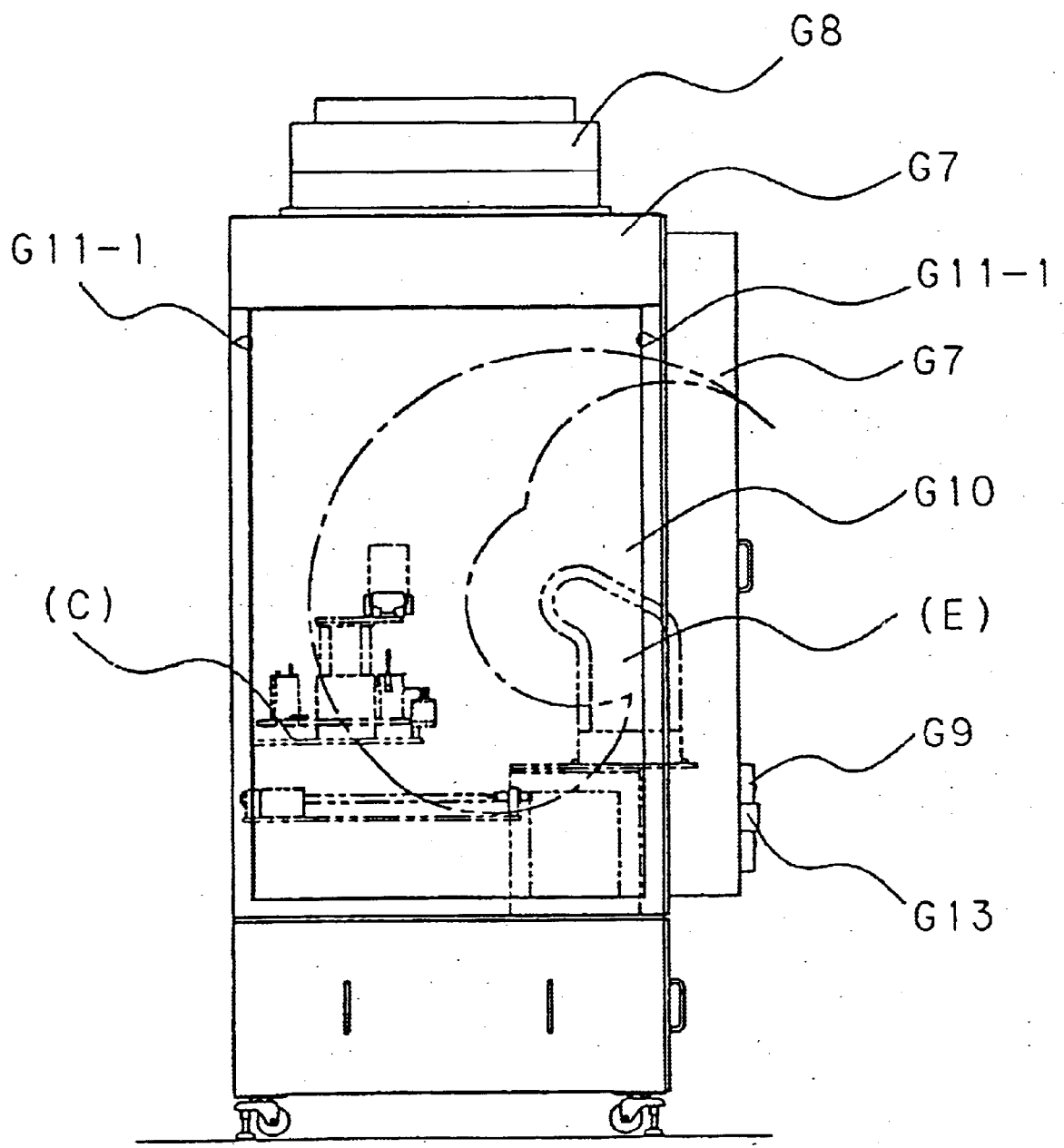
FIG. 36 shows a front view of a robot chamber.

Further, as shown in FIG. 36 (front view of a robot chamber), the periphery of the work manipulation table (C), the auxiliary work manipulation table (D), the work operating robot (E) and the work base (F) is also entirely covered by a second covering G7 to form a sealed structure (hereinafter referred to as robot chamber (R)). As with the stocker chamber (S), the robot chamber (R) has a clean booth function in that a second filter unit G8 is mounted on an upper portion, an exhaust port G9 is provided on a lower portion side surface and a preservation door G4 is provided on a front side.

As with the stocker chamber (S), the interior of the robot chamber (R) is also provided with a spray nozzle (not shown in the diagram) so that the various pieces of equipment installed in the interior of the robot chamber (R) can be sterilized.

Figure 37:
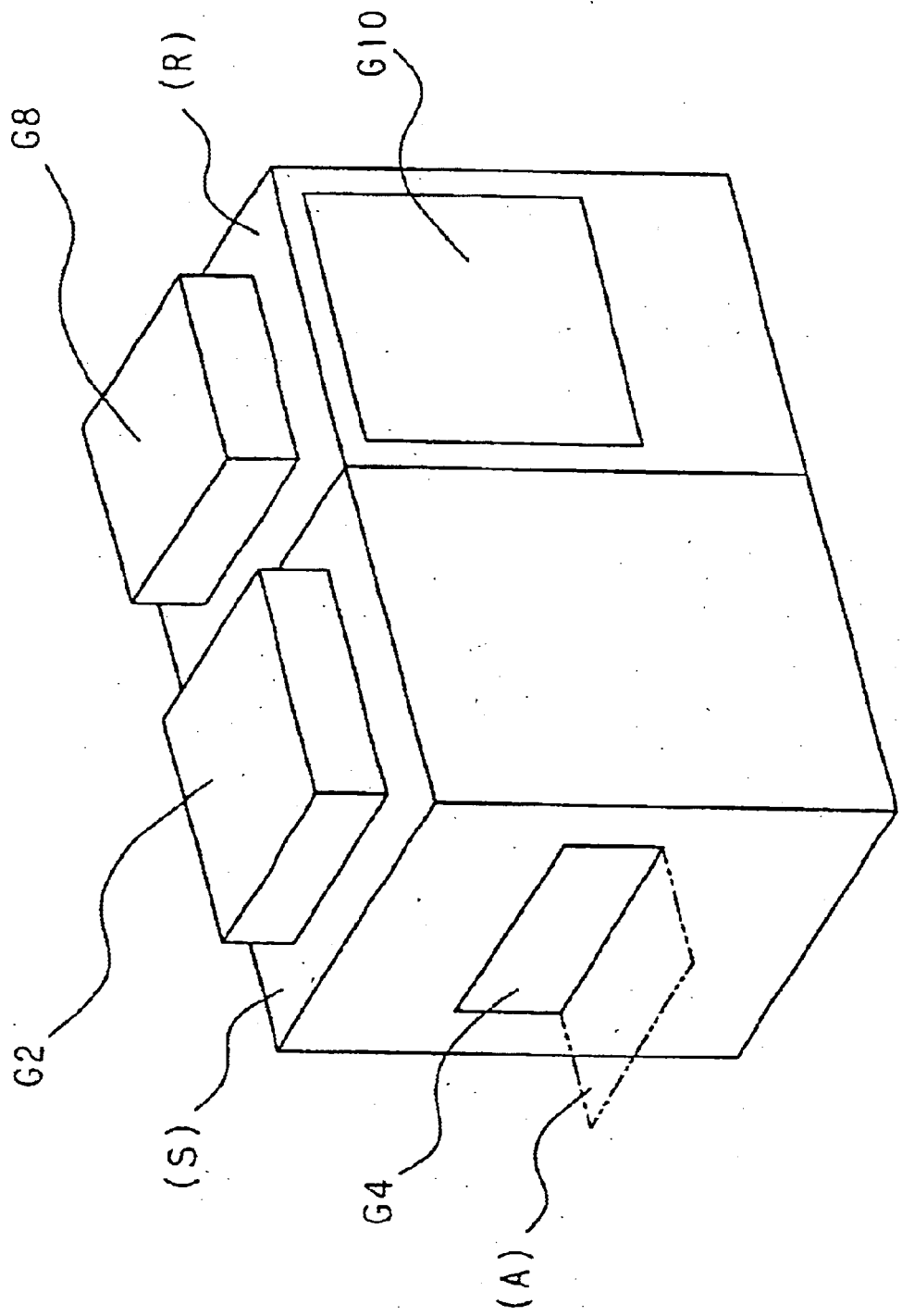
FIG. 37 shows an external view of the entire automatic sterile testing apparatus according to an embodiment of the present invention.
Figure 38:
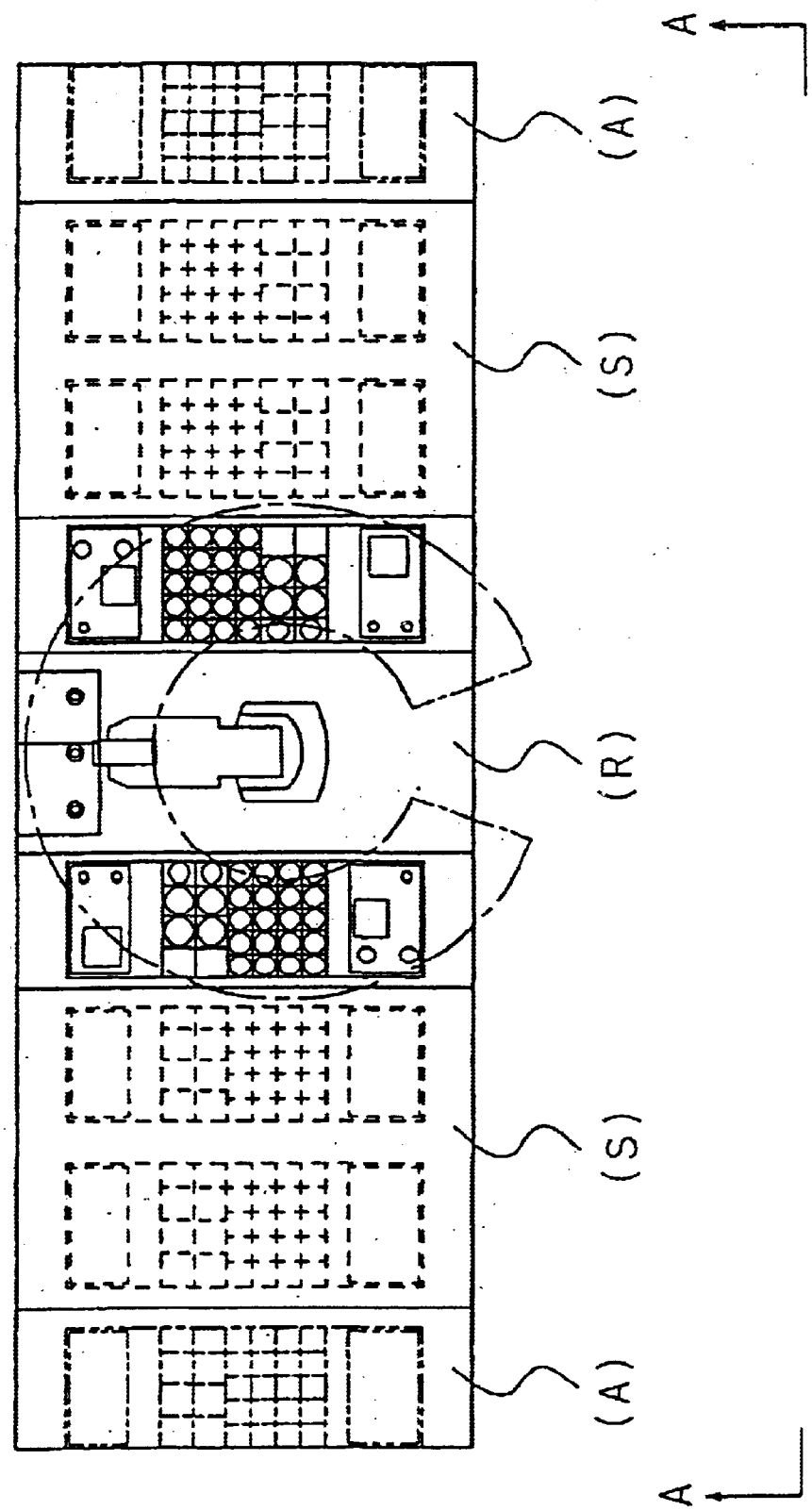
FIG. 38 shows a plan view of an example of an expanded system.
Figure 39:
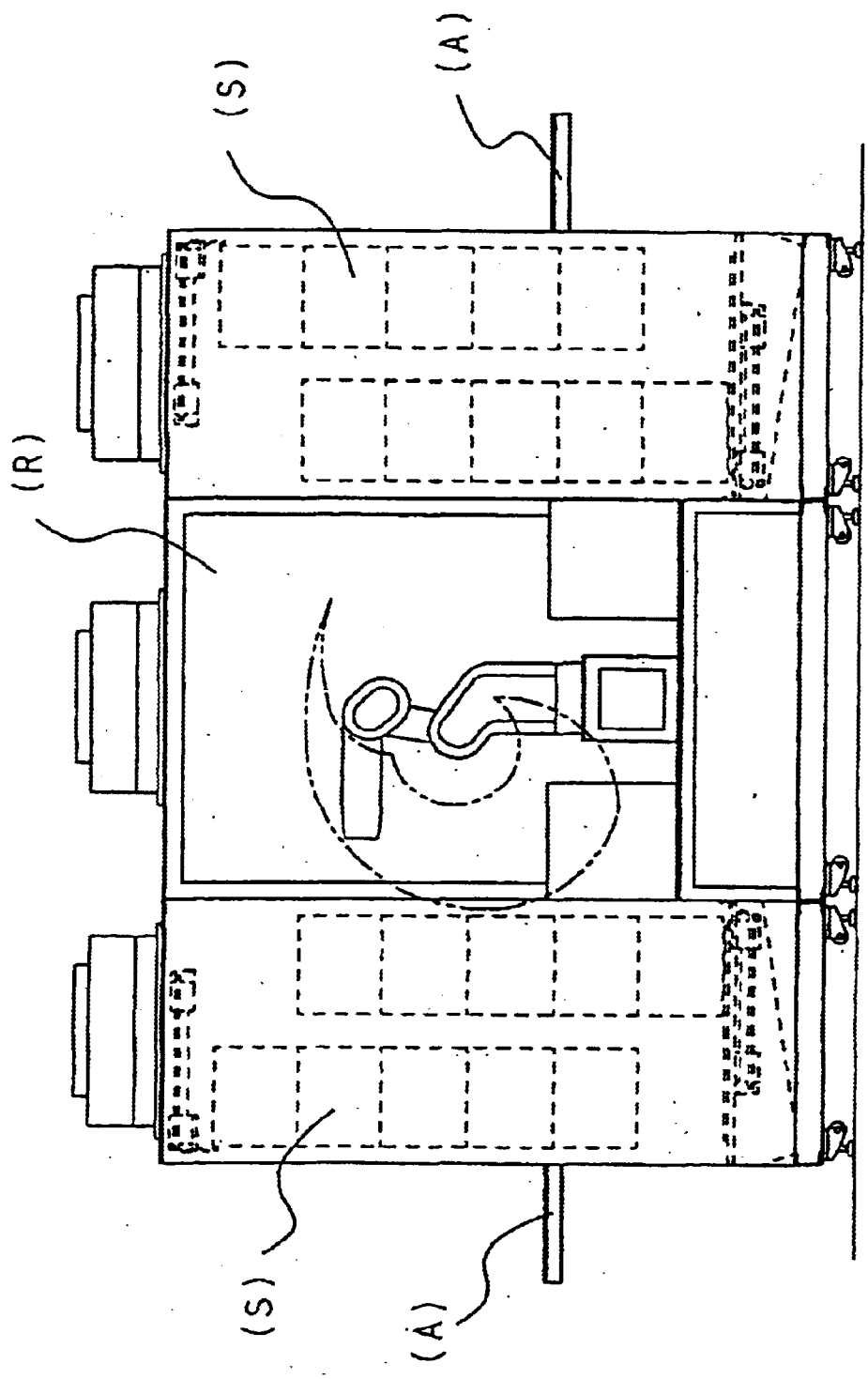
FIG. 39 is a view along the arrows A—A shown in FIG. 38.

FIG. 37 shows an external view of the entire apparatus. It should be noted that the explanation of the present apparatus has up to now assumed an example of a basic configuration consisting of the stocker chamber (S) being connected to one side of the robot chamber (R). However, as shown in FIG. 38 and FIG. 39 (view along the arrows A—A shown in FIG. 38), it is also possible to connect stocker chambers (S) to both sides of the robot chamber (R) in order to increase the productivity of the specimen sample production.

Moreover, the present apparatus has been explained using the example of an embodiment of an automatic sterile testing apparatus using a pressurized filtration method for vials, ampules, etc. As will be explained next, however, by matching the shape of the work base (F) to the shape of the container to be tested as well as to the shape of the equipment needed for its operation, by partially changing and adding to the auxiliary work manipulation table device and by changing the work manipulation robot program, the present invention can be utilized as an automatic sterile testing apparatus according to a suction filtration method, an automatic sterile testing apparatus according to the direct method, an insoluble particulate automatic test manipulation apparatus and, further, an analysis- and reaction-related automatic multiple-solution test manipulation apparatus, without being restricted by container shape or test procedure.

That is, by operating the apparatus according to the suction filtration method of using a membrane filter, by providing a suction pipe C15 (not shown) on the supporting central portion of the solution support base C3-2, providing a cap on the upper portion of the funnel and connecting a lower portion exhaust port of a funnel unit F18 (not shown) having a valve on a lower portion from the filter to the suction pipe C15, said funnel unit F18 acquires a suction filtration function. Said funnel unit F18 is previously provided on the container case F1; by installing said funnel unit F18 on the device C3 for grasping and raising or lowering a specimen container as necessary sample can be made using suction filtration in the same way as with the suction filtration method.

The making of a sample with the direct method involves simply a process of combining and repeating the procedures of attaching and detaching test tube caps, separating solutions into portions and vibrating the tubes so as to promote dissolution, so in this case also the required samples can be made simply by using the solution injection pump unit F2.

In the case of making a sample filter in order to measure the insoluble particulates in a specimen the procedure is virtually the same as that for the suction filtration method. In this case it is not necessary to inject the culture medium.

The process of separating the solution into portions that is frequently undertaken during analysis is also done using only the solution injection pump unit F2, without using the pump unit F3 for injecting a variety of solutions.

Next, a description will now be given of several examples of operation of the automatic sterile testing apparatus of the aforementioned embodiment.

EXAMPLE I

The Specimen Container to be Tested F1-1 is a Powder-filled Vial

Figure 40:
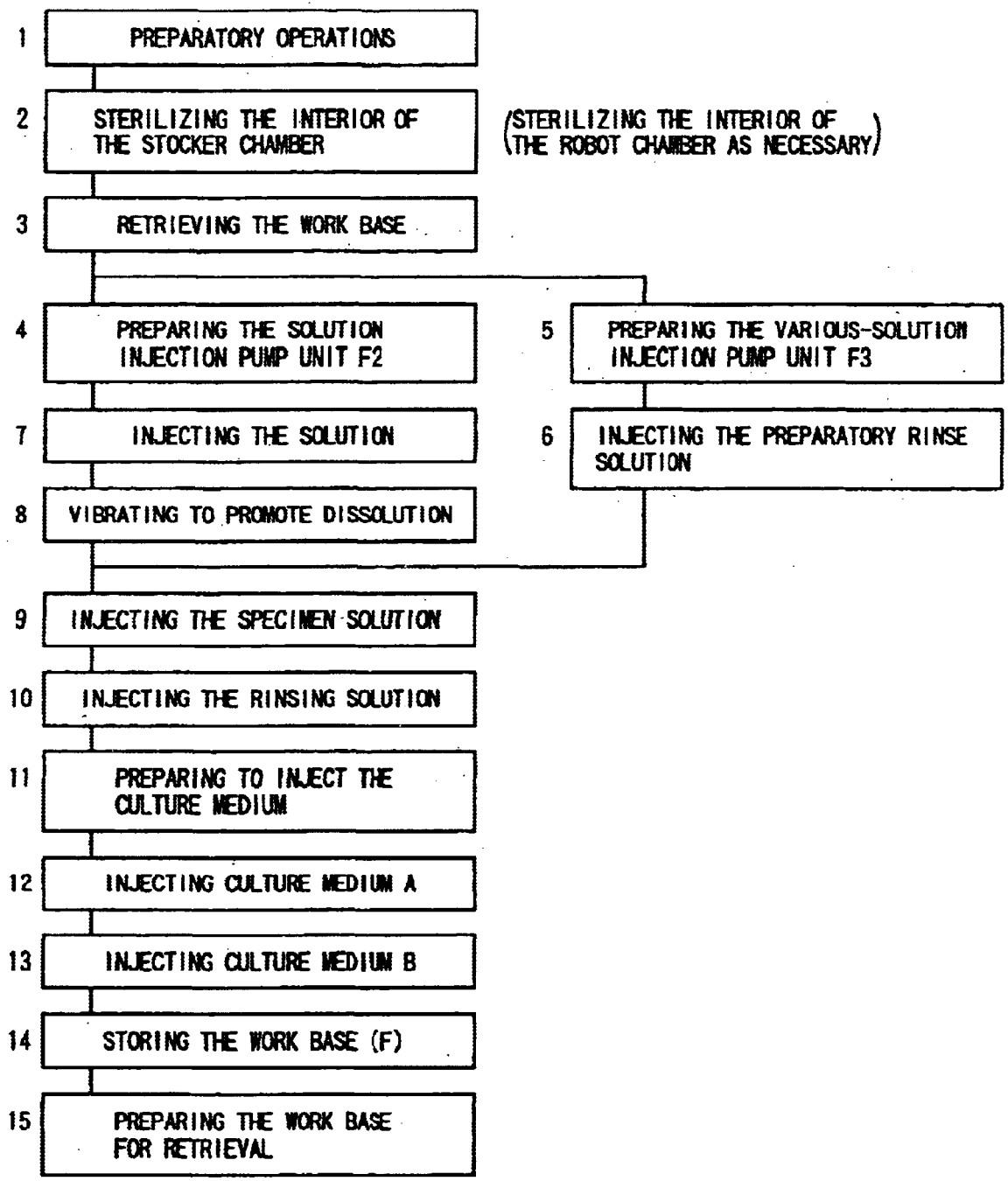
FIG. 40 is a flow chart showing an example of the order of operations in the case of a test specimen consisting of powder-filled vials.

Operation of the apparatus in the event that the specimen container to be tested F1-1 is a powder-filled vial is for example in accordance with the procedure shown in FIG. 40.

(1) Preparatory Operations
- (1-1) Door G4, which also doubles as the detachably attached specimen table (A) of the work stocker (B) is opened and the work base (F) is retrieved, while the operationally complete container case F1, the solution injection tube unit F8 and the sterile test unit F14 are removed. A previously prepared container case F1, solution injection tube unit F8 and sterile test unit F14 are attached and the sample number or registration number are input into the control device.
- (1-2) The aforementioned operation is repeated as many times as necessary (in the diagram any number of repetitions from 1 to 10 can be set) and the door G4 that also doubles as the detachably attached specimen table (A) is closed.
- (1-3) The switch to commence operation is thrown, automatically carrying out the following (15) operations.

(2) Sterilizing the interior of the stocker chamber (S)
- (2-1) The spray nozzle G6-1 is activated, emitting a disinfectant spray for a predetermined cycle or for a predetermined period of time.
- (2-2) After spraying is completed the interior of the chamber is fumigated for a predetermined cycle or for a predetermined period of time.
- (2-3) After fumigation is completed the interior of the chamber is aired out for a predetermined cycle or for a predetermined period of time.
- (2-4) Further, work stocker (B) is circulated so that the first frame of the circulating frame B2 is positioned at the automatic door G5.

(3) Retrieving the work base (F)
- (3-1) The automatic door G5 of the work stocker (B) is opened.
- (3-2) The work base retrieval and storage device C1 is activated, the work base (F) is positioned atop the work manipulation table and raised by the first work base position determining device C5 and the second work base position determining device C12, fixing said work manipulation table (C) atop said work base (F).
- (3-3) The automatic door G5 closes.

(4) Preparing the Solution Injection Pump Unit
- (4-1) The solution transport pump rotating device C4 is raised and connected to the solution transfer pump F5.
- (4-2) The first cap F8-8 of the solution injection needle F8-1 is removed by the work manipulation robot (E) and placed in the cap container F1-7 of the container case F1.
- (4-3) The second cap F8-9 of the solution injection needle F8-2 is removed by the work manipulation robot (E) and placed in the cap container F1-7 of the container case F1.

(5) Preparing the Pump Unit F3 for Injecting a Variety of Solutions
- (5-1) The various-solution transport pump rotating device C10 is raised and connected to the various-solution transfer pump F9.
- (5-2) The various-solution suction needle cap is removed, the auxiliary device C7 is activated and the fit between the various-solution suction needle F14-1 of the sterile test unit F14 and the various-solution suction needle cap F14-7 is loosened.
- (5-3) The various-solution suction needle cap F14-7 is removed by the work manipulation robot (E) and placed temporarily on the temporary placement area for a various-solution suction needle cap D6.
- (5-4) The device C11 for attaching and detaching caps on the bottoms of culture tubes is activated, removing a first culture tube bottom cap F14-10 and a second culture tube bottom cap F14-11. Also, said device C11 for attaching and detaching caps on the bottoms of culture tubes is moved laterally to position a first discharge tube C11-8 and a second discharge tube C11-9 at the lower portions of discharge ports of a first culture tube F14-2 and a second culture tube F14-3.
- (5-5) A first device C8 for opening and closing a pinch valve and a second device C9 for opening and closing a pinch valve are activated, opening a first pinch valve F11 and a second pinch valve F12.

(6) Injecting the Preparatory Rinsing Fluid
- (6-1) The preparatory rinsing fluid container F1-2 is retrieved from the container case F1 by the work manipulation robot (E), the position at which the container is grasped is changed by the container grasping position changing device D5 and turned over by the device C6 for grasping and raising or lowering a variety of solution containers.
- (6-2) The device C6 for grasping and raising or lowering a variety of solution containers is lowered and the various-solution suction needle F14-1, which is mounted on the solution suction needle stand F10, is inserted into the cap portion of the preparatory rinsing fluid container F1-2.
- (6-3) The various-solution transfer pump F9 is rotated a predetermined number of times and a predetermined amount of preparatory rinsing fluid is injected into the first culture tube F14-2 and the second culture tube F14-3 and pressure-filtered.
- (6-4) When the aforementioned injection and pressurized filtration of the preparatory rinsing fluid has been completed the device C6 for grasping and raising or lowering a variety of solution containers is raised and the various-solution suction needle F14-1 is withdrawn. The preparatory rinsing fluid container F1-2 is retrieved from the device C6 for grasping and raising or lowering a variety of solution containers by the work manipulation robot (E) and stored in a predetermined location in the container case F1 via the container grasping position changing device D5.

(7) Injecting the Solution
- (7-1) The solution container F1-4 is retrieved from the container case F1 by the work manipulation robot (E), the position at which the container is grasped is changed by the container grasping position changing device D5 and inverted by the device C2 for grasping and raising or lowering the solution container.

(7-2) The device C2 for grasping and raising or lowering the solution container is lowered and the solution suction needle F8-1 is inserted into the cap portion of the solution container F1-4.

(7-3) The specimen container F1-1 is retrieved from the container case F1 by the work manipulation robot (E), the position at which the container is grasped is changed by the container grasping position changing device D5 and the container positioned at the device C3 for grasping and raising or lowering a specimen container.

(7-4) The device C3 for grasping and raising or lowering a specimen container is raised and the solution injection needle F8-2 is inserted into the cap portion of the specimen container F1-1.

(7-5) The solution transfer pump F5 is rotated a predetermined number of times and a predetermined amount of solution is injected into the specimen container F1-1.

(8) Vibrating to Promote Dissolution (8-1) After the solution has been injected the device C3 for grasping and raising or lowering a specimen container is lowered, the solution injection needle F8-2 is withdrawn from the specimen container F1-1, the specimen container F1-1 is retrieved from the device C3 for grasping and raising or lowering a specimen container by the work manipulation robot (E), positioned at the solution promotion vibrating device D1 provided on the auxiliary work manipulation table (D) and vibrated for predetermined period of time.

(9) Injecting the Specimen Solution (9-1) After it has been vibrated for a predetermined period of time the specimen container F1-1 is retrieved by the work manipulation robot (E), inverted by the container grasping position changing device D5 and positioned at the device C6 for grasping and raising or lowering a variety of solution containers. (In the case of a fluid-injected specimen, the container is retrieved directly from the container case, inverted by the container grasping position changing device D5 and positioned at the device C6 for grasping and raising or lowering a variety of solution containers.

(9-2) The device C6 for grasping and raising or lowering a variety of solution containers is lowered and the various-solution suction needle F14-1 is inserted in the cap portion of the specimen container F1-1.

(9-3) The various-solution transfer pump F9 is rotated a predetermined number of times and either the entire amount or a predetermined amount injected into the first culture tube F14-2 and the second culture tube F14-3 and pressure filtered.

(9-4) After the specimen container has been injected with solution and pressure-filtered, the device C6 for grasping and raising or lowering a variety of solution containers is raised, the various-solution suction needle F14-1 is withdrawn from the specimen container F1-1, the specimen container F1-1 is retrieved from the device C6 for grasping and raising or lowering a variety of solution containers by the work manipulation robot (E) and stored in a predetermined position in the container case F1 by the container grasping position changing device D5.

(9-5) If, for example, there are 20 specimens, then steps (7) through (9) will be repeated 20 times.

(10) Injecting the Rinsing Fluid (10-1) After the specimen solution has been injected into the sterile test unit, the rinsing fluid container F1-3 is retrieved from the container case F1 by the work manipulation robot, inverted, and positioned at the device C6 for grasping and raising or lowering a variety of solution containers by the container grasping position changing device container grasping position changing device D5.

(10-2) The device C6 for grasping and raising or lowering a variety of solution containers is lowered and the various-solution suction needle F14-1 is inserted in the cap portion of the specimen container F1-1.

(10-3) The various-solution transfer pump F9 is rotated a predetermined number of times and either the entire amount or a predetermined amount injected into the first culture tube F14-2 and the second culture tube F14-3 and pressure-filtered.

(10-4) After the specimen container has been injected with solution and pressure-filtered, the device C6 for grasping and raising or lowering a variety of solution containers is raised, the various-solution suction needle F14-1 is removed, the rinsing fluid container F1-3 is retrieved from the device C6 for grasping and raising or lowering a variety of solution containers by the work manipulation robot (E) and stored in a predetermined position in the container case F1 by the container grasping position changing device D5.

(10-5) If there are two or more rinsing fluid containers, the above operations are repeated as many times as necessary.

(11) Preparing to Inject the Culture Medium (11-1) After the specimen solution has been injected into the sterile test unit the device C11 for attaching and detaching caps on the bottoms of culture tubes is moved laterally, the first discharge tube C11-8 and the second discharge tube C11-9 are positioned at the bottom portion of the discharge port of the first culture tube F14-2 and the second culture tube F14-3, the device C11 for attaching and detaching caps on the bottoms of culture tubes is moved laterally and the first culture tube cap F14-10 and the second culture tube cap F14-11 are attached.

(11-2) The first culture tube cap F14-10 and the second culture tube cap F14-11 are detached by the work manipulation robot and the first and second culture tube caps are temporarily placed at the first and second temporary placement positions D7 and D8, respectively.

(12) Injecting Culture Medium A (12-1) A second device C9 for opening and closing a pinch valve is returned to its original position, closing a second pinch valve F12.

(12-2) Culture medium A container F1-5 is retrieved from the container case F1 by the work manipulation robot (E), inverted and positioned at the device C6 for grasping and raising or lowering a variety of solution containers by the container grasping position changing device D5.

(12-3) The device C6 for grasping and raising or lowering a variety of solution containers is lowered and the various-solution suction needle F14-1 is inserted into the cap portion of the culture medium A container F1-5.

(12-4) The various-solution transfer pump F9 is rotated a predetermined number of times and either the entire amount or a predetermined amount of the culture medium A is injected into the first culture tube F14-2.

(12-5) After the culture medium A has been injected, the device C6 for grasping and raising or lowering a variety of solution containers is raised, the various-solution suction needle F14-1 is removed, the culture medium A container F1-5 is retrieved from the device C6 for grasping and raising or lowering a variety of solution containers by the work manipulation robot (E) and is stored in a predetermined position in the container case F1 by the container grasping position changing device D5.

(13) Injecting Culture Medium B (13-1) A first device C8 for opening and closing a pinch valve is returned to its original position, closing a first pinch valve F11.

(13-2) The second device C9 for opening and closing a pinch valve is returned to its original position, opening a second pinch valve F12.

(13-3) Culture medium B container F1-6 is retrieved from the container case F1 by the work manipulation robot (E), inverted and positioned at the device C6 for grasping and raising or lowering a variety of solution containers by the container grasping position changing device D5.

(13-4) The device C6 for grasping and raising or lowering a variety of solution containers is lowered and the various-solution suction needle F14-1 is inserted into the cap portion of the culture medium B container F1-6.

(13-5) The various-solution transfer pump F9 is rotated a predetermined number of times and either the entire amount or a predetermined amount of the culture medium B is injected into the first culture tube F14-3.

(13-6) After the culture medium B has been injected, the device C6 for grasping and raising or lowering a variety of solution containers is raised, the various-solution suction needle F14-1 is removed, the culture medium B container F1-6 is retrieved from the device C6 for grasping and raising or lowering a variety of solution containers by the work manipulation robot (E) and is stored in a predetermined position in the container case F1 by the container grasping position changing device D5.

(14) Storing the Work Base (14-1) A second device C9 for opening and closing a pinch valve is returned to its original position, closing the second pinch valve F12.

(14-2) The first cap F14-8 for the culture tube upper portion exhaust port, which has been temporarily placed on the first temporary placement area for a culture tube upper portion cap D7, is attached to the exhaust port of the first culture tube F14-2 by the work manipulation robot (E).

(14-3) The second cap F14-9 for the culture tube upper portion exhaust port, which has been temporarily placed on the second temporary placement area for a culture tube upper portion cap D8, is attached to the exhaust port of the first culture tube F14-2 by the work manipulation robot (E).

(14-4) The various-solution suction needle cap F14-7, which has been placed on the various-solution suction needle cap temporary placement area D6, is retrieved by the work manipulation robot (E) and attached to the various-solution suction needle F14-1.

(14-5) The various-solution transport pump rotating device C10 is lowered and detached from the various-solution transfer pump F9.

(14-6) The solution transport pump rotating device C4 is lowered and detached from the solution transfer pump F5.

(14-7) The automatic door G5 on the robot chamber (R) side of the stocker chamber (S) is opened.

(14-8) The first work base position determining device C5 and the second work base position determining device C12 are returned to their original positions, the fixing of the work base (F) to the work manipulation table is released, the work base retrieval and storage device C1 is activated and the work base (F) is stored in the work stocker (B).

(14-9) After the work base (F) is stored the automatic door G5 is closed.

(15) Preparing the Work Base for Retrieval (15-1) The work stocker circulates 1 pitch.

In the event that the target specimen consists of, for example, 10 powder-filled vials, the steps 3 (Retrieving the work base (F)) through 15 (Preparing the work base for retrieval) are repeated 10 times.

EXAMPLE II

The Specimen Container to be Tested F1-1 is a Fluid-filled Vial

Figure 41:
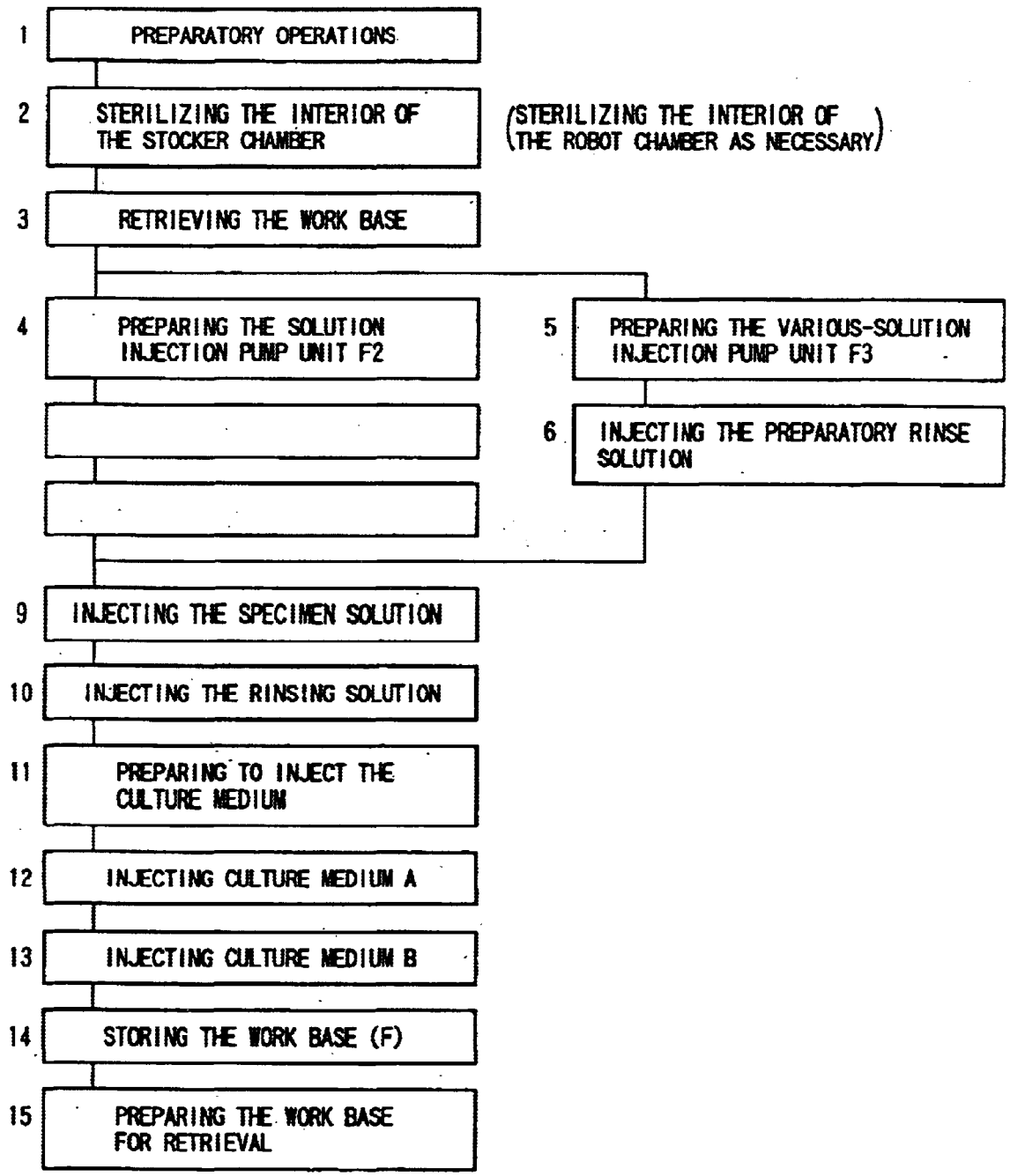
FIG. 41 is a flow chart showing an example of the order of operations in the case of a test specimen consisting of fluid-filled vials.

Operation of the apparatus in the event that the specimen container to be tested F1-1 is a fluid-filled vial is for example in accordance with the procedure shown in FIG. 41.

That is, the procedure is the same as that for a powder-filled vial from steps (1) through (6); steps (7) and (8) are unnecessary and are skipped, with the procedure resuming from step (9) and finishing at step (15).

EXAMPLE III

The Specimen Container to be Tested F1-1 is a Fluid-filled Ampule

Figure 42:
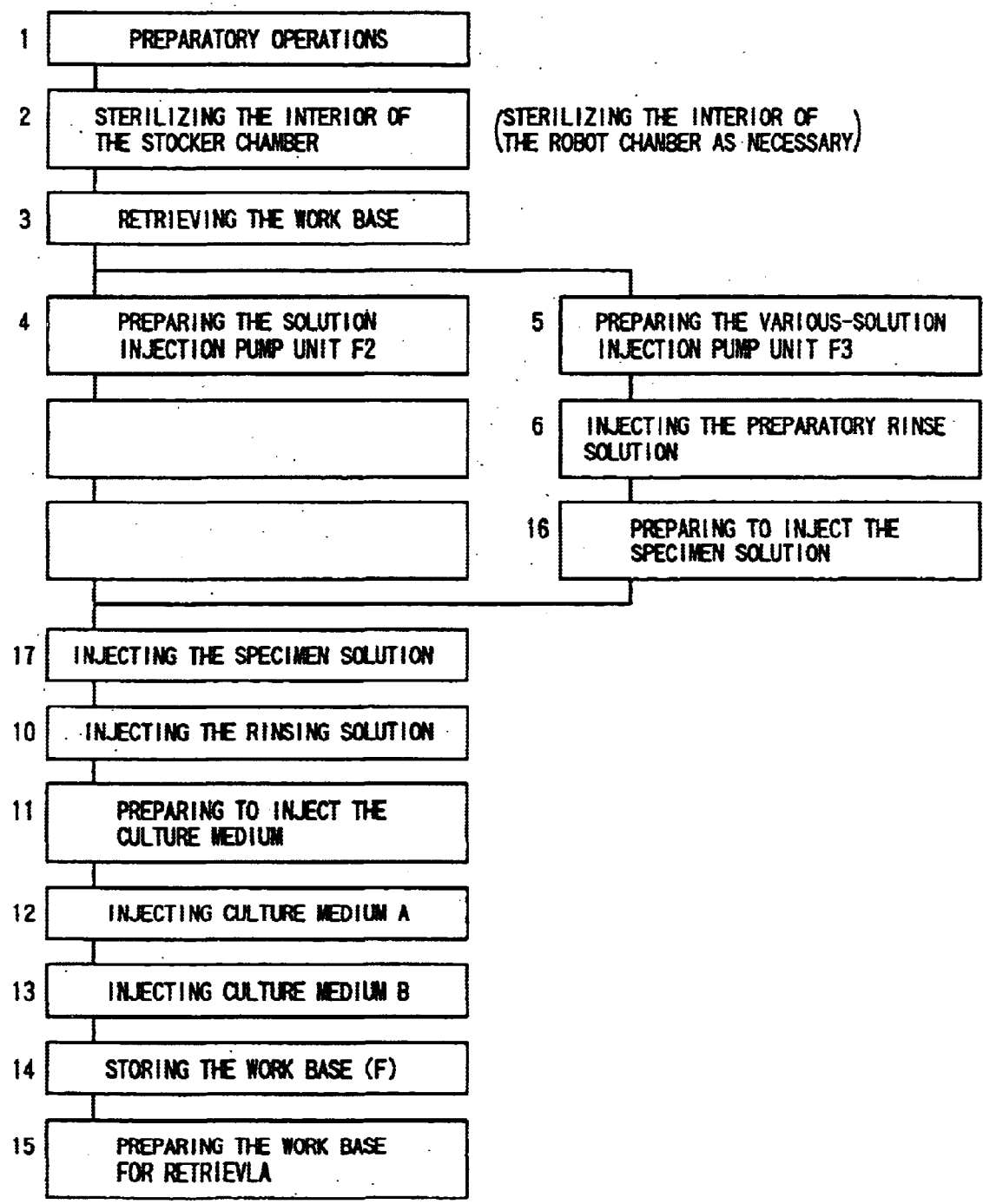
FIG. 42 is a flow chart showing an example of the order of operations in the case of a test specimen consisting of fluid-filled ampules.

Operation of the apparatus in the event that the specimen container to be tested F1-1 is a fluid-filled ampule is for example in accordance with the procedure shown in FIG. 42.

That is, as mentioned previously, an auxiliary ampule injection container F15 is provided and previously positioned at an empty space in the container case F1 at the start of step 1 (Preparatory operations). Thereafter the procedure is the same as that for a powder-filled vial from steps (1) through (6); steps (7) and (8) are unnecessary and are skipped and step (9) is replaced by the following steps (16) and (17), with the procedure continuing from step (10).

(16) Preparing to Inject the Specimen Solution (16-1) The upper cap F15-3 of the auxiliary ampule injection container F15 positioned at the container case F1 is removed by the work manipulation robot (E) and temporarily placed on the temporary placement area for an auxiliary ampule injection container upper portion cap D9. (The cap may also be placed in the collection box F1-7 if there is room in the collection box F1-7.)

(16-2) The auxiliary ampule injection container main body F15-1 (auxiliary ampule injection container lower portion cap F15-2) is removed from the container case F1 by the work manipulation robot (E) and positioned at the device C6 for grasping and raising or lowering a variety of solution containers.

(16-3) The device C6 for grasping and raising or lowering a variety of solution containers is lowered and the various-solution suction needle F14-1 is inserted in the auxiliary ampule injection container lower portion cap F15-2 of the auxiliary ampule injection container F15.

(16-4) The collection box F1-7 is retrieved from the container case F1 by the work manipulation robot (E) and positioned at a predetermined location at the ampule opening device D3.

(17) Injecting the Specimen Solution (17-1) The specimen container F1-1 is retrieved from the container case F1 by the work manipulation robot (E), the position at which it is grasped is changed by the container grasping position changing device D5 and the neck portion of the ampule is broken off using the ampule opening device D3. (The broken-off neck portion of the specimen container F1-1 drops naturally into the collection box F1-7.)

(17-2) The opened specimen container F1-1 is inverted by the auxiliary ampule injection container F15 positioned at the device C6 for grasping and raising or lowering a variety of solution containers. (At this time the opened specimen container F1-1 is held in place by the work manipulation robot (E).)

(17-3) The various-solution transfer pump F9 is rotated a predetermined number of times and either the entire amount or a predetermined amount of the specimen solution is injected into the first culture tube F14-2 and the second culture tube F14-3 and pressure-filtered.

(17-4) After the specimen solution has been injected and pressure-filtered, the specimen container F1-1 is retrieved from the auxiliary ampule injection container F15 and placed in the collection box F1-7.

(17-5) If, for example, there are 20 specimens, then steps (17-1) through (17-4) will be repeated a total of 20 times.

(17-6) After a predetermined number of specimen solutions have been injected and pressure-filtered, the device C6 for grasping and raising or lowering a variety of solution containers is raised and the auxiliary ampule injection container F15 is retrieved and stored in the container case F1.

After the injection of the specimen solution of the fluid-filled ampules in step (17), steps (10) through (15) in the aforementioned case of the specimen being a powder-filled vial are then carried out.

In the event that the following specimens are fluid-filled ampules and that there are 10 such samples, then steps (3) (Retrieving the work base (F)) through (15) (Preparing the work base for retrieval) are repeated 10 times.

EXAMPLE IV

The Specimen Container to be Tested F1-1 is a Powder-filled Ampule

Figure 43:
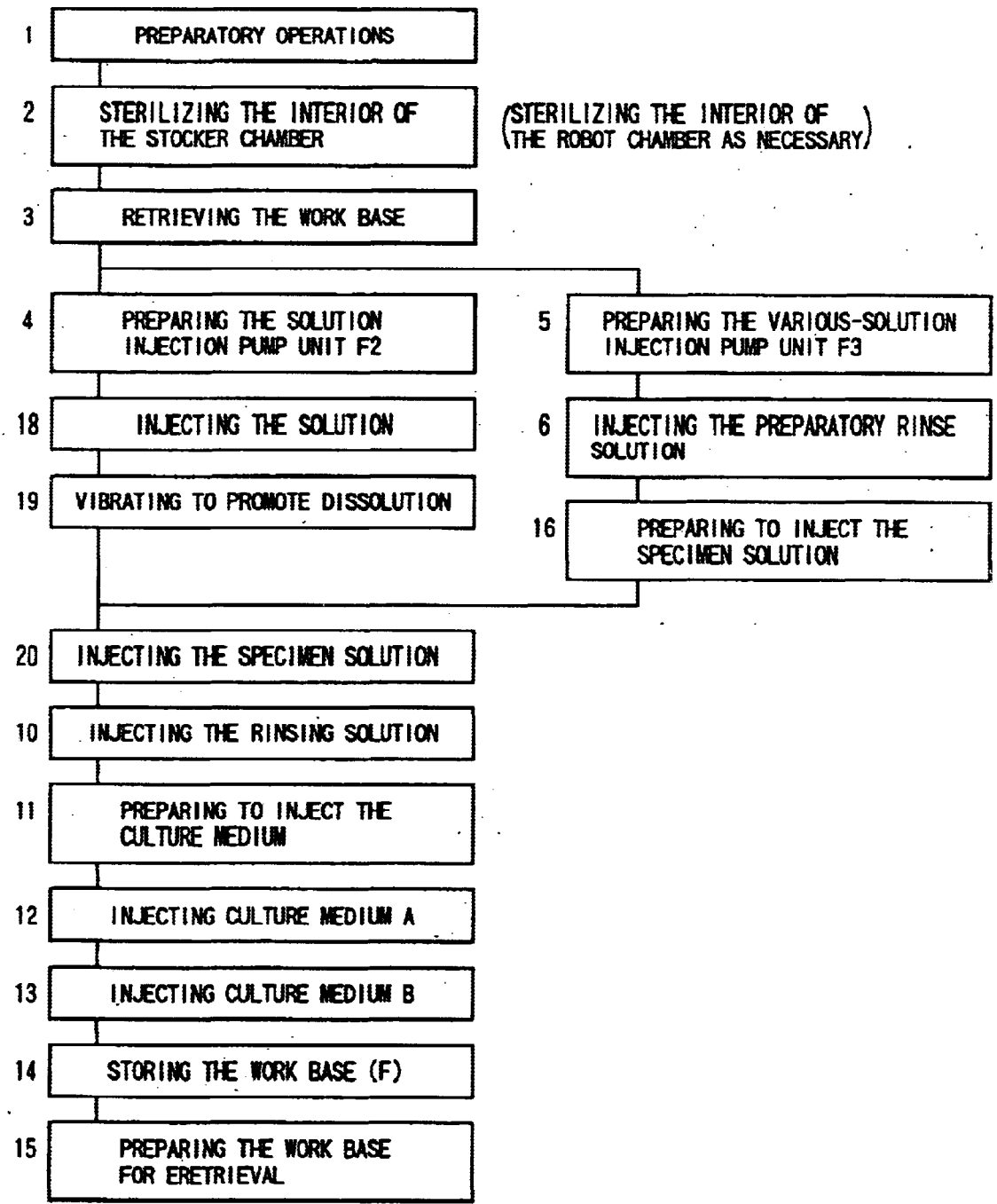
FIG. 43 is a flow chart showing an example of the order of operations in the case of a test specimen consisting of powder-filled ampules.

Operation of the apparatus in the event that the specimen container to be tested F1-1 is a powder-filled ampule is for example in accordance with the procedure shown in FIG. 43.

That is, the procedure is the same as that for a powder-filled vial from steps (1) through (6), with the procedure continuing from step (16) and continuing with the following steps (18) and (19).

(18) Injecting the Solution (18-1) The solution container F1-4 is retrieved from the container case F1 by the work manipulation robot (E), the position at which it is grasped is changed by the container grasping position changing device D5, inverted and positioned at the device C2 for grasping and raising or lowering the solution container.

(18-2) the device C2 for grasping and raising or lowering the solution container is lowered and the solution suction needle F8-1 inserted in the solution container F1-4.

(18-3) The specimen container F1-1 is retrieved from the container case F1 by the work manipulation robot (E), the position at which it is grasped is changed by the container grasping position changing device D5 and the neck portion of the ampule is broken off using the ampule opening device D3.

(18-4) The opened specimen container F1-1 is positioned at the device C3 for grasping and raising or lowering a specimen container.

(18-5) The device C3 for grasping and raising or lowering a specimen container is raised and the solution injection needle F8-2 is inserted into the opening of the specimen container specimen container F1-1.

(18-6) The solution transfer pump F5 is rotated a predetermined number of times and a predetermined amount of solution is injected into the specimen container F1-1.

(19) Vibrating to Promote Dissolution (19-1) After the solution has been injected the device C3 for grasping and raising or lowering a specimen container is lowered, the grip on the specimen container F1-1 is released, the specimen container F1-1 is retrieved from the device C3 for grasping and raising or lowering a specimen container by the work manipulation robot (E), positioned at the solution promotion vibrating device D1 provided on the auxiliary work manipulation table (D) and vibrated for a predetermined period of time.

(20) Injecting the Specimen Solution (20-1) After it has been vibrated for a predetermined period of time the specimen container F1-1 is retrieved from the solution promotion vibrating device D1 by the work manipulation robot (E), inverted and positioned at the auxiliary ampule injection container F15 provided on the device C6 for grasping and raising or lowering a variety of solution containers. (The container is held in place by the work manipulation robot (E)).

(20-2) The various-solution transfer pump F9 is rotated a predetermined number of times and either the entire amount or a predetermined amount of the specimen solution is injected into the first culture tube F14-2 and the second culture tube F14-3 and pressure filtered.

(20-3) After the specimen solution has been injected and pressure-filtered, the specimen container F1-1 is retrieved from the auxiliary ampule injection container F15 and placed in the collection box F1-7.

(20-4) If, for example, there are 20 specimens, then steps (18-3) through (20-3) will be repeated 20 times.

(20-5) After a predetermined number of specimen solutions have been injected and pressure-filtered, the device C6 for grasping and raising or lowering a variety of solution containers is raised and the auxiliary ampule injection container F15 is detached and stored in a predetermined position in the container case F1.

After the above steps are completed the procedure is the same as that for a powder-filled vial, with steps (10) through (15) being carried out.

In the event that the following specimens are powder-filled vials and that there are 10 such samples, then steps (3) (Retrieving the work base (F)) through (15) (Preparing the work base for retrieval) are repeated 10times.

EXAMPLE V

The Specimen Container to be Tested F1-1 is a Powder-filled Ampule

In this case, as per the above the fixed container for indeterminate-shape containers F16 is used. The procedure is virtually the same as that for Example II, where the specimen container F1-1 is a fluid-filled vial (FIG. 41), so a description thereof will be omitted. (In the event that the specimen container F1-1 is a transfusion solution bag there are times when steps (6) and (10) will be omitted.)

EXAMPLE VI

The Specimen Container to be Tested F1-1 is a Powder-filled Ampule

Figure 44:
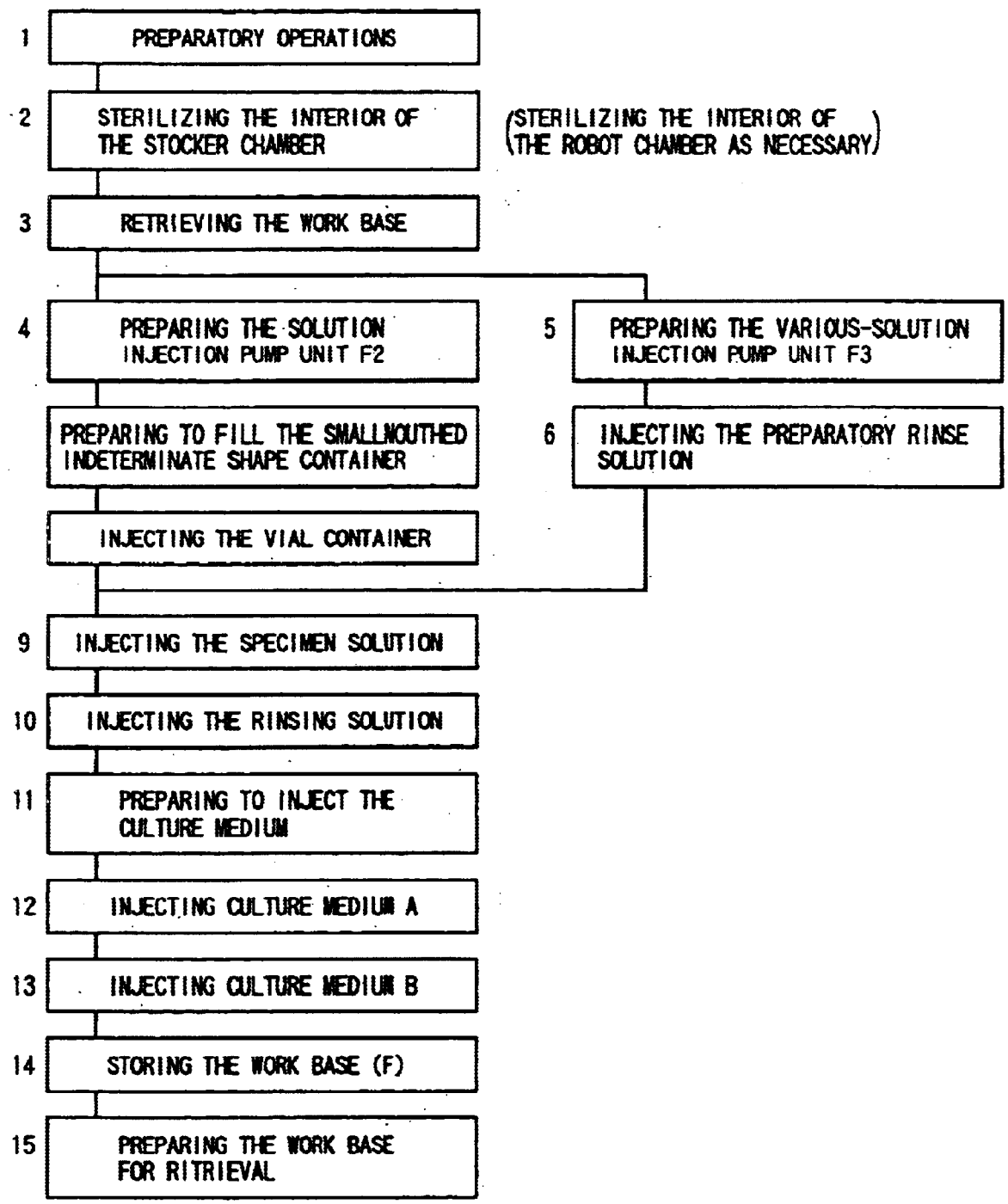
FIG. 44 is a flow chart showing an example of the order of operations in the case of a test specimen consisting of small-mouth-diameter containers of indeterminate sizes.

In this case, the procedure is as described in FIG. 44. That is, the indeterminate-shaped container injection tube unit F17 is previously positioned at the solution injection pump unit F2, the fixed container for indeterminate-shape containers F16 with a built-in specimen container F1-1 is positioned at the device C2 for grasping and raising or lowering the solution container in place of the solution container F1-4, an empty vial container is positioned at the device C3 for grasping and raising or lowering a specimen container, the same procedure as that in step (7) of injecting the solution is carried out, and the solution in the specimen container F1-1 is injected all at once into the vial container. Thereafter the container is positioned at the device C6 for grasping and raising or lowering a variety of solution containers and steps (9) and thereafter are carried out. In this case, too, there are times when steps (6) and (10) are omitted.

EXAMPLE VII

The Specimen Container to be Tested F1-1 is a Powder-filled Vial with a Small Amount of Fluid In this case, the procedure is as per the flow chart shown in FIG. 40. However, once steps (7), (8) and (9) have been carried out using the specimen container F1-1, step (8) is thereafter omitted while steps (7) and (9) are repeated as often as necessary, with the procedure resuming with step (10). With this procedure virtually the entire solution contents of the specimen container F1-1 can be sent to the culture tubes.

EXAMPLE VIII

The Specimen Container to be Tested F1-1 is a Fluid-filled Vial with a Small Amount of Fluid In this case, the procedure is as per the flow chart shown in FIG. 41. However, after step (9) has been carried out once using the specimen container F1-1, the rinsing fluid container F1-3 is positioned at the device C2 for grasping and raising or lowering the solution container, the specimen container F1-1 is positioned at the device C3 for grasping and raising or lowering a specimen container so as to carry out a rinsing fluid injection step similar to the solution injection of step (7) and step (9) is performed once again. After the rinsing fluid has been injected and step (9) has been carried out the required number of times, the procedure resumes with step (10). As with the procedure of Example VII, with this procedure, too, virtually the entire solution contents of the specimen container F1-1 can be sent to the culture tubes.

EXAMPLE IX

The Specimen Container to be Tested F1-1 is a Fluid-filled Ampule with a Small Amount of Fluid In this case, the procedure is as per the flow chart shown in FIG. 42. However, after step (17) has been carried out once using the specimen container F1-1, the rinsing fluid container F1-3 is positioned at the device C2 for grasping and raising or lowering the solution container, the specimen container F1-1 is positioned at the device C6 for grasping and raising or lowering a variety of solution containers so as to carry out a rinsing fluid injection step similar to the solution injection of step (7) and step (17) is performed once again. After steps (21) and (17) have been carried out the required number of times, the procedure resumes with step (10). As with the procedure of Example VII, with this procedure, too, virtually the entire solution contents of the specimen container F1-1 can be sent to the culture tubes.

EXAMPLE X

The Specimen Container to be Tested F1-1 is a Powder-filled Ampule with a Small Amount of Fluid In this case, the procedure is as per the flow chart shown in FIG. 43. However, after steps (18), (19) and (20) have been carried out once using the specimen container F1-1, step (19) is thereafter omitted and steps (18) and (20) are repeated as many times as necessary, after which the procedure resumes with step (10). As with the procedure of Example VII, with this procedure, too, virtually the entire solution contents of the specimen container F1-1 can be sent to the culture tubes.

EXAMPLE XI

Separate Method where the Amount of Fluid is Small

In the event that the amount of fluid is small, such as in examples VII through X, where the shape of the specimen container F1-1 is that of a vial the container is positioned as is at the device C2 for grasping and raising or lowering the solution container. Where the shape of the specimen container F1-1 is that of an ampule the container is positioned at the auxiliary ampule injection container F15, a large empty vial is positioned at the device C3 for grasping and raising or lowering a specimen container, the entire contents of the ampule are moved to the vial and, further, a solution or a rinsing fluid is injected into the vial. After the volume of the specimen has been increased the test procedure can be resumed with steps (9) through (15).

EXAMPLE XII

When Using the Suction Method

The injection of various types of solutions into the funnel unit F18 (not shown in the diagrams) is carried out using the solution injection pump unit F2. Therefore the location at which the funnel unit F18 is positioned becomes that of the device C3 for grasping and raising or lowering a specimen container and the pump unit F3 for injecting a variety of solutions is not used. Virtually the same procedures as those used in examples I through X are carried out for both vials and ampules simply by changing the aforementioned operating position.

EXAMPLE XIII

When Using the Direct Method

Figure 45:
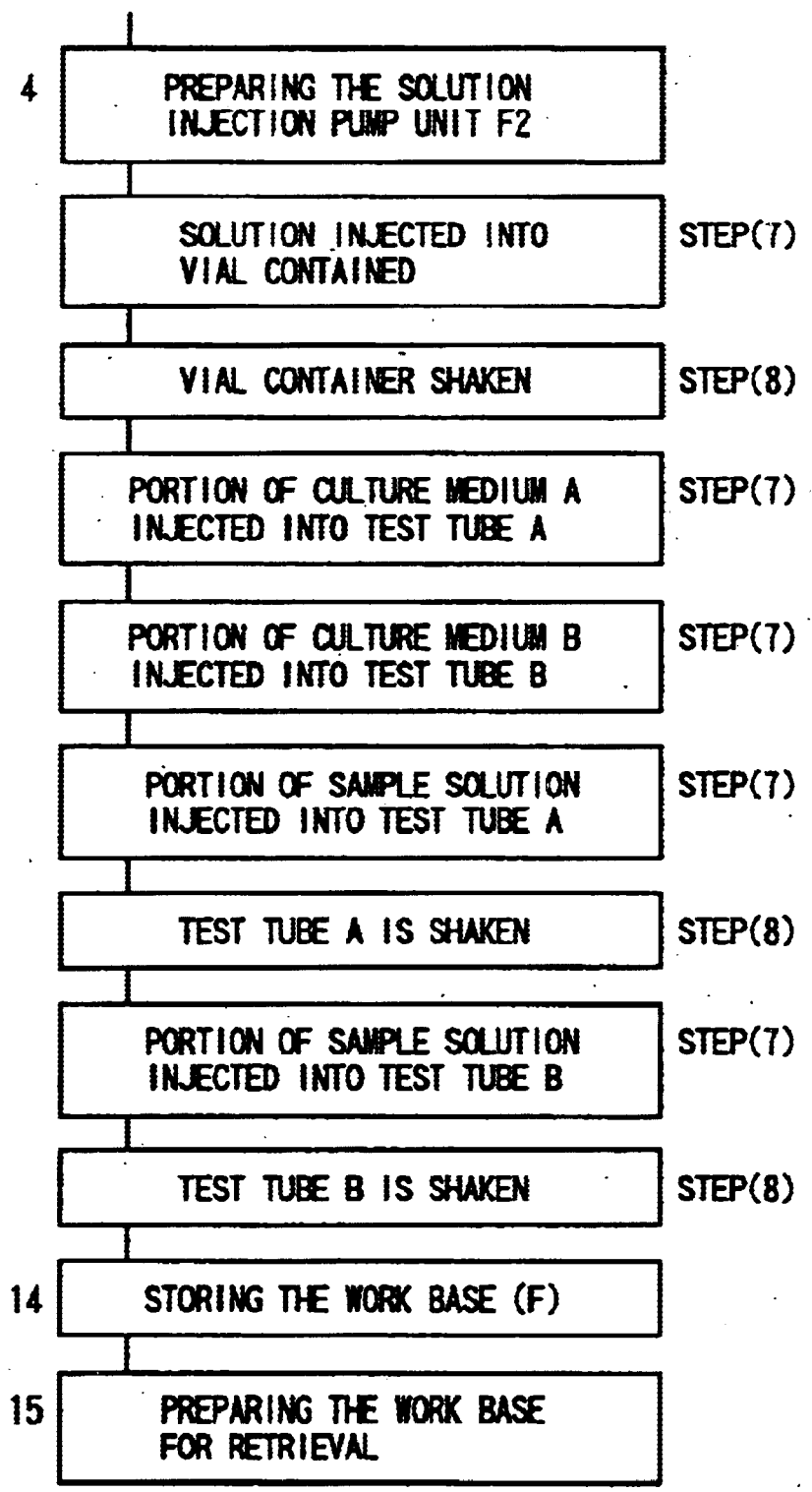
FIG. 45 is a flow chart showing an example of the order of operations in the case of an automatic test in accordance with the direct method.

In the direct method no filter is used, so the injection of various types of solutions is done entirely by separating the solutions into portions. Where the number or amount of the specimens is large the solution injection pump unit F2 is used. In this case, the procedure is carried out in the steps shown in FIG. 45. In the example shown in this diagram, the various containers are each specified separately. As the number of containers increases the number of times the steps need to be repeated increases by the same number. It should be noted that the operation of stopping and unstopping the containers is carried out using the container grasping position changing device D5, though that step is omitted from the flow chart.

In case the number or amount of the specimens is small the work of separating the specimens into portions is carried out using a cylinder instead of the solution injection pump unit F2. When carrying out this operation an additional auxiliary container grasping device having the same specifications as the container grasping position changing device D5 is needed as an auxiliary work manipulation device.

Figure 46:
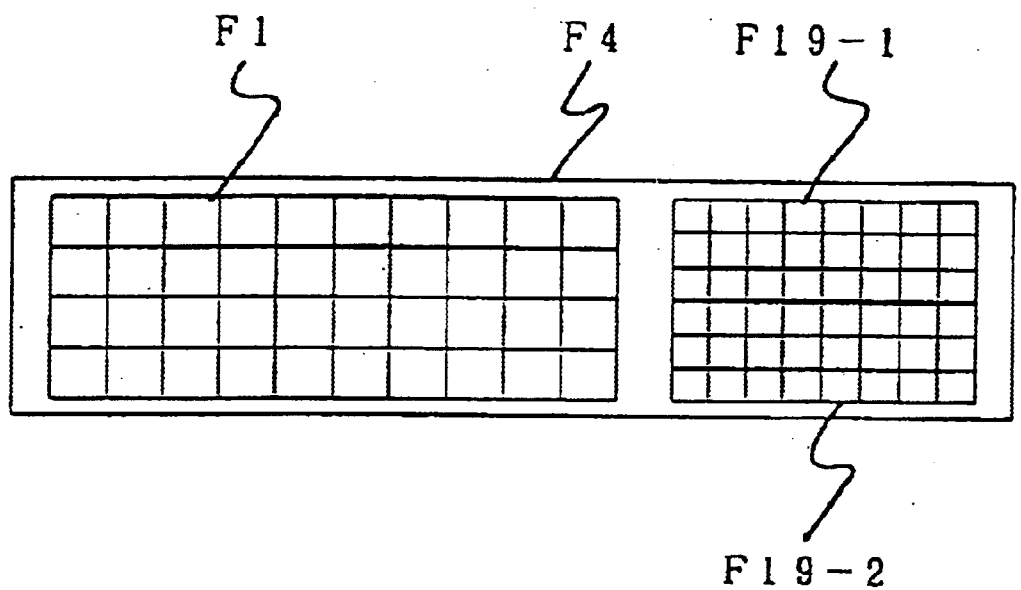
FIG. 46 shows an example of a container case arrangement in the case of the target containers being test tubes and freshets.
Figure 47:
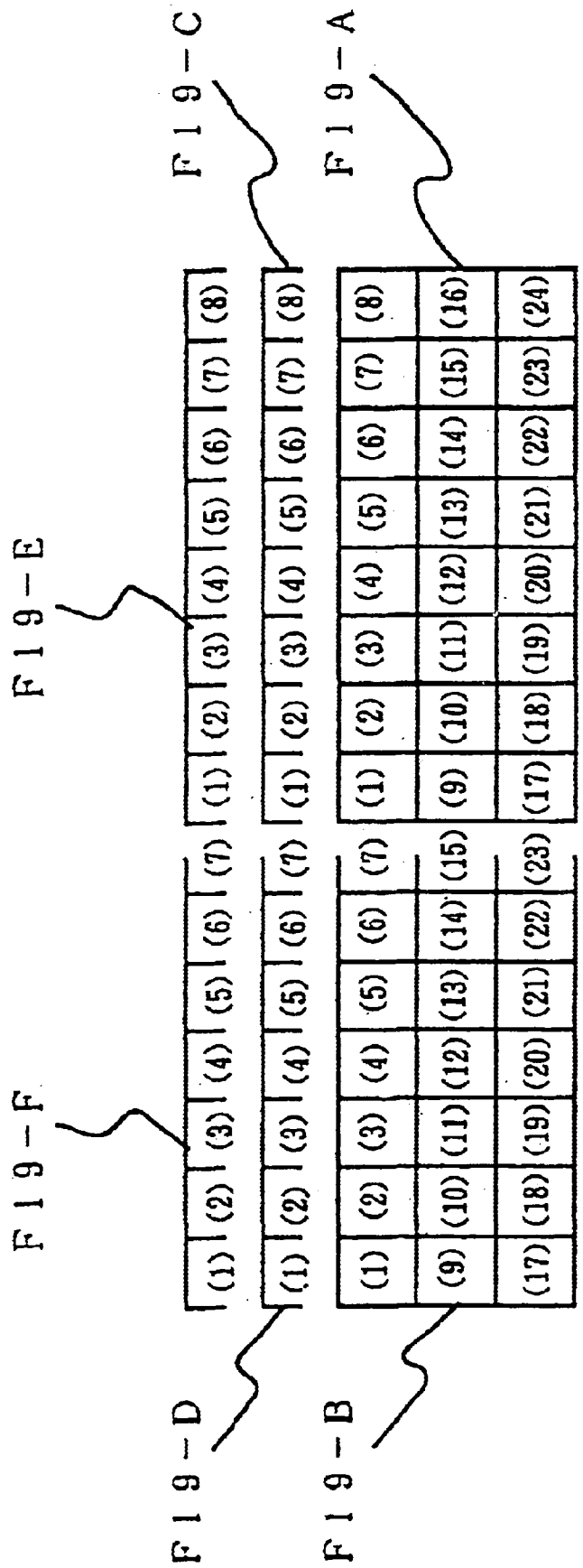
FIG. 47 is a diagram for explaining a method for moving test tubes.

A description will now be given of an example of an operating procedure in the event that the containers into which the specimens have been divided consist of test tubes. As shown in FIG. 46, the container case F1, and a first test tube stand F19-1 and a second test tube stand F19-2 into which the test tubes (not shown in the diagram) are stored, are placed atop the work palette F4. The specimen solution within the container case F1 is retrieved by the robot hand E1 and a predetermined amount of the specimen solution is injected into the test tube(s). In the event that the test tubes are positioned adjacent to one another inside the first and second test tube stands F19-1 and F19-2 and cannot be removed by the robot hand E1, the test tube stand F19 in which the test tubes are stored is removed from atop the work palette F4 by the robot hand E1 and placed on the auxiliary work table D4 as per the condition shown as F19-A in FIG. 47. At this time, the test tube stand is positioned so that a test tube push-up device D22 (not shown in the diagram) provided on the auxiliary work table D4 is located directly beneath a first test tube. When the test tube push-up device D22 is activated the first test tube is pushed up above the surrounding test tubes in such a way that the surrounding test tubes do not pose an obstacle even if the test tubes are positioned adjacent to each other, thus enabling the robot hand E1 to easily grasp the subject test tube. Once the necessary operations involving the first test tube are completed the test tube stand F19 is moved one pitch to the left by the robot hand E1 in such a way that a second test tube is positioned directly above the test tube push-up device D22. The test tube stand is moved in successive stages from the condition of F19-A to the condition of F19-B, in which test tube no. 8 is positioned directly above the test tube push-up device D22, to a condition of F19-C, in which test tube no. 9 is positioned directly above the test tube push-up device D22, to a condition of F19-D, in which test tube no. 16 is positioned directly above the test tube push-up device D22, to a condition of F19-E, in which test tube no. 17 is positioned directly above the test tube push-up device D22, to a condition of F19-F, in which test tube no. 24 is positioned directly above the test tube push-up device D22, at which point the operation is completed and the test tube stand F19 is returned to its original position (stored in the work palette F4).

An explanation will now be given of several examples of making samples for microorganism limit testing.

EXAMPLE XIV

Making Samples According to the Membrane Filter Attachment Method

Figure 48:
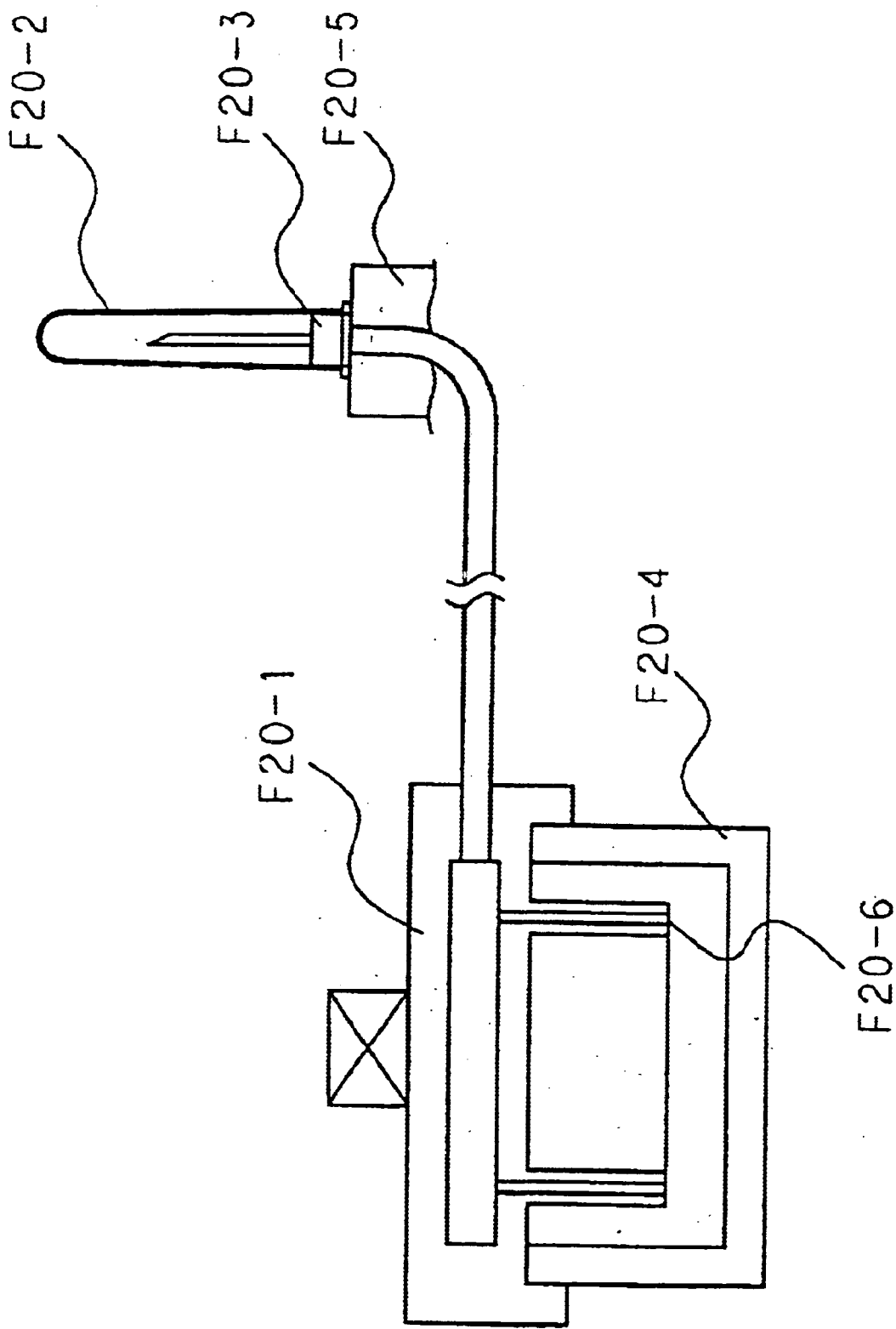
FIG. 48 shows a filter suction jig unit.

The procedure is virtually the same as the direct method of making cultured bacteria solution (Example XIII), in which the solution is divided and diluted in a container containing a diluent and filtered according to the suction filtration method using the previously mentioned funnel unit F18, after which it is filtered as necessary, rinsed, moved to a station (not shown in the diagram) at which the funnel section of the funnel unit F18 is removed and the funnel section removed (disassembled). A filter suction jig unit F20 for retrieving the sample filter belonging to the funnel unit F18 and attaching it to the surface of the agar culture medium has been previously stored in the container case F1 as a necessary piece of equipment. The filter suction jig unit F20 is shown in FIG. 48. The filter suction jig unit F20 comprises a suction jig main unit F20-1 having a cylindrical adsorption plate F20-6; an exhaust port cap F20-2; an exhaust port F20-3; and a suction port storage case F20-4. The sample filter is detached using the suction jig main unit F20-1 and attached to the surface of the agar culture medium of the agar culture medium container from which the lid has previously been removed using the robot hand E1, to provide the agar culture medium container with a lid. The storing of each piece of equipment that is no longer needed in a predetermined location in the container case F1 is the same as that of the automatic sterile testing apparatus.

Figure 49:
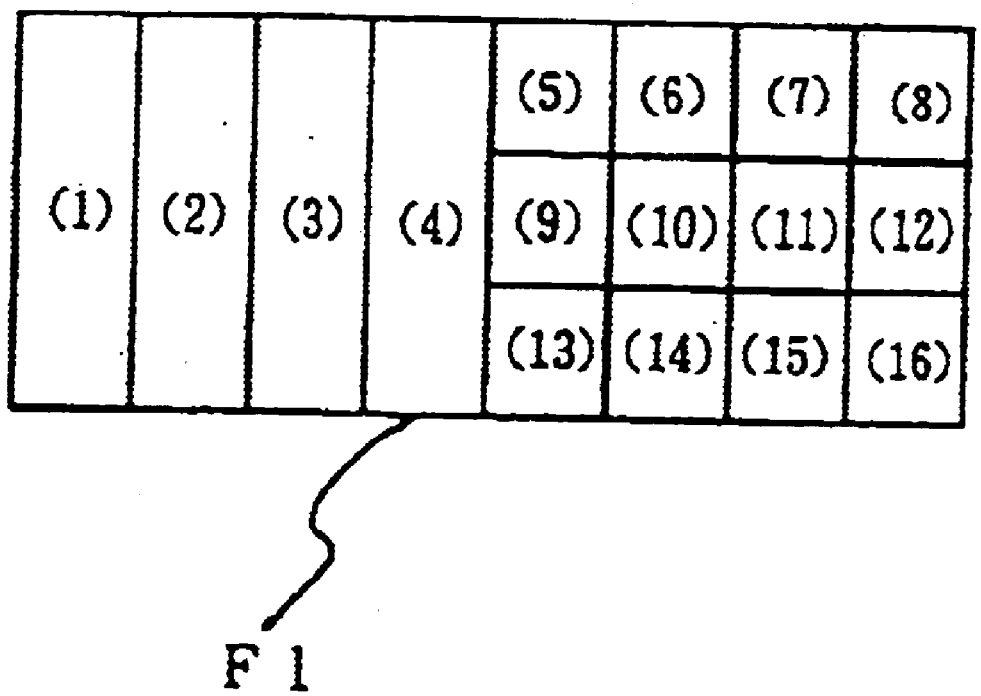
FIG. 49 shows an example of an arrangement of a container case for the membrane filter attachment method.

FIG. 49 is an example of an arrangement of the container case according to the membrane filter attachment method, in an example in which the specimens are beer bottles. In this diagram, items 1-4 are the specimen containers F1-1 (the beer bottles), 5-8 are the funnel unit F18, 9-12 are the culture medium containers (agar culture medium), 13 is the crown opening and closing jig, 14 is the filter suction jig unit F20, 15 is the collection box and 16 is the spare space.

EXAMPLE XV

Making Samples According to the Agar Pour-plate Method

The procedure is virtually the same as the direct method of making cultured bacteria solution (Example XIII), in which the solution is divided and diluted in a container containing a diluent and placed in a petri dish using a cylinder, the agar culture medium added, the petri dish covered with a lid and positioned at the solution promotion vibrating device D1, the culture medium and the diluted cultured bacteria solution mixed and the petri dish returned to a predetermined location in the container case F1 after predetermined operations have been completed.

EXAMPLE XVI

Making Samples for Other Microorganism Limit Testing

Procedures for other test methods such as the agar culture medium surface smear-plate method, the designated microorganism test or the effective retention test, are either virtually the same as the (Example XIII), the membrane filter attachment method (Example XIV) or the agar pour-plate method (Example XIV) or require a partial recombination of the procedures described up to now, and description thereof will be omitted.

EXAMPLE XVII

Making Samples for Indissoluble Particulate Measurement Testing

Figure 50:
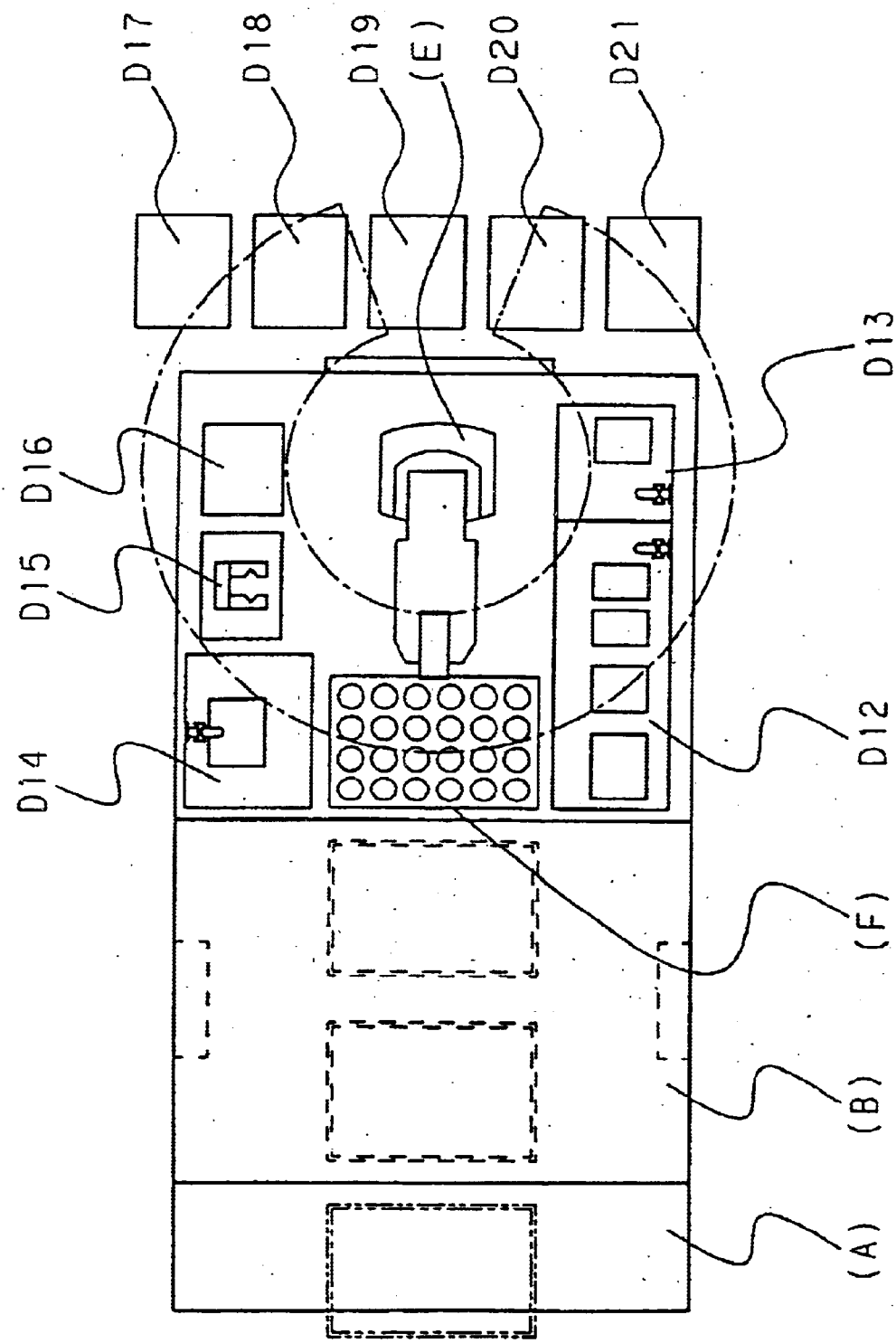
FIG. 50 shows a plan view of an example of an insoluble particulate testing apparatus.
Figure 51:
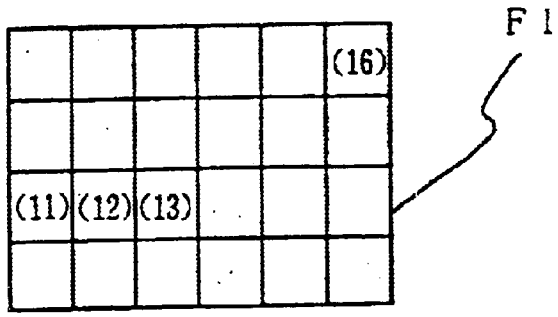
FIG. 51 shows a container case arrangement (1) of an insoluble particulate testing apparatus.
Figure 52:
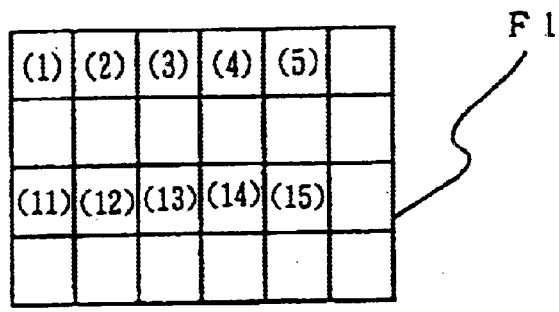
FIG. 52 shows a container case arrangement (2) of an insoluble particulate testing apparatus.
Figure 53:
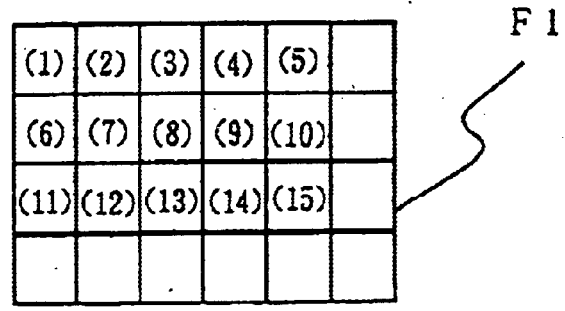
FIG. 53 shows a container case arrangement (3) of an insoluble particulate testing apparatus.
Figure 54:
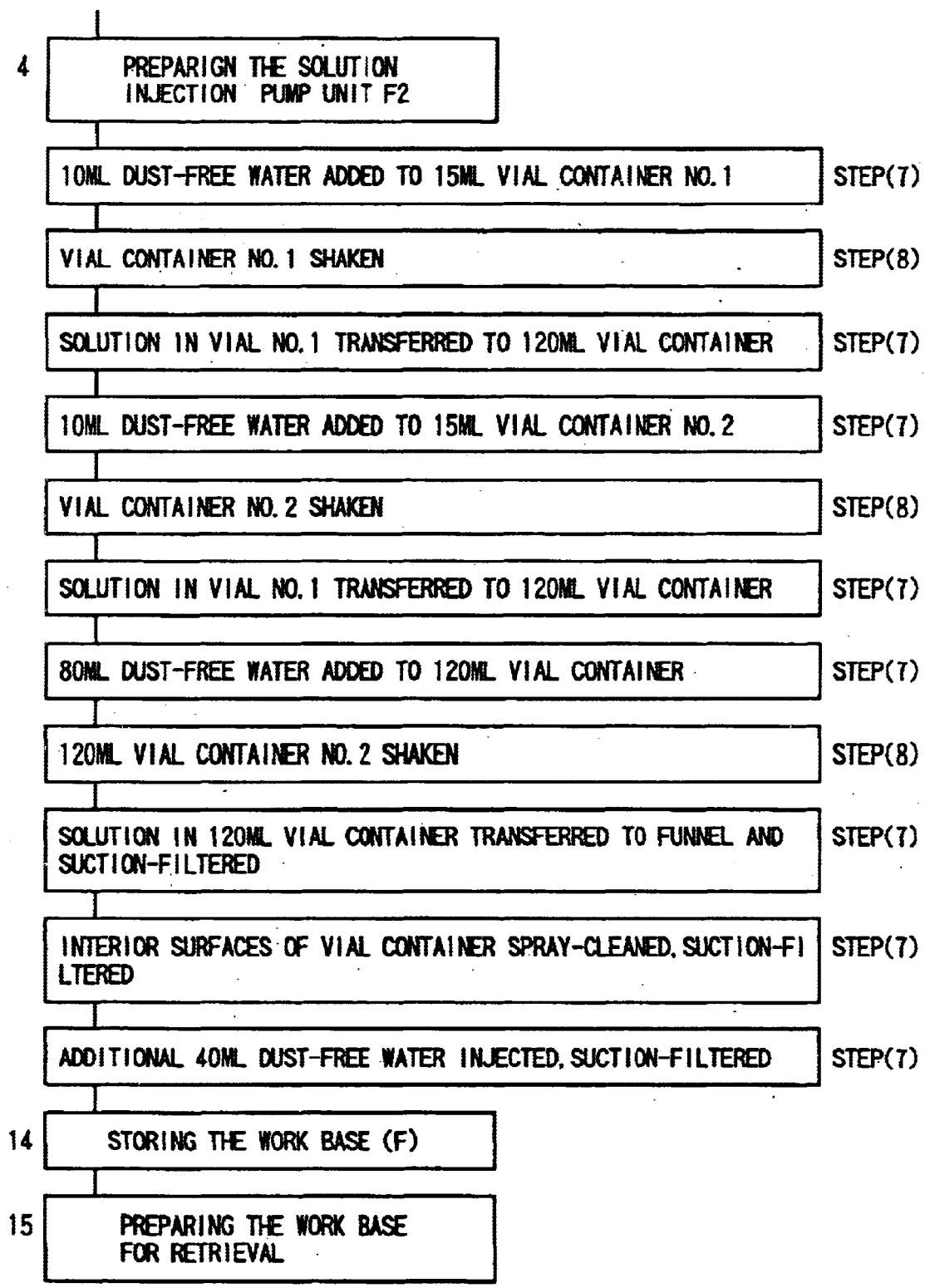
FIG. 54 is a flow chart showing an example of the order of operations in the testing of insoluble particulates.

An example of the apparatus in the case of indissoluble particulate measurement testing is shown in FIG. 50, with examples of container case arrangements shown in FIG. 51, FIG. 52 and FIG. 53 and an example of a procedural flow chart shown in FIG. 54. The numbers outside and to the right of the boxes are the step numbers of the present apparatus. As with the aforementioned Example XIII, the steps of stopping and unstopping are omitted. In FIGS. 51, 52 and 53, the item numbers 1-5 represent specimen containers F1-1, number 6–10 represent empty containers, 11–15 represent the funnel unit 18 and 16 is the particulate sampling petri dish. FIG. 51 is an example of the arrangement of a blank test, FIG. 52 is an example where there are many specimen containers F1-1 and FIG. 52 is an example where there are few specimen containers F1-1. The example shown in FIG. 53 shows a large number of sample containers being used at once. In FIG. 50, D12 is the solution injection and filtration unit, D13 is the container rinsing and drying unit, D14 is the injection counter, D15 is the vibrator, D16 is the sample filter dryer, D17 is the solution counter main unit, D18 is the suction unit for the dryer, D19 is the solution injection unit, D20 is the rinse-water pressure unit and D21 is the filter suction unit.

EXAMPLE XVIII

Using the Apparatus as a Divided-portion Injection Solution Test Unit (Such as for Chemical Analyses) and as a Chemical Reaction Test Unit Examples of operations I through XVII are themselves procedures involving the separation of solutions into portions for chemical reaction testing, so an explanation thereof is unnecessary and is omitted.

EXAMPLE XVI

When the Specimen Container F1-1 Changes with Each Lot

A set of equipment needed to make the sample is positioned at a predetermined location on the work base, the program needed for the operation is called up, and the procedure can be changed with each sample unit in accordance with the order. For this reason, the apparatus can without difficulty accommodate changes in the specimen, the type of container or the test order with each sample.

As is clear from the foregoing explanation, the types of containers which can be used with the foregoing automatic sterile testing apparatus is not limited to vials and ampules but can also include plastic bags, plastic bottles, eye-dropper bottles, transfusion bag syringes, test tubes, freshets, paper bags, spray cans, ordinary bottles and cans and other types of shapes. This means not only that sterile testing according to the membrane filter pressure method, the membrane filter suction method, the direct method, etc. can be conducted without human contamination of the environment and without contamination occurring in the interval between the exchange of lots; it also means that the apparatus can similarly accommodate the agar culture medium pour-plate method, the agar culture medium smear-plate method and other microorganism limit testing as well as indissoluble particulate testing and even chemical analysis and chemical reaction testing.

As explained above, except for the initial preparatory work, once the specimens have been positioned the automatic sterile testing apparatus according to the aforementioned embodiment makes it possible to carry out sterile testing without the intervention of human hands right up to the time the culture medium is placed in the culture tubes and moreover does so automatically even though the type of specimen changes; in addition, by providing automated equipment comprising a work base and a robot inside the clean booth it is possible to carry out dependably accurate automated operation of the apparatus in which recontamination by humans can be eliminated at a high level, thus eliminating as follows the problems described in the conventional-art section.

1) The present apparatus equips the main unit with a clean booth capability as necessary and moreover provides the apparatus itself with a rinsing and sterilization capability that is as free from fear of recontamination by human hands as possible and which thus provides a higher grade of test result validation.

2) The present apparatus employs a system of changing the needle used to inject the solution with every sample, eliminating the fear of contaminating the samples with the injection needle.

3) Changes in specimen type, amount or operating procedure can be flexibly accommodated simply by changing the program settings, thereby reducing manual labor involved (the work of preparing the apparatus) to that of simply replacing the container case, solution injection tube unit and sterile test unit; moreover, the work of preparing the apparatus by hand can be done in the same location, thus greatly simplifying the manual labor involved.

3) By placing the specimen container case, the solution injection pump unit and the various-solution injection pump unit all on the same base and by using a vertical-type stock device, the present apparatus makes it possible to provide an extremely compact apparatus that does not require a stock base even when the number of samples increases.

4) The apparatus is configured so as to allow containers holding specimens requiring long periods of time to dissolve in the solution to be removed from the operating line after they have been positioned at the vibrating device in order to permit other procedures to be carried out in the meantime, thus greatly improving per-time-unit processing ability.

5) Identical procedures can be repeated in between other steps without additional equipment simply by changing the program.

6) Virtually every type of specimen container can be accommodated simply by replacing the required equipment inside the container case, making it possible to utilize the apparatus not only as an automatic sterile testing apparatus but also for other applications as well.

As a result of the foregoing, with the automatic sterile testing apparatus according to the aforementioned embodiment the following advantages can be obtained:

Equipped with a self-disinfecting capability the apparatus operates without the intervention of human hands, thus eliminating the possibility of human error and the fear of contamination of the operating environment. Moreover, the apparatus changes the equipment required with each change in the sample lot, thus eliminating the problem of inter-lot contamination and greatly improving testing accuracy.

The present equipment can be located outside a clean room, so that an expensive clean room is not necessary. For this reason there is no work to be performed inside a clean room and the operator is freed from the requirement of having to perform under special operating conditions.

Except for the work of preparing the apparatus (attaching and detaching the work) all operations are entirely automated, so great energy savings can of course be expected at the same time as the burden of educating, training and managing operators can be greatly reduced.

The use of a multi-jointed robot makes it possible for one unit to flexibly accommodate the shape, size and number of virtually every type of manufactured (vials, ampules, eye-droppers, transfusion solution bags, etc.) as well as non-manufactured container.

The use of a vertical stock device and the use of the same location for the preparatory work stock as well as the post-testing work stock makes it possible to process 10 lots in one quarter to one fifth the space required of conventional equipment.

In addition, the processing capacity of the present apparatus can easily be doubled by providing a detachably attached work table (A), a work stock portion (B) and a work manipulation table (C) on the right side of the auxiliary work manipulation table (D) and a work manipulation robot (E) as shown in FIG. 38 and FIG. 39.

In addition, the aforementioned automatic sterile testing apparatus has room for the following further improvements.

1) The apparatus makes use of the existing clean room sterile technology as is, so there is room for further improving the safety as well as the degree of cleanliness.
2) Even after the pinch valve of the sterile test unit has been opened after a long period of time has elapsed the tube remains in a stuck position.
3) It is necessary to control the level of the fluid in the culture tube while rinsing.
4) The method of positioning the ampule is not perfect.
5) Using the existing injection and suction needles for small-mouth containers is difficult.

A description will now be given of a second embodiment of an automatic sterile testing apparatus designed to improve on the foregoing points.

In FIG. 55, which depicts the overall structure of the apparatus, the work stocker (B), as shown in FIG. 55 (front view of a stocker chamber), is entirely enclosed by a first covering G1 (not shown in the diagram) to form a sealed structure (hereinafter referred to as the stocker chamber (S)). A portion of the clean air is supplied from the second filter unit (G8) of the robot chamber to be discussed later via a dumper device G12 and an exhaust port G3 becomes the exhaust. The inside of the stocker chamber (S) thus comes to have a clean booth function.

A disinfectant spray device G6 (not shown in the diagram) having a spray nozzle G6-1 is provided on the inside of the stocker chamber (S), in such a way that the interior of the stocker chamber (S) including the work base (F) can be disinfected.

In addition, as shown in FIG. 55 (front view of a robot chamber), the periphery of the location at which the work manipulation table (C), the auxiliary work manipulation table (D) and the work manipulation robot (E) are positioned is entirely enclosed by a second covering G7 to form a sealed structure (hereinafter referred to as the robot chamber (R)). A second filter unit G8 is attached to the upper portion, an exhaust port G9 is provided on a lower portion side surface and a conservation door G10 is provided on the front.

Figure 56:
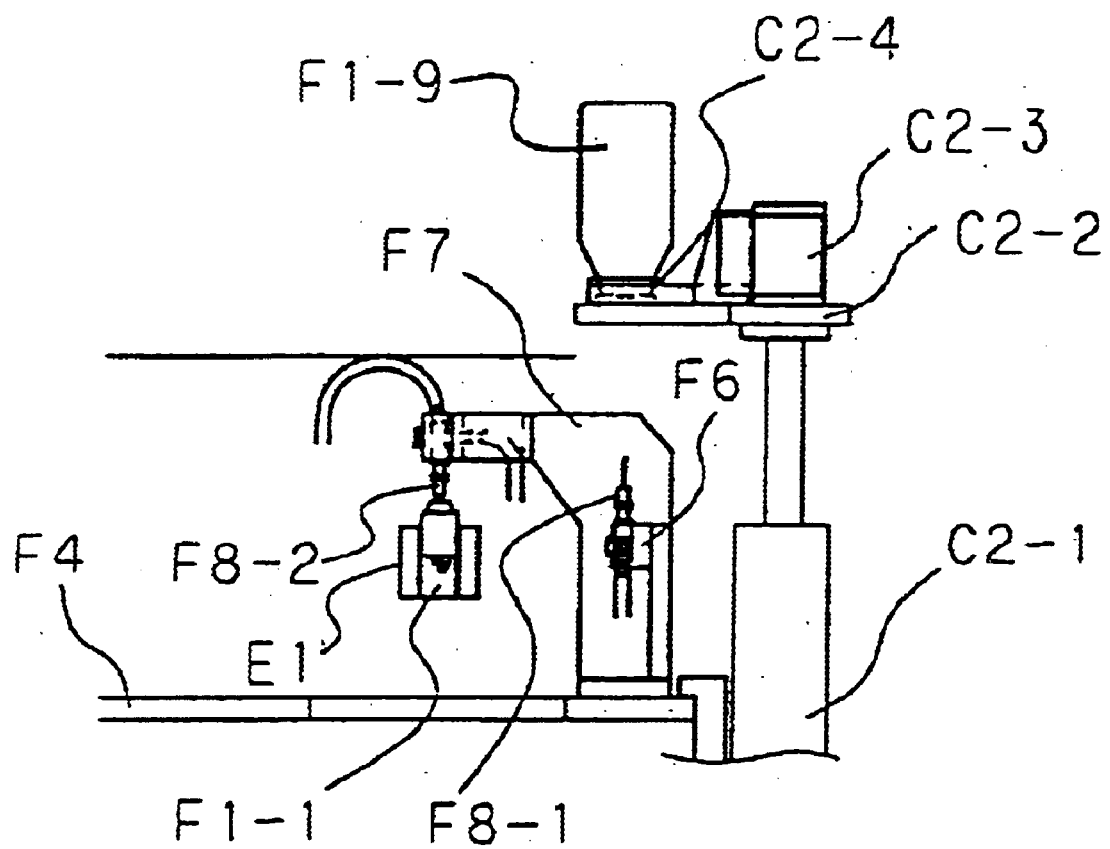
FIG. 56 is a first diagram for explaining a method for processing ampules using an automatic sterile testing apparatus.

When processing ampules with the aforementioned automatic sterile testing apparatus (of the first embodiment)—that is, when using auxiliary containers with the top portion open and with rubber stoppers attached to the bottom portion—there are times when leaks occur during handling due to the shape of the ampule container as well as the amount of fluid contained therein. Moreover, during handling the robot hand E1 is positioned directly above the auxiliary container, which is undesirable when viewed in terms of test accuracy and reliability. This problem is solved by the following method:

FIG. 56 shows a condition in which the specimen container is grasped and supported by the robot hand E1, the neck portion is broken, the solution injection needle F8-2 is inserted into the opening of the opened specimen container (ampule) F1-1, the empty vial container F1-9 (which can be an empty container once used for the preparatory rinsing fluid) is positioned at the grasping hook C3-4 of the device C2 for grasping and raising or lowering the solution container, the solution suction needle F8-1 is inserted into the vial container F1-9, the solution transfer pump F5 is rotated in reverse and the specimen fluid is sucked up and discharged into the vial container F1-9. At this time the solution injection needle F8-2 and the solution suction needle F8-1 perform functions directly contrary to their names.

Figure 57:
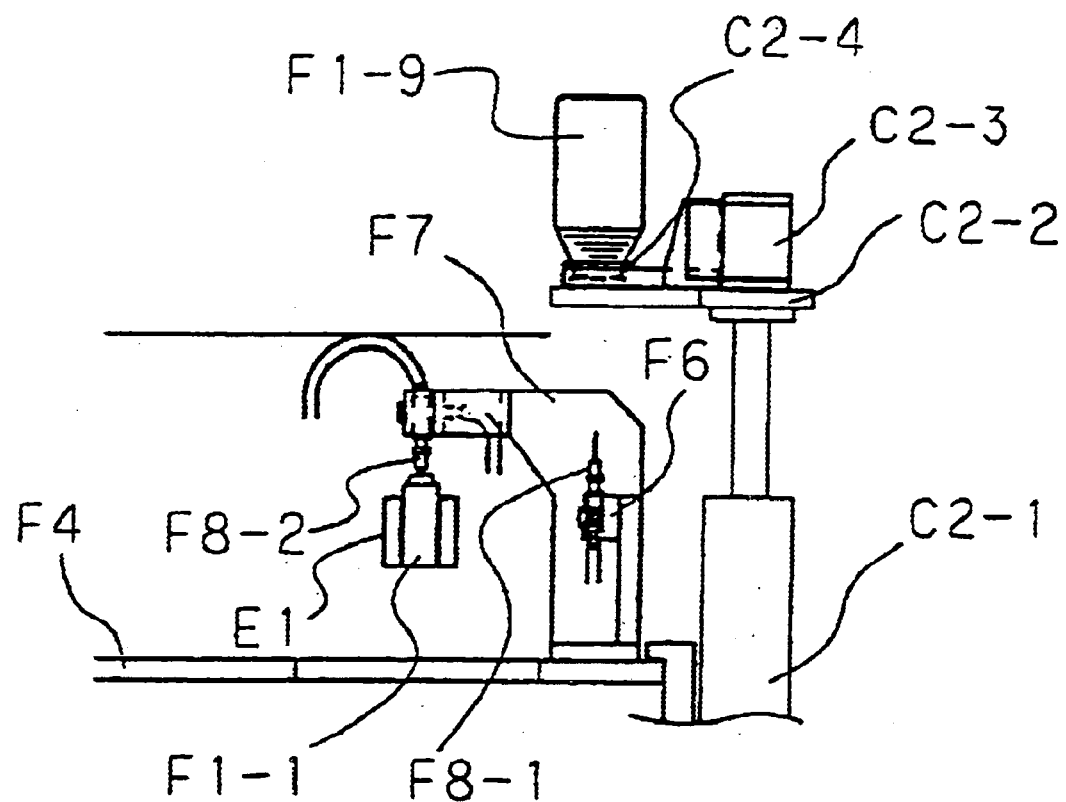
FIG. 57 is a second diagram for explaining a method for processing ampules using an automatic sterile testing apparatus.
Figure 58:
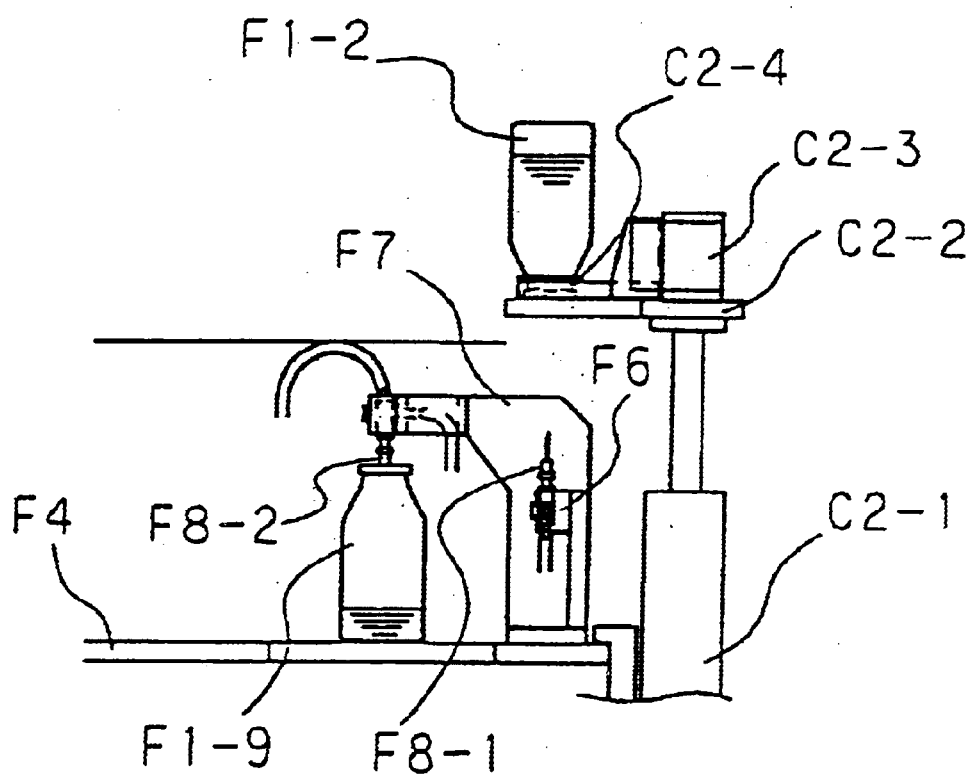
FIG. 58 is a third diagram for explaining a method for processing ampules using an automatic sterile testing apparatus.
Figure 59:
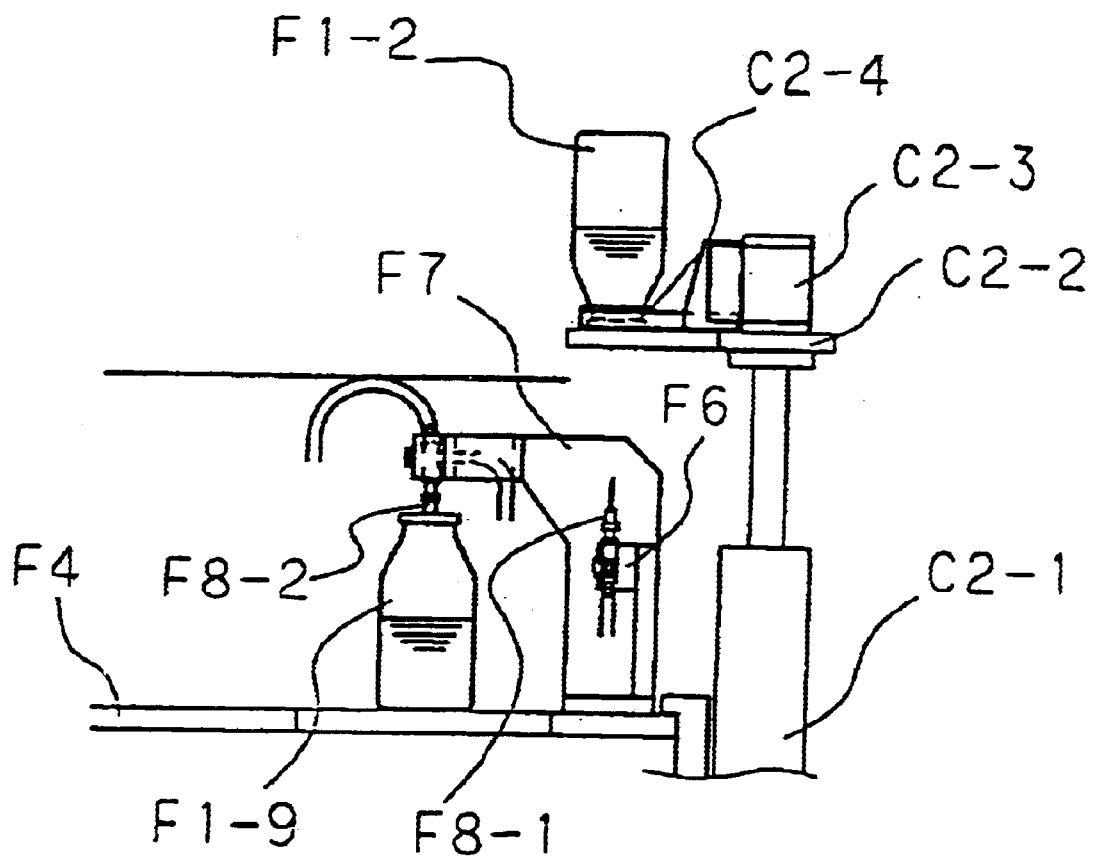
FIG. 59 is a fourth diagram for explaining a method for processing ampules using an automatic sterile testing apparatus.

In the condition shown in FIG. 57, specimen fluid stays in the solution suction needle F8-1 of the solution injection tube unit F8, the solution injection needle F8-2 and the connecting tube F8-3, so the vial container F1-9 is positioned at the device C3 for grasping and raising or lowering a specimen container and a flushing fluid F1-2 is positioned at the grasping hook C3-4 of the device C2 for grasping and raising or lowering the solution container and the solution transfer pump F5 rotated properly to flush the remaining fluid into the vial container F1-9 (the condition shown in FIG. 58 and FIG. 59). The flushing fluid is placed in the vial container F1-9 and its volume increased in order to improve the accuracy with which the sample is apportioned during filtering.

Figure 60:
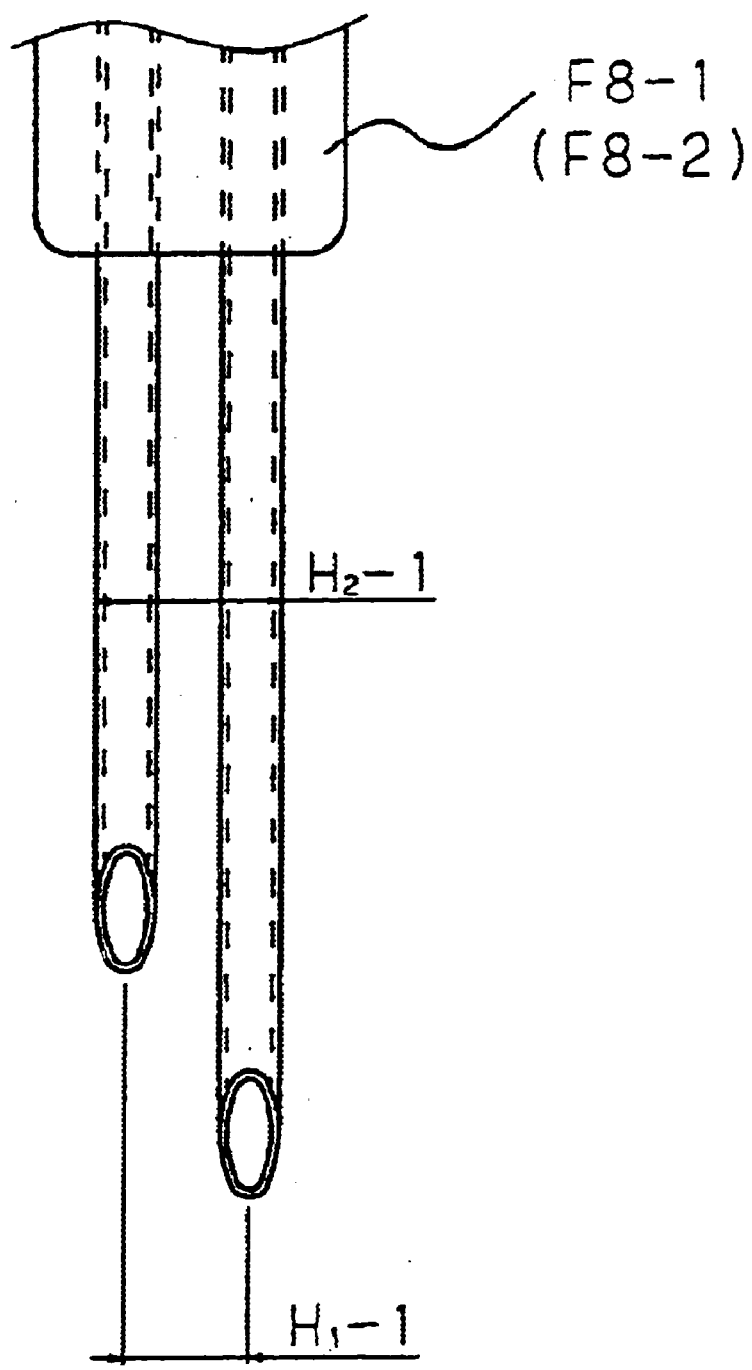
FIG. 60 shows the structure of a solution needle used in the automatic sterile testing apparatus as shown in FIG. 1 and FIG. 2.

As shown in FIG. 60, the aforementioned solution suction needle F8-1 and solution injection needle F8-2 each comprise two separate needles, so that the smallest diameter that permits needle insertion is H2-1. The container and the needles will be out of alignment with each other if the edge portion of the container is placed by the robot hand E1 in the space between the two needles H1-1; such misalignment can be a source of trouble.

Figure 61:
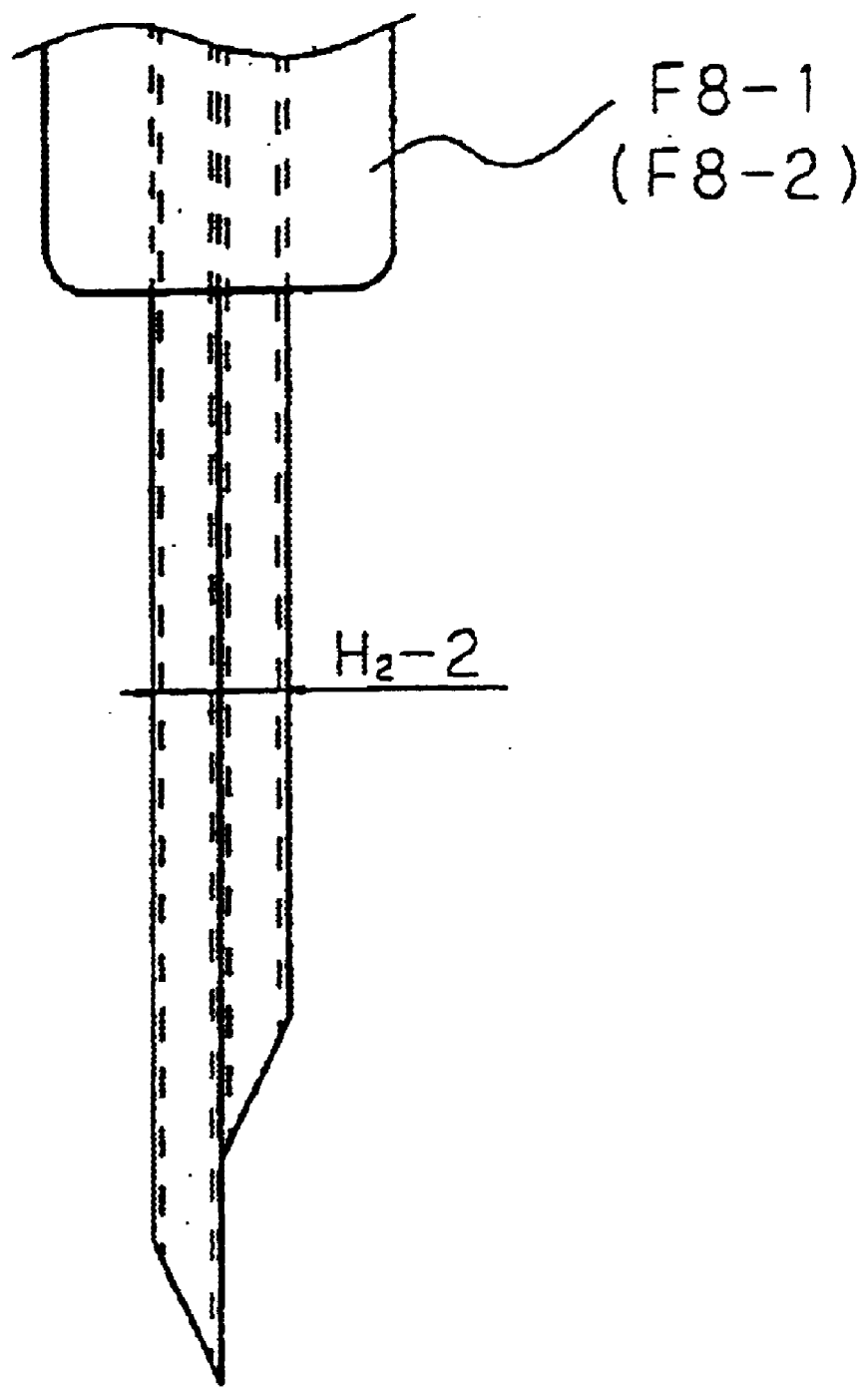
FIG. 61 shows the structure of a solution needle used in the automatic sterile testing apparatus according to a second embodiment of the present invention.

As shown in FIG. 61, however, the present invention places the two needles into contact with each other along the length of their long sides, so that the tip portions of both needles are aligned along the line of contact and the line H2-1 of FIG. 60 becomes the line H2-2 of FIG. 61, with the line H1-1=0. Provided the tip of the needle is within the inner diameter of the portion of the container into which the needle is to be inserted, the slanted section of the needle will function as a guide for the needle and will automatically center the needle.

Figure 62:
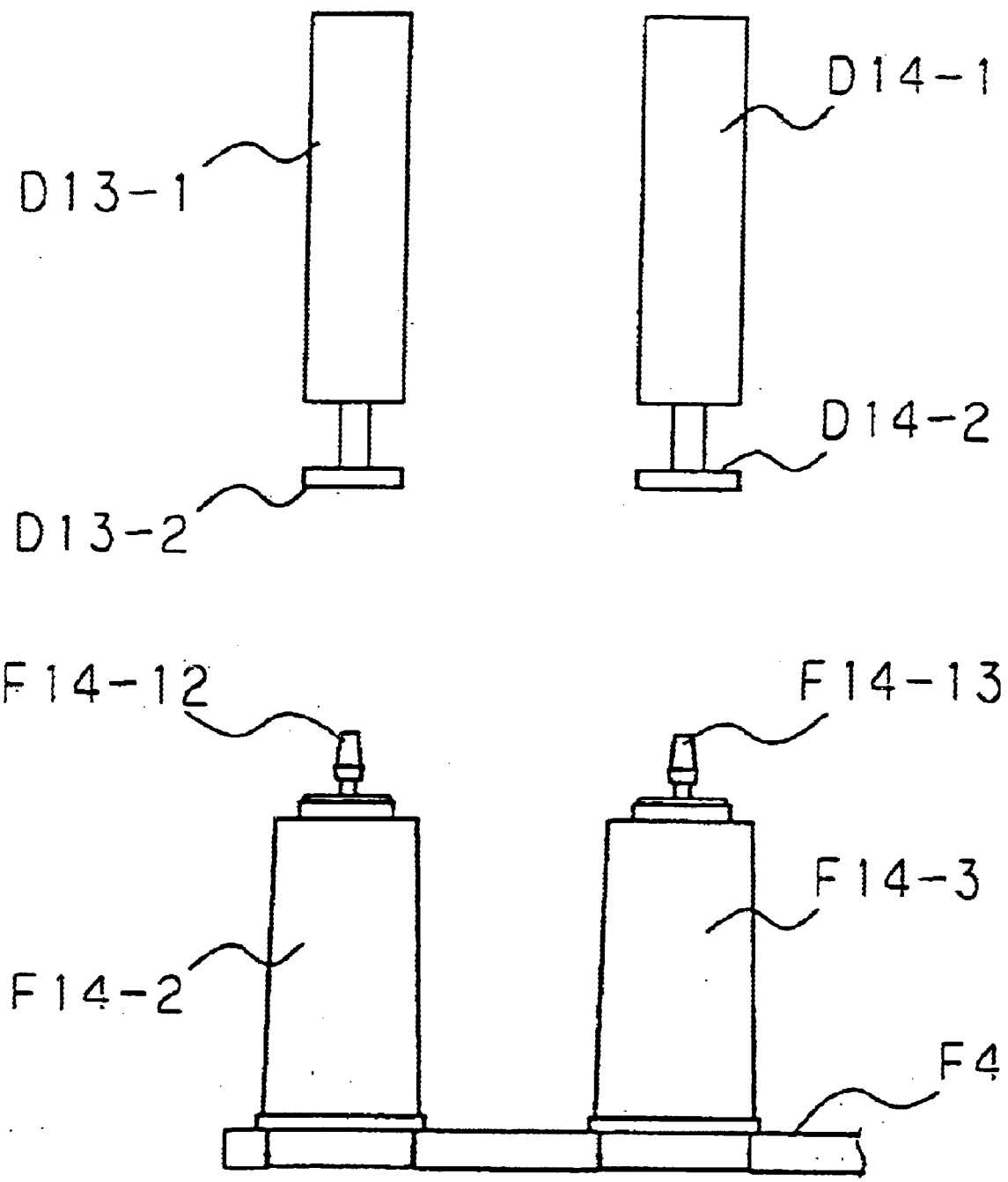
FIG. 62 is a first diagram for explaining a method for controlling a level of a fluid of a culture tube using the automatic sterile testing apparatus according to a second embodiment of the present invention.
Figure 63:
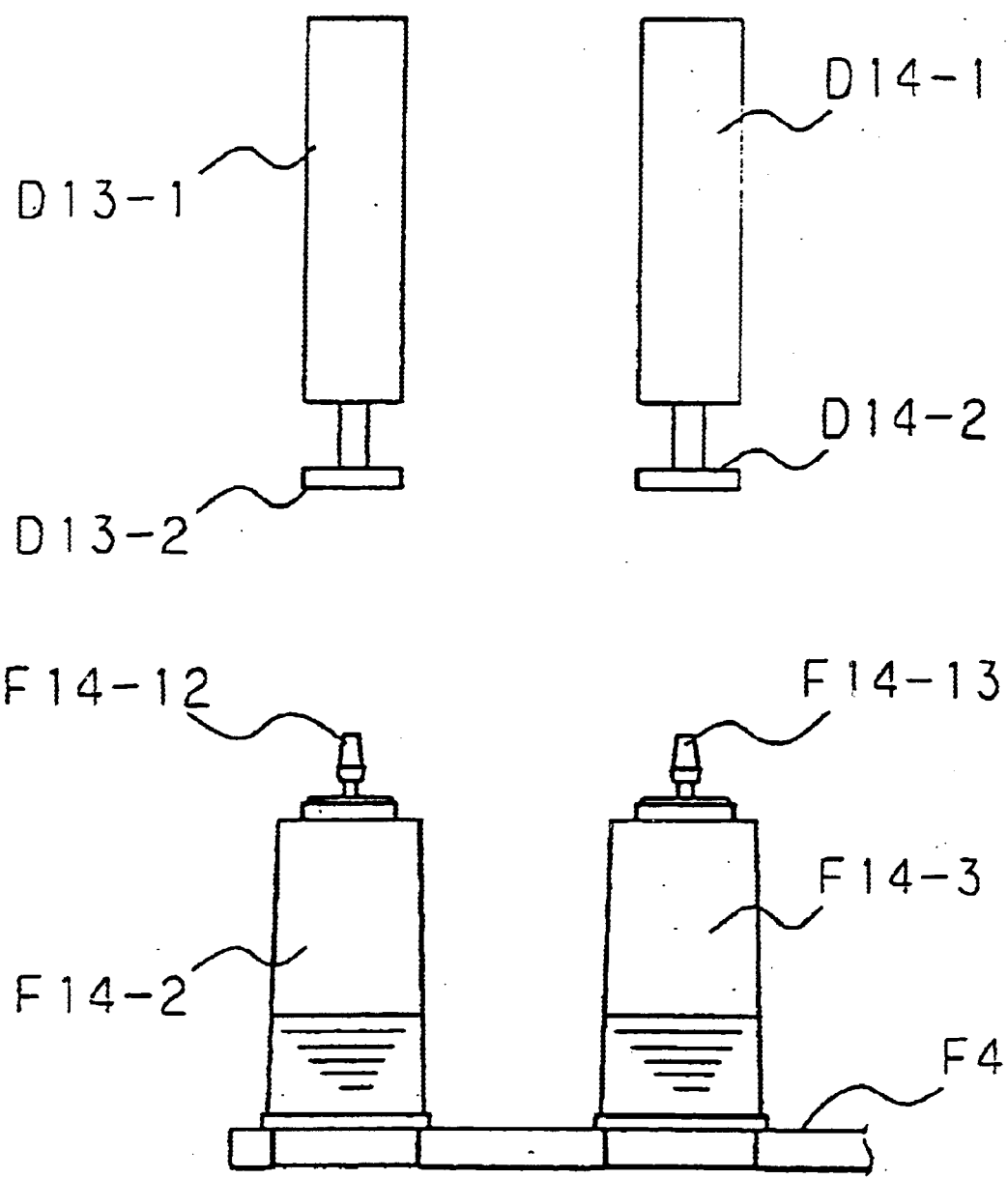
FIG. 63 is a second diagram for explaining a method for controlling a level of a fluid of a culture tube using the automatic sterile testing apparatus according to a second embodiment of the present invention.
Figure 64:
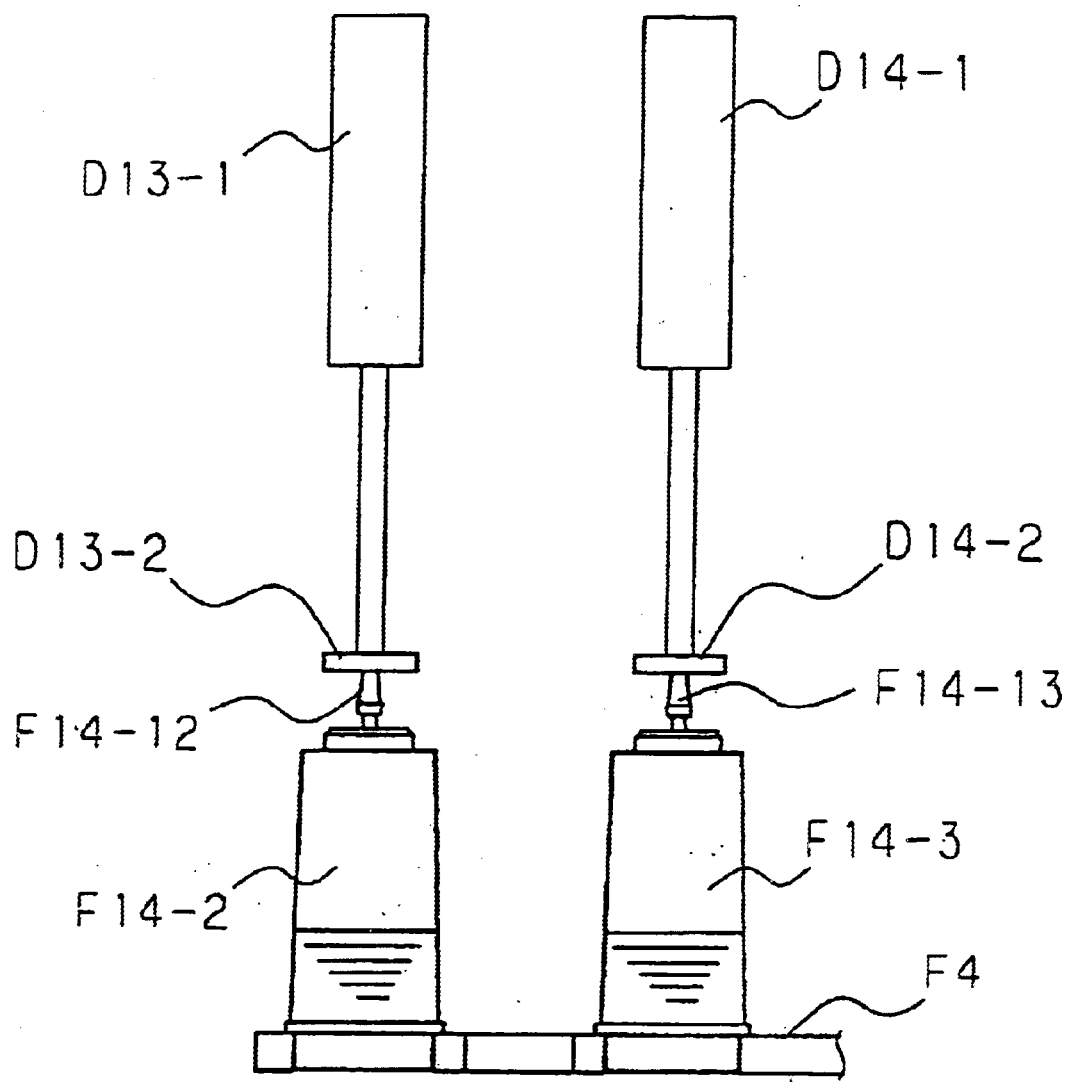
FIG. 64 is a third diagram for explaining a method for controlling a level of a fluid of a culture tube using the automatic sterile testing apparatus according to a second embodiment of the present invention.

When transferring the rinsing fluid to the sterile test unit F14 for rinsing, it is necessary to maintain the fluid level of the first culture tube F14-2 and the second culture tube F14-3 of the sterile test unit F14 at the optimum condition for those specimens; the method for doing so will now be explained. As shown in FIG. 62, before beginning the rinsing the first cylinder D13-1 and the second cylinder D14-1 are activated to raise and open a first exhaust port weight D13-2 and a second exhaust port weight D14-2 closing the first upper exhaust port F14-12 and the second upper exhaust port F14-13, respectively. When rinsing fluid is injected up to a predetermined position in this open condition (the condition shown in FIG. 63), the first exhaust port weight D13-2 and the second exhaust port weight D14-2 are lowered to close the first upper exhaust port F14-12 and the second upper exhaust port F14-13 as shown in FIG. 64. In this manner the level of fluid can be maintained at optimum conditions for those specimens while rinsing.

The stocker chamber is built so that it can be sprayed with disinfectant, which disinfectant it was originally thought would comprise hibitane, formalin, hydrogen peroxide gas, ozone or alcohol, etc. Under actual test conditions, however, the following problems arose: Hibitane leaves a post-volatilization residue which progressively accumulates. It takes time to flush out formalin residue, requiring spraying and fumigating each and every set, which cannot be done. Hydrogen peroxide gas and ozone would require separate generation and dissolution devices. Before opening the door to the robot chamber the atmosphere of the stocker chamber must be returned to its original state, but formalin, hydrogen peroxide gas and ozone cannot be removed in a short period of time. Alcohol is comparatively easy to handle in terms of equipment but spraying it raises the danger of an explosion and hence it cannot be used for reasons of safety. After considering and testing a variety of disinfectants all of the foregoing problems were solved by the use of a strong-acid electrolytic solution.

Like the stocker chamber, the robot chamber, too, is built so that it can be sprayed with disinfectant, but as with the stocker chamber hibitane, formalin, hydrogen peroxide gas, ozone and alcohol cannot be used. However, the use of a strong-acid electrolytic solution as with the stocker chamber requires that the instruments positioned in the robot chamber be resistant to corrosion, which is difficult to do at the present level of technology and difficult to justify in terms of cost-effectiveness. This problem is solved, however, by including a UV- and ozone-generating device G13 inside the robot chamber (R) as shown in FIG. 55 and activating the UV- and ozone-generating device G13 whenever the present apparatus is not in use so as to sterilize the interior of the robot chamber (R).

As is clear from the foregoing explanation, an automatic sterile testing apparatus according to a second embodiment of the present invention like that described above improves test accuracy and is more readily used with a wider array of possible specimen containers, and provides the following further improvements.

1) A system of spraying a strong-acid electrolytic solution as a disinfectant has been adopted as the method for sterilizing the stocker chamber, thereby greatly simplifying the test environment sterilization equipment and eliminating all safety concerns.
2) The culture tube exhaust ports can be opened and closed either individually or all at once, making it possible to inject only the desired amount of fluid whether or not the tube is stuck.
3) Particularly when rinsing, the height of the level of the fluid inside the culture tubes greatly influences the effectiveness of the rinse; by controlling the opening and closing of the exhaust ports of the culture tubes, however, the specimens can be tested under optimum fluid level conditions.
4) When filling the ampules some of these do not set properly; however, all the specimen fluid remaining inside the tube unit can be collected simply by using the same station and running the pump in reverse.
5) With the automatic sterile testing apparatus according to the first embodiment the structure of the solution needle could only accommodate interior diameters of approximately 10 mm or less; with the apparatus of the second embodiment, however, the aforementioned needle structure can also freely accommodate containers having even smaller-diameter mouths, thus not only greatly broadening the range of application of the apparatus but also greatly improving the accuracy of the equipment.

The present invention is not limited to the specifically disclosed embodiments, and variations may be made without departing from the scope of the present invention.

What is claimed is:

1. An automatic testing apparatus such that the specimen to be tested is changed on a work base-unit basis, comprising:

a work base mounting the test specimen and equipment for the testing of the specimen;

a multi-joint work manipulation robot device having a robot hand for grasping and moving according to a previous procedure, said test specimen and equipment mounted on said work base set at a testing position for performing tests on the test specimen mounted on the work base;

a first partition chamber provided to enclose the robot device and a work manipulation table;

a work base providing mechanism for providing the work base to the testing position, said work base providing mechanism comprising a sealed second partition chamber holding a plurality of work bases;

said first partition chamber being in communication with the said second partition chamber and both partition chambers being together sealed from contamination from outside and fro human contact; and wherein any one of the plurality of work bases is taken out from the second partition chamber to the first partition chamber where predetermined test are performed on the test specimen mounted on the thus-provided work base in the first partition chamber;

a device and a temporary placement area in said first partition chamber positioned separately from the work manipulation table and that can be use in common; and said device comprising an ampule opening device for opening an ampule mounted as a test specimen on the work base, said ampule opening device comprising:

a rotary blade for cutting the ampule, and a u-shaped notch, or empty tube, such that the robot device takes said ampule in the robot hand and contacts the ampule to the rotary blade for cutting the ampule so as to notch the ampule, inserts the neck portion of the ampule in the u-shaped notch, or empty tube, and opens the ampule.

2. The automatic testing apparatus as claimed in claim 1, wherein the robot grasps the ampule in the robot hand and contacts the bottom portion of the ampule in a grasping position setting bar so as to set the corresponding positions of the ampule and the robot hand.

* * * * *